United States Patent
Cherney et al.

(10) Patent No.: US 6,927,216 B2
(45) Date of Patent: Aug. 9, 2005

(54) CYCLIC SULFONYL COMPOUNDS AS INHIBITORS OF METALLOPROTEASES

(75) Inventors: Robert J. Cherney, Newark, DE (US); Bryan W. King, Wilmington, DE (US)

(73) Assignee: Bristol-Myers Squibb Pharma Company, Princeton, NJ (US)

(*) Notice: Subject to any disclaimer, the term of this patent is extended or adjusted under 35 U.S.C. 154(b) by 326 days.

(21) Appl. No.: 09/954,379

(22) Filed: Sep. 17, 2001

(65) Prior Publication Data

US 2002/0086853 A1 Jul. 4, 2002

Related U.S. Application Data

(60) Provisional application No. 60/237,607, filed on Oct. 3, 2000.

(51) Int. Cl.⁷ .................... A61K 31/54; A61K 31/47; A61P 29/00; C07D 279/00; C07F 9/28
(52) U.S. Cl. .................... 514/222.2; 514/314; 514/342; 514/372; 544/3; 546/172; 546/271.1; 548/111; 548/206; 548/213; 548/214
(58) Field of Search ................. 514/222.2, 314, 514/342, 372; 544/3; 546/172, 271.1; 548/111, 206, 213, 214

(56) References Cited

FOREIGN PATENT DOCUMENTS

| EP | 780386 A1 | 6/1997 |
|---|---|---|
| EP | 818442 A2 | 1/1998 |
| EP | 1004578 A2 | 5/2000 |
| WO | WO 9720824 A | 6/1997 |
| WO | WO 9941246 A | 8/1999 |
| WO | WO 9958531 A | 11/1999 |
| WO | WO 9965867 A | 12/1999 |

OTHER PUBLICATIONS

CAPLUS printout for EP 0 342 456, Nov. 23, 1989.*
Luisi, G. et al, Pseudopeptides containing isothiazolidine–1,1–dioxide–3–carboxylic acid: synthesis and properties of (S)–isothiazolidine–1,1–dioxide–3–carboxylic acid, a new gamma–sultam analog of pyroglutamic acid, Archiv. Der. Pharmazie, vol. 326, no 3, 1993, pp. 139–141.

* cited by examiner

Primary Examiner—Brenda Coleman
(74) Attorney, Agent, or Firm—Jing G. Sam; David H. Vance

(57) ABSTRACT

The present application describes novel cyclic sulfonyl derivatives of formula I:

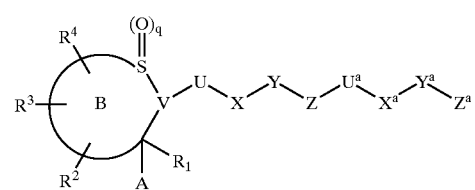

or pharmaceutically acceptable salt forms thereof, wherein ring B is a 5–7 membered cyclic system containing from 0–2 heteroatoms selected from O, N, $NR^a$, and $S(O)_p$, and 0–1 carbonyl groups and the other variables are defined in the present specification, which are useful as metalloprotease inhibitors.

24 Claims, No Drawings

CYCLIC SULFONYL COMPOUNDS AS INHIBITORS OF METALLOPROTEASES

CROSS-REFERENCE TO RELATED APPLICATIONS

This application claims the priority benefit of U.S. Provisional Application No. 60/237,607, filed Oct. 3, 2000, which is expressly incorporated fully herein by reference.

FIELD OF THE INVENTION

This invention relates generally to novel cyclic sulfonyl compounds as metalloproteases inhibitors, pharmaceutical compositions containing the same, and methods of using the same.

BACKGROUND OF THE INVENTION

There is now a body of evidence that metalloproteases (MP) are important in the uncontrolled breakdown of connective tissue, including proteoglycan and collagen, leading to resorption of the extracellular matrix. This is a feature of many pathological conditions, such as rheumatoid and osteoarthritis, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMPs (tissue inhibitors of metalloprotease), which form inactive complexes with the MP's.

Osteo- and Rheumatoid Arthritis (OA and RA respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. *J. Bone Joint Surg.* 1970, 52A, 424–434). There are four classes of protein degradative enzymes in mammalian cells: serine, cysteine, aspartic and metalloproteases. The available evidence supports that it is the metalloproteases that are responsible for the degradation of the extracellular matrix of articular cartilage in OA and RA. Increased activities of collagenases and stromelysin have been found in OA cartilage and the activity correlates with severity of the lesion (Mankin et al. *Arthritis Rheum.* 1978, 21, 761–766, Woessner et al. *Arthritis Rheum.* 1983, 26, 63–68 and Ibid. 1984, 27, 305–312). In addition, aggrecanase has been identified as providing the specific cleavage product of proteoglycan found in RA and OA patients (Lohmander L. S. et al. *Arthritis Rheum.* 1993, 36, 1214–22).

Therefore, metalloproteases (MP) have been implicated as the key enzymes in the destruction of mammalian cartilage and bone. It can be expected that the pathogenesis of such diseases can be modified in a beneficial manner by the administration of MP inhibitors, and many compounds have been suggested for this purpose (see Wahl et al. *Ann. Rep. Med. Chem.* 1990, 25, 175–184, AP, San Diego).

Tumor necrosis factor (TNF) is a cell-associated cytokine that is processed from a 26 kd precursor form to a 17 kd active form. TNF has been shown to be a primary mediator in humans and in animals, of inflammation, fever, and acute phase responses, similar to those observed during acute infection and shock. Excess TNF has been shown to be lethal. There is now considerable evidence that blocking the effects of TNF with specific antibodies can be beneficial in a variety of circumstances including autoimmune diseases such as rheumatoid arthritis (Feldman et al, *Lancet,* 1994, 344, 1105) and non-insulin dependent diabetes melitus (Lohmander L. S. et al. *Arthritis Rheum.* 36, 1993, 1214–22) and Crohn's disease (MacDonald T. et al. *Clin. Exp. Immunol.* 81, 1990, 301).

Compounds which inhibit the production of TNF are therefore of therapeutic importance for the treatment of inflammatory disorders. Recently it has been shown that a matrix metalloprotease or family of metalloproteases, hereafter known as TNF-convertases (TNF-C), as well as other MP's are capable of cleaving TNF from its inactive to active form (Gearing et al *Nature* 1994, 370, 555). Compounds of the present invention may provide a means of mechanism based therapeutic intervention for diseases including but not restricted to septic shock, haemodynamic shock, sepsis syndrom, aortic aneurisms, post ischemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, OA, RA, multiple sclerosis, radiation damage, hyperoxic alveolar injury, periodontal disease, HIV and non-insulin dependent diabetes melitus.

Since excessive TNF production has been noted in several disease conditions also charactarized by MMP-mediated tissue degradation, compounds which inhibit both MMPs and TNF production may also have a particular advantage in diseases where both mechansisms are involved.

EP 0,780,286 describes MMP inhibitors of formula A:

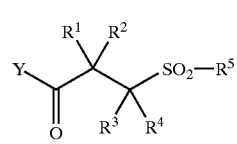

wherein Y can be NHOH, $R^1$ and $R^2$ can combine to form a cycloalkyl or heterocyclo alkyl group, $R^3$ and $R^4$ can be a variety of groups including H, and $R^5$ can be substituted aryl.

WO 97/20824 depicts MMP inhibitors of formula B:

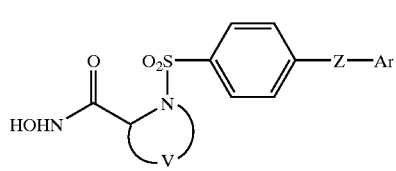

wherein ring V contains six atoms, Z is O or S, and Ar is an aryl or heteroaryl group. Ar is preferably a monocyclic aryl group with an optional para substituent or an unsubstituted monocyclic heteroaryl group.

EP 0,818,442 illustrates MMP inhibitors of formula C:

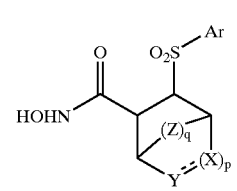

wherein Ar is optionally substituted phenyl or naphthyl, Z can be absent and X and Y can be a variety of substituents. Compounds of this sort are not considered to be part of the present invention.

Thus, it is desirable to find novel compounds that are inhibitors of the above-discussed enzymes.

SUMMARY OF THE INVENTION

Accordingly, one object of the present invention is to provide novel cyclic hydroxamic acids useful as metalloprotease inhibitors or pharmaceutically acceptable salt form thereof.

It is another object of the present invention to provide pharmaceutical compositions comprising a pharmaceutically acceptable carrier and a therapeutically effective amount of at least one of the compounds of the present invention or a pharmaceutically acceptable salt form thereof.

It is another object of the present invention to provide a method for treating inflammatory disorders, comprising: administering to a host, in need of such treatment, a therapeutically effective amount of at least one of the compounds of the present invention or a pharmaceutically acceptable salt form thereof.

It is another object of the present invention to provide novel compounds of the present invention for use in therapy.

It is another object of the present invention to provide the use of novel compounds of the present invention for the manufacture of a medicament for the treatment of a condition or disease mediated by MMPs, ADAMs, TNF, aggrecanase, or a combination thereof.

These and other objects, which will become apparent during the following detailed description, have been achieved by the inventors' discovery that compounds of formula (I):

I or pharmaceutically acceptable salt forms thereof, wherein q, A, B, $R^1$, $R^2$, $R^3$, $R^4$, V, X, Y, Z, $U^a$, $X^a$, $Y^a$, and $Z^a$ are defined below, are effective inhibitors of MMPs, ADAMs, TNF, aggrecanase, or combinations thereof.

DETAILED DESCRIPTION OF PREFERRED EMBODIMENTS

[1] Thus, in an embodiment, the present invention provides a novel compound of formula I:

I or a stereoisomer or pharmaceutically acceptable salt form thereof, wherein;

A is selected from $-COR^5$, $-CO_2H$, $CH_2CO_2H$, $-CO_2R^6$, $-CONHOH$, $-CONHOR^5$, $-CONHOR^6$, $-N(OH)$ $COR^5$, $-SH$, $-CH_2SH$, $-SONHR^a$, $-SN_2H_2R^a$, $-PO$ $(OH)_2$, and $-PO(OH)NHR^a$;

V is $CR^{2b}$ or N;

ring B, including V and $S(O)_q$, is a 4–8 membered non-aromatic heterocycle consisting of: $S(O)_q$, V, carbon atoms, 0–1 carbonyl groups, 0–1 double bonds, and 0–2 additional ring heteroatoms selected from O, N, $NR^2$, and $S(O)_p$, provided that ring B has no more than a total of one O and $S(O)_p$ groups and provided that ring B has other than a S—S, S—O, S—N, or N—O bond;

U is absent or is selected from: O, $NR^{a1}$, C(O), C(O)O, OC(O), $C(O)NR^{a1}$, $NR^{a1}C(O)$, OC(O)O, $C(O)NR^{a1}$, $NR^{a1}C(O)O$, $NR^{a1}C(O)NR^{a1}$, $S(O)_p$, $S(O)_pNR^{a1}$, $NR^{a1}S(O)_p$, and $NR^{a1}SO_2NR^{a1}$;

X is absent or selected from $C_{1-10}$ alkylene, $C_{2-10}$ alkenylene, and $C_{2-10}$ alkynylene;

Y is absent or is selected from: O, $NR^{a1}$, C(O), C(O)O, OC(O), $C(O)NR^{a1}$, $NR^{a1}OC(O)$, OC(O)O, $OC(O)NR^{a1}$, $NR^{a1}C(O)O$, $NR^{a1}C(O)NR^{a1}$, $S(O)_p$, $S(O)_pNR^{a1}$, $NR^{a1}S(O)_p$, and $NR^{a1}SO_2NR^{a1}$;

Z is absent or selected from a $C_{3-13}$ carbocycle substituted with 0–5 $R^b$ and a 5–14 membered heterocycle consisting of: carbon atoms and 1–4 heteroatoms selected from the group consisting of N, O, and S and substituted with 0–5 $R^b$;

$U^a$ is absent or is selected from: O, $NR^{a1}$, C(O), C(O)O, OC(O), $C(O)NR^{a1}$, $NR^{a1}C(O)$, OC(O)O, $OC(O)NR^{a1}$, $NR^{a1}C(O)O$, $NR^{a1}C(O)NR^{a1}$, $S(O)_p$, $S(O)_pNR^{a1}$, $NR^{a1}S(O)_p$, and $NR^{a1}SO_2NR^{a1}$;

$X^a$ is absent or selected from $C_{1-10}$ alkylene, $C_{2-10}$ alkenylene, and $C_{2-10}$ alkynylene;

$Y^a$ is absent or is selected from: O, $NR^{a1}$, C(O), C(O)O, OC(O), $C(O)NR^{a1}$, $NR^{a1}C(O)$, OC(O)O, $OC(O)NR^{a1}$, $NR^aOC(O)O$, $NR^{a1}C(O)NR^{a1}$, $S(O)_p$, $S(O)_pNR^{a1}$, $NR^{a1}S(O)_p$, and $NR^{a1}SO_2NR^{a1}$;

$Z^a$ is selected from a $C_{3-13}$ carbocycle substituted with 0–5 $R^c$ and a 5–14 membered heterocycle consisting of: carbon atoms and 1–4 heteroatoms selected from the group consisting of N, O, and S and substituted with 0–5 $R^c$;

provided that when U-X—Y are $CH_2$, $U^a$-$X^a$—$Y^a$ are absent, and Z is phenyl, then $Z^a$ is other than a 2-substituted phenyl ring or a 3,5-disubstituted phenyl ring;

provided that V, U, X, Y, Z, $U^a$, $X^a$, $Y^a$, $Z^a$, combine to form other than a N—N, N—O, O—N, O—O, $S(O)_p$—O, O—$S(O)_p$ or $S(O)_p$—$S(O)_p$ group, an unsubstituted naphthyl, a substituted naphthyl wherein the substituent is 1–3 atoms in length, an unsubstituted phenyl, a substituted phenyl wherein the substituent is 1–3 atoms in length, an unsubstituted benzyl, or a substituted benzyl wherein the substituent is 1–3 atoms in length;

$R^1$ is selected from H, $C_{1-6}$ alkyl, $OR^a$, $NR^aR^{a1}$, CN, $CF_3$, $S(O)_pR^a$, phenyl and benzyl;

$R^2$ is selected from Q, $C_{1-10}$ alkylene-Q substituted with 0–3 $R^{b1}$, $C_{2-10}$ alkenylene-Q substituted with 0–3 $R^{b1}$, $C_{2-10}$ alkynylene-Q substituted with 0–3 $R^{b1}$, $(CR^aR^{a1})_{r1}O$ $(CR^aR^{a1})_r$-Q, $(CR^aR^{a1})_{r1}NR^a(CR^aR^{a1})_r$-Q, $(CR^aR^{a1})_{r1}C$ $(O)(CR^aR^{a1})_r$-Q, $(CR^aR^{a1})_{r1}C(O)O(CR^aR^{a1})_r$-Q, $(CR^aR^{a1})_{r1}OC(O)(CR^aR^{a1})_r$-Q, $(CR^aR^{a1})_{r1}C(O)NR^aR^{a1}$ $(CR^aR^{a1})_{r1}C(O)NR^a(CR^aR^{a1})_r$-Q, $(CR^aR^{a1})_{r1}OC(O)$ $(CR^aR^{a1})_r$-Q, $(CR^{a1})_{r1}OC(O)NR^a(CR^aR^{a1})_r$-Q, $(CR^aR^{a1})_{r1}OC(O)NR^a(CR^aR^{a1})_r$-Q, $(CR^aR^{a1})_{r1}NR^aC$ $(O)(CR^aa1)_r$-Q, $(CR^aR^{a1})_r$-Q, $(CR^aR^{a1})_{r1}SO_2NR^a(CR^aR^{a1})_r$-Q, $(CR^aR^{a1})_{r1}NR^aSO_2$ $(CR^aR^{a1})_r$-Q, and $(CR^aR^{a1})_{r1}$ $NR^aSO_2NR^a(CR^aR^{a1})_r$-Q;

$R^{2b}$ is H or $C_{1-6}$ alkyl;

Q is selected from H, a $C_{3-13}$ carbocycle substituted with 0–5 $R^d$ and a 5–14 membered heterocycle consisting of: carbon atoms and 1–4 heteroatoms selected from the group consisting of N, O, and S and substituted with 0–5 $R^d$;

$R^3$ is selected from $Q^1$, $C_{1-6}$ alkylene-$Q^1$, $C_{2-6}$ alkenylene-$Q^1$, $C_{2-6}$ alkynylene-$Q^1$, $(CR^aR^{a1})_{r1}O(CH_2)_r$-$Q^1$, $(CR^aR^{a1})_{r1}NR^a(CR^aR^{a1})_r$-$Q^1$, $(CR^aR^{a1})_{r1}NR^aC(O)(CR^aR^{a1})_r$-$Q^1$, $(CR^aR^{a1})_{r1}C(O)NR^a(CR^aR^{a1})_r$-$Q^1$, $(CR^aR^{a1})_{r1}C(O)(CR^aR^{a1})_r$-$Q^1$, $(CR^aR^{a1})_{r1}C(O)O(CR^aR^{a1})_r$-$Q^1$, $(CR^aR^{a1})_{r1}S(O)_p(CR^aR^{a1})_r$-$Q^1$, and $(CR^aR^{a1})_{r1}SO_2NR^a(CR^aR^{a1})_r$-$Q^1$;

alternatively, $R^2$ and $R^3$, when attached to adjacent atoms, combine with the adjacent atoms to form a 5–7 membered carbocycle substituted with 0–2 $R^b$ or a 5–7 membered heterocycle consisting of: carbon atoms and 1–4 heteroatoms selected from the group consisting of N, O, and S and substituted with 0–1 $R^{b1}$ $Q^1$ is selected from H, phenyl substituted with 0–3 $R^d$, naphthyl substituted with 0–3 $R^d$ and a 5–10 membered heteroaryl consisting of: carbon atoms and 1–4 heteroatoms selected from the group consisting of N, O, and S and substituted with 0–3 $R^d$;

$R^4$ is selected from $Q^2$, $C_{1-6}$ alkylene-$Q^2$, $C_{2-6}$ alkenylene-$Q^2$, $C_{2-6}$ alkynylene-$Q^2$, $(CR^aR^{a1})_{r1}O(CH_2)_r$-$Q^2$, $(CR^aR^{a1})_{r1}NR^a(CR^aR^{a1})_r$-$Q^2$, $(CR^aR^{a1})_{r1}NR^aC(O)(CR^aR^{a1})_r$-$Q^2$, $(CR^aR^{a1})_{r1}C(O)NR^a(CR^aR^{a1})_r$-$Q^2$, $(CR^aR^{a1})_{r1}C(O)(CR^aR^{a1})_r$-$Q^2$, $(CR^aR^{a1}))_{r1}C(O)O(CR^aR^{a1})_r$-$Q^2$, $(CR^aR^{a1}{}_2)_{r1}S(O)_p(CR^aR^{a1})_r$-$Q^2$, and $(CR^aR^{a1})_{r1}SO_2NR^a(CR^aR^{a1})_r$-$Q^2$;

$Q^2$ is selected from H, phenyl substituted with 0–3 $R^d$, naphthyl substituted with 0–3 $R^d$, and a 5–10 membered heteroaryl consisting of: carbon atoms and 1–4 heteroatoms selected from the group consisting of N, O, and S and substituted with 0–3 $R^d$;

$R^a$, at each occurrence, is independently selected from H, $C_{1-4}$ alkyl, phenyl, and benzyl;

$R^{a1}$, at each occurrence, is independently selected from H and $C_{1-4}$ alkyl;

alternatively, $R^a$ and $R^{a1}$ when attached to a nitrogen are taken together with the nitrogen to which they are attached to form a 5 or 6 membered ring consisting of carbon atoms and from 0–1 additional heteroatoms selected from the group consisting of N, O, and S;

$R^{a2}$, at each occurrence, is independently selected from $C_{1-4}$ alkyl, phenyl, and benzyl;

$R^b$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)O$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, and $CF_2CF_3$;

$R^{b1}$, at each occurrence, is independently selected from $OR^a$, Cl, F, Br, I, =O, —CN, $NO_2$, and $NR^aR^{a1}$;

$R^c$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)O$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, $CF_2CF_3$, $C_{3-10}$ carbocycle substituted with 0–1 $R^{b1}$, and a 5–14 membered heterocycle consisting of: carbon atoms and 1–4 heteroatoms selected from the group consisting of N, O, and S and substituted with 0–1 $R^{b1}$;

$R^d$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)O$, $S(O)_2NR^aR^{a1}$, $NR^aS(O)_2R^{a2}$, $NR^aS(O)_2NR^aR^{a1}$, $OS(O)_2NR^aR^{a1}$, $NR^{a1}S(O)_2R^{a2}$, $S(O)_pR^{a2}$, $CF_3$, $CF_2CF_3$, $C_{3-10}$ carbocycle and a 5–14 membered heterocycle consisting of: carbon atoms and 1–4 heteroatoms selected from the group consisting of N, O, and S;

$R^5$, at each occurrence, is selected from $C_{1-10}$ alkyl substituted with 0–2 $R^b$, and $C_{1-8}$ alkyl substituted with 0–2 $R^e$;

$R^e$, at each occurrence, is selected from phenyl substituted with 0–2 $R^b$ and biphenyl substituted with 0–2 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$-$C_5$ alkyl)-1,3-dioxa-cyclopenten-2-one-yl] methyl, [5-($R^a$)-1,3-dioxa-cyclopenten-2-one-yl]methyl, (5-aryl-1,3-dioxa-cyclopenten-2-one-yl)methyl, —$C_{1-10}$ alkyl-$NR^7R^{7a}$, —$CH(R^8)OC(=O)R^9$, and —$CH(R^8)OC(=O)OR^9$;

$R^7$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-8}$ alkyl substituted with 1–2 $R^f$, $C_{3-8}$ cycloalkyl substituted with 1–2 $R^f$, and phenyl substituted with 0–2 $R^b$;

$R^f$, at each occurrence, is selected from $C_{1-4}$ alkyl, $C_{3-8}$ cycloalkyl, $C_{1-5}$ alkoxy, and phenyl substituted with 0–2 $R^{b1}$ p, at each occurrence, is selected from 0, 1, and 2;
q, at each occurrence, is selected from 0, 1, and 2;
r, at each occurrence, is selected from 0, 1, 2, 3, and 4; and,
r1, at each occurrence, is selected from 0, 1, 2, 3, and 4.

[2] In a preferred embodiment, the present invention provides a novel compound of formula IIa or IIb:

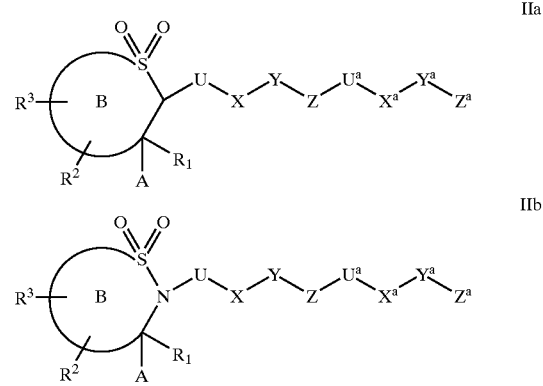

or a stereoisomer or pharmaceutically acceptable salt form thereof, wherein;

A is selected from —$CO_2H$, $CH_2CO_2H$, —CONHOH, —$CONHOR^5$, —$CONHOR^6$, —N(OH)$COR^5$, —SH, and —$CH_2SH$;

for formula IIa, ring B, including the $SO_2$, is a 5–7 membered non-aromatic heterocycle consisting of: $SO_2$, carbon atoms, 0–1 carbonyl groups, 0–1 double bonds, and 0–2 additional ring heteroatoms selected from O, N, $NR^2$, and $S(O)_p$, provided that if ring B has two additional ring heteroatoms then at least one of them is N or $NR^2$, and provided that ring B has other than a S—S, S—O, S—N, or N—O bond;

for formula IIb, ring B, including the $SO_2$ and N, is a 5–7 membered non-aromatic heterocycle consisting of: $SO_2$, N, carbon atoms, 0–1 carbonyl groups, 0–1 double bonds, and 0–1 additional ring heteroatoms selected from O, N, $NR^2$, and $S(O)_p$, provided that ring B has other than a S—S, S—O, S—N, or N—O bond;

U is absent or is selected from: O, $NR^{a1}$, C(O), C(O)O, OC(O), $C(O)NR^{a1}$, and $NR^{a1}C(O)$;

X is absent or selected from $C_{1-4}$ alkylene, $C_{2-4}$ alkenylene, and $C_{2-4}$ alkynylene;

Y is absent or is selected from: O, $NR^{a1}$, C(O), C(O)O, OC(O), $C(O)NR^{a1}$, and $NR^{a1}C(O)$;

Z is absent or selected from a $C_{3-6}$ carbocycle substituted with 0–4 $R^b$ and a 5–6 membered heterocycle consisting of: carbon atoms and 1–4 heteroatoms selected from the group consisting of N, O, and S and substituted with 0–3 $R^b$;

$U^a$ is absent or is selected from: O, $NR^{a1}$, C(O), C(O)O, $C(O)NR^{a1}$, $NR^{a1}C(O)$, $S(O)_p$, and $S(O)_pNR^{a1}$;

$X^a$ is absent or is $C_{1-4}$ alkylene;

$Y^a$ is absent or selected from O and $NR^{a1}$;

$Z^a$ is selected from a $C_{3-10}$ carbocycle substituted with 0–5 $R^c$ and a 5–10 membered heterocycle consisting of: carbon atoms and 1–4 heteroatoms selected from the group consisting of N, O, and S and substituted with 0–5 $R^c$;

provided that when U-X—Y are $CH_2$, $U^a$-$X^a$—$Y^a$ are absent, and Z is phenyl, then $Z^a$ is other than a 2-substituted phenyl ring or a 3,5-disubstituted phenyl ring;

provided that U, X, Y, Z, $U^a$, $X^a$, $Y^a$, $Z^a$, combine to form other than a N—N, N—O, O—N, O—O, $S(O)_p$—O, O—$S(O)_p$ or $S(O)_p$—$S(O)_p$ group, an unsubstituted naphthyl, a substituted naphthyl wherein the substituent is 1–3 atoms in length, an unsubstituted phenyl, a substituted phenyl wherein the substituent is 1–3 atoms in length, an unsubstituted benzyl, or a substituted benzyl wherein the substituent is 1–3 atoms in length;

$R^1$ is selected from H, $C_{1-4}$ alkyl, phenyl, and benzyl;

$R^2$ is selected from Q, $C_{1-6}$ alkylene-Q, $C_{2-6}$ alkenylene-Q, $C_{2-6}$ alkynylene-Q, $(CR^aR^{a1})_{r1}O(CR^aR^{a1})_r$-Q, $(CR^a-R^{a1})_{r1}NR^a(CR^aR^{a1})_r$-Q, $(CR^aR^{a1})_{r1}C(O)(CR^aR^{a1})_r$-Q, $(CR^aR^{a1})_{r1}C(O)O(CR^aR^{a1})_r$-Q, $(CR^aR^{a1})_{r1}C(O)NR^aR^{a1}$, $(CR^aR^{a1})_{r1}C(O)NR^a(CR^aR^{a1})_r$-Q, $(CR^aR^{a1})_{r1}S(O)_p(CR^aR^{a1})_r$-Q, and $(CR^aR^{a1})_{r1}SO_2NR^a(CR^aR^{a1})_r$-Q;

$R^3$ is selected from $Q^1$, $C_{1-6}$ alkylene-$Q^1$, $C_{2-6}$ alkenylene-$Q^1$, $C_{2-6}$ alkynylene-$Q^1$, $(CR^aR^{a1}))_{r1}O(CH_2)_r$-$Q^1$, $(CR^aR^{a1})_{r1}NR^a(CR^aR^{a1})_r$-$Q^1$, $(CR^aR^{a1}))_{r1}NR^aC(O)(CR^aR^{a1})_r$-$Q^1$, $(CR^aR^{a1})_{r1}C(O)NR^a(CR^aR^{a1})_r$-$Q^1$, $(CR^aR^{a1})_{r1}C(O)(CR^aR^{a1})_r$-$Q^1$, $(CR^aR^{a1})_{r1}C(O)O(CR^aR^{a1})_r$-$Q^1$, $(CR^aR^{a1})_{r1}S(O)_p(CR^aR^{a1})_r$-$Q^1$, and $(CR^aR^{a1})_{r1}SO_2NR^a(CR^aR^{a1})_r$-$Q^1$;

alternatively, $R^2$ and $R^3$, when attached to adjacent atoms, combine with the adjacent atoms to form a 5–6 membered carbocycle substituted with 0–2 $R^b$ or a 5–6 membered heterocycle consisting of: carbon atoms and 1–2 heteroatoms selected from the group consisting of N, O, and S and substituted with 0–1 $R^b$;

Q is selected from H, a $C_{3-6}$ carbocycle substituted with 0–5 $R^d$, and a 5–10 membered heterocycle consisting of: carbon atoms and 1–4 heteroatoms selected from the group consisting of N, O, and S and substituted with 0–5 $R^d$;

$Q^1$ is selected from H, phenyl substituted with 0–3 $R^d$, and a 5–6 membered heteroaryl consisting of: carbon atoms and 1–4 heteroatoms selected from the group consisting of N, O, and S and substituted with 0–3 $R^d$;

$R^4$ is selected from $Q^2$, $C_{1-6}$ alkylene-$Q^2$, $C_{2-6}$ alkenylene-$Q^2$, $(CR^aR^{a1})_{r1}O(CH_2)_r$-$Q^2$, $(CR^aR^{a1})_{r1}NR^a(CR^aR^{a1})_r$-$Q^2$, $(CR^aR^{a1})_{r1}NR^aC(O)(CR^aR^{a1})_r$-$Q^2$, $(CR^aR^{a1})_{r1}C(O)NR^a(CR^aR^{a1})_r$-$Q^2$, $(CR^aR^{a1})_{r1}C(O)(CR^aR^{a1})_r$-$Q^2$, $(CR^aR^{a1})_{r1}S(O)_p(CR^aR^{a1})_r$-$Q^2$, and $(CR^aR^{a1})_{r1}SO_2NR^a(CR^aR^{a1})_r$-$Q^2$;

$Q^2$ is selected from H, phenyl substituted with 0–3 $R^d$, and a 5–6 membered heteroaryl consisting of: carbon atoms and 1–4 heteroatoms selected from the group consisting of N, O, and S and substituted with 0–3 $R^d$;

$R^a$, at each occurrence, is independently selected from H, $C_{1-4}$ alkyl, phenyl, and benzyl;

$R^{a1}$, at each occurrence, is independently selected from H and $C_{1-4}$ alkyl;

alternatively, $R^a$ and $R^{a1}$ when attached to a nitrogen are taken together with the nitrogen to which they are attached to form a 5 or 6 membered ring consisting of: carbon atoms and from 0–1 additional heteroatoms selected from the group consisting of N, O, and S;

$R^{a2}$, at each occurrence, is independently selected from $C_{1-4}$ alkyl, phenyl, and benzyl;

$R^b$, at each occurrence, is independently selected from $C_{1-6}$ alkyl, $OR^a$, Cl, F, Br, =O, —CN, $NR^aR^{a1}$, $C(O)R^a$, $C(O)OR^a$, $C(O)NR^aR^{a1}$, $S(O)_2NR^aR^{a1}$, $S(O)_pR^{a2}$, and $CF_3$;

$R^c$, at each occurrence, is independently selected from $C_{1-6}$ alkyl, $OR^a$, Cl, F, Br, =O, —CN, $NO_2$, $NR^aR^{a1}$, $C(O)R^a$, $C(O)OR^a$, $C(O)NR^aR^{a1}$, $S(O)_2NR^aR^{a1}$, $S(O)_pR^{a2}$, $CF_3$, $C_{3-6}$ carbocycle, and a 5–6 membered heterocycle consisting of: carbon atoms and 1–4 heteroatoms selected from the group consisting of N, O, and S;

$R^d$, at each occurrence, is independently selected from $C_{1-6}$ alkyl, $OR^a$, Cl, F, Br, =O, —CN, $NR^aR^{a1}$, $C(O)R^a$, $C(O)OR^a$, $C(O)NR^aR^{a1}$, $S(O)_2NR^aR^{a1}$, $S(O)_pR^{a2}$, $CF_3$, $C_{3-6}$ carbocycle, and a 5–6 membered heterocycle consisting of: carbon atoms and 1–4 heteroatoms selected from the group consisting of N, O, and S;

$R^5$, at each occurrence, is selected from $C_{1-6}$ alkyl substituted with 0–2 $R^b$, and $C_{1-4}$ alkyl substituted with 0–2 $R^e$;

$R^e$, at each occurrence, is selected from phenyl substituted with 0–2 $R^b$, and biphenyl substituted with 0–2 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$-$C_5$ alkyl)-1,3-dioxa-cyclopenten-2-one-yl]methyl, [5-($R^a$)-1,3-dioxa-cyclopenten-2-one-yl]methyl, (5-aryl-1,3-dioxa-cyclopenten-2-one-yl)methyl, —$C_{1-10}$ alkyl-$NR^7R^{7a}$, —CH($R^8$)OC(=O)$R^9$, and —CH($R^8$)OC(=O)$OR^9$;

$R^7$ is selected from H and $C_{1-6}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-6}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-6}$ alkyl substituted with 1–2 $R^f$, $C_{3-6}$ cycloalkyl substituted with 1–2 $R^f$, and phenyl substituted with 0–2 $R^b$;

$R^f$, at each occurrence, is selected from $C_{1-4}$ alkyl, $C_{3-6}$ cycloalkyl, $C_{1-5}$ alkoxy, and phenyl substituted with 0–2 $R^b$;

p, at each occurrence, is selected from 0, 1, and 2;

r, at each occurrence, is selected from 0, 1, 2, 3, and 4; and, r1, at each occurrence, is selected from 0, 1, 2, 3, and 4.

[3] In another preferred embodiment, the present invention provides a novel compound of formula

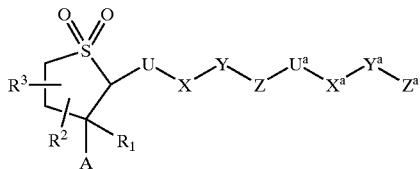
IIIa

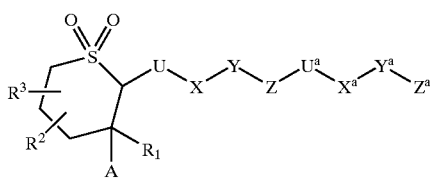
IIIb

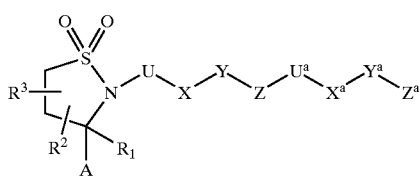
IIIc

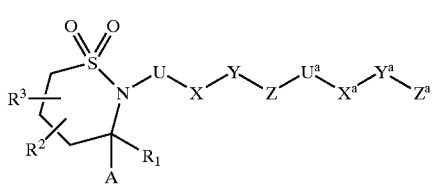
IIId

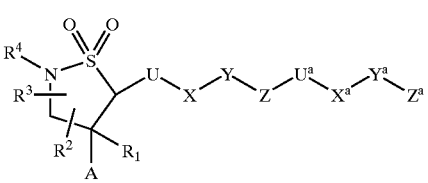
IIIe

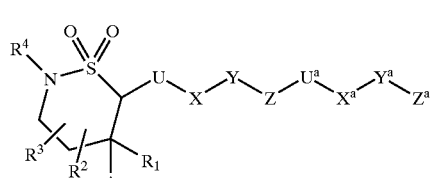
IIIf

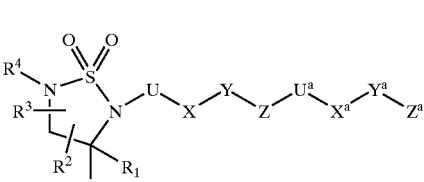
IIIg

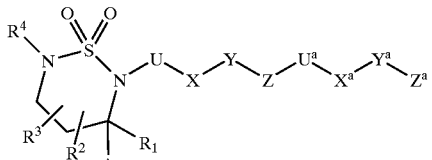
IIIh or a stereoisomer or pharmaceutically acceptable salt form thereof, wherein;

A is selected from —$CO_2H$, $CH_2CO_2H$, —CONHOH, —CONHOR$^5$, and N(OH)COR$^5$;

U is absent or is selected from: O, NR$^{a1}$, and C(O);

X is absent or is $C_{1-4}$ alkylene;

Y is absent or is selected from: O and NR$^{a1}$;

Z is absent or selected from a $C_{5-6}$ carbocycle substituted with 0–3 R$^b$ and a 5–6 membered heteroaryl consisting of: carbon atoms and from 1–4 heteroatoms selected from the group consisting of N, O, and S and substituted with 0–3 R$^b$ U$^a$ is absent or is selected from: O, NR$^{a1}$, C(O) C(O)NR$^{a1}$, S(O)$_p$, and S(O)$_p$NR$^{a1}$;

X$^a$ is absent or is $C_{1-2}$ alkylene;

Y$^a$ is absent or selected from O and NR$^{a1}$;

Z$^a$ is selected from a $C_{5-6}$ carbocycle substituted with 0–3 R$^c$ and a 5–10 membered heteroaryl consisting of: carbon atoms and from 1–4 heteroatoms selected from the group consisting of N, O, and S and substituted with 0–3 R$^c$;

provided that when U-X—Y are $CH_2$, U$^a$-X$^a$—Y$^a$ are absent, and Z is phenyl, then Z$^a$ is other than a 2-substituted phenyl ring or a 3,5-disubstituted phenyl ring;

provided that U, X, Y, Z, U$^a$, X$^a$, Y$^a$, Z$^a$, combine to form other than a N—N, N—O, O—N, O—O, S(O)$_p$—O, O—S(O)$_p$ or S(o)$_p$—S(O)$_p$ group, an unsubstituted naphthyl, a substituted naphthyl wherein the substituent is 1–3 atoms in length, an unsubstituted phenyl, a substituted phenyl wherein the substituent is 1–3 atoms in length, an unsubstituted benzyl, or a substituted benzyl wherein the substituent is 1–3 atoms in length;

R$^1$ is selected from H, $C_{1-4}$ alkyl, phenyl, and benzyl;

R$^2$ is selected from Q, $C_{1-6}$ alkylene-Q, $C_{2-6}$ alkenylene-Q, $C_{2-6}$ alkynylene-Q, (CR$^a$R$^{a1}$)$_{r1}$O(CR$^a$R$^{a1}$)$_r$-Q, (CR$^a$R$^{a1}$)$_{r1}$NR$^a$(CR$^a$R$^{a1}$)$_r$-Q, (CR$^a$R$^{a1}$)$_{r1}$C(O)(CR$^a$R$^{a1}$)$_r$-Q, (CR$^a$R$^{a1}$)$_{r1}$C(O)O(CR$^a$R$^{a1}$)$_r$-Q, (CR$^a$R$^{a2}$)$_{r1}$C(O)NR$^a$R$^{a1}$, (CR$^a$R$^{a2}$)$_{r1}$C(O)NR$^a$(CR$^a$R$^{a1}$)$_r$-Q, and (CR$^a$R$^{a1}$)$_{r1}$S(O)$_p$(CR$^a$R$^{a1}$)$_r$-Q;

Q is selected from H, a $C_{3-6}$ carbocycle substituted with 0–3 R$^d$, and a 5–10 membered heterocycle consisting of: carbon atoms and 1–4 heteroatoms selected from the group consisting of N, O, and S and substituted with 0–3 R$^d$;

R$^3$ is selected from Q$^1$, $C_{1-6}$ alkylene-Q$^1$, (CR$^a$R$^{a1}$)$_{r1}$O(CH$_2$)$_r$-Q$^1$, (CR$^a$R$^{a1}$)$_{r1}$NR$^a$(CR$^a$R$^{a1}$)$_r$-Q$^1$, (CR$^a$R$^{a1}$)$_{r1}$C(O)NR$^a$(CR$^a$R$^{a1}$)$_r$-Q$^1$, (CR$^a$R$^{a1}$)$_{r1}$C(O)(CR$^a$R$^{a1}$)$_r$-Q$^1$, and (CR$^a$R$^{a1}$)$_{r1}$SO$_2$NR$^a$(CR$^a$R$^{a1}$)$_r$-Q$^1$;

Q$^1$ is selected from H, phenyl substituted with 0–2 R$^d$, and a 5–6 membered heteroaryl consisting of: carbon atoms and 1–3 heteroatoms selected from the group consisting of N, O, and S and substituted with 0–2 R$^d$;

R$^4$ is selected from Q$^2$, $C_{1-6}$ alkylene-Q$^2$, (CR$^a$R$^{a1}$)$_{r1}$(CH$_2$)$_r$-Q$^2$, (CR$^a$R$^{a1}$)$_{r1}$NR$^a$(CR$^a$R$^{a1}$)$_r$-Q$^2$, (CR$^a$R$^{a1}$)$_{r1}$C(O)NR$^a$(CR$^a$R$^{a1}$)$_r$-Q$^2$, (CR$^a$R$^{a1}$)$_{r1}$C(O)(CR$^a$R$^{a1}$)$_r$-Q$^2$, and (CR$^a$R$^{a1}$)$_{r1}$SO$_2$NR$^a$(CR$^a$R$^{a1}$)$_r$-Q$^2$;

$Q^2$ is selected from H, phenyl substituted with 0–2 $R^d$, and a 5–6 membered heteroaryl consisting of: carbon atoms and 1–3 heteroatoms selected from the group consisting of N, O, and S and substituted with 0–2 $R^d$;

$R^a$, at each occurrence, is independently selected from H, $C_{1-4}$ alkyl, phenyl, and benzyl;

$R^{a1}$, at each occurrence, is independently selected from H and $C_{1-4}$ alkyl;

$R^{a2}$, at each occurrence, is independently selected from $C_{1-4}$ alkyl, phenyl, and benzyl;

$R^b$, at each occurrence, is independently selected from $C_{1-4}$ alkyl, $OR^a$, Cl, F, =O, $NR^aR^{a1}$, $C(O)R^a$, $C(O)OR^a$, $C(O)NR^aR^{a1}$, $S(O)_2NR^aR^{a1}$, $S(O)R^{a2}$, and $CF_3$;

$R^c$, at each occurrence, is independently selected from $C_{1-6}$ alkyl, $OR^a$, Cl, F, Br, =O, $NO_2$, $NR^aR^{a1}$, $C(O)R^a$, $C(O)NR^aR^{a1}$, $S(O)_2NR^aR^{a1}$, $S(O)_pR^{a2}$, and $CF_3$;

$R^d$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, $CF_3$, and phenyl;

$R^5$, at each occurrence, is selected from $C_{1-4}$ alkyl substituted with 0–2 $R^b$ and $C_{1-4}$ alkyl substituted with 0–2 $R^e$;

$R^e$, at each occurrence, is selected from phenyl substituted with 0–2 $R^b$ and biphenyl substituted with 0–2 $R^b$;

p, at each occurrence, is selected from 0, 1, and 2;

r, at each occurrence, is selected from 0, 1, 2, 3, and 4; and, r1, at each occurrence, is selected from 0, 1, 2, 3, and 4.

[4] In another preferred embodiment, the present invention provides a novel compound wherein:

U is absent;

X is absent or is selected from $CH_2$ and $CH_2CH_2$;

Y is absent;

Z is absent or selected from phenyl substituted with 0–3 $R^b$ and pyridyl substituted with 0–3 $R^b$;

$U^a$ is absent or is O;

$X^a$ is absent or is $CH_2$ or $CH_2CH_2$;

$Y^a$ is absent or is O;

$Z^a$ is selected from phenyl substituted with 0–3 $R^c$, pyridyl substituted with 0–3 $R^c$, thienyl substituted with 0–3 $R^c$, furanyl substituted with 0–3 $R^c$, and quinolinyl substituted with 0–3 $R^c$;

provided that when U-X—Y are $CH_2$, $U^a$-$X^a$—$Y^a$ are absent, and Z is phenyl, then $Z^a$ is other than a 2-substituted phenyl ring or a 3,5-disubstituted phenyl ring;

provided that U, X, Y, Z, $U^a$, $X^a$, $Y^a$, $Z^a$, combine to form other than a N—N, N—O, O—N, O—O, $S(O)_p$—O, O—$S(O)_p$ or $S(O)_p$—$S(O)_p$ group, an unsubstituted naphthyl, a substituted naphthyl wherein the substituent is 1–3 atoms in length, an unsubstituted phenyl, a substituted phenyl wherein the substituent is 1–3 atoms in length, an unsubstituted benzyl, or a substituted benzyl wherein the substituent is 1–3 atoms in length;

$R^1$ is selected from H, $CH_3$, and $CH_2CH_3$;

$R^2$ is selected from Q, $C_{1-6}$ alkylene-Q, $(CR^aR^{a1})_{r1}O(CR^aR^{a1})_r$-Q, $(CR^aR^{a1})_{r1}NR^a(CR^aR^{a1})_r$-Q, $C(O)(CR^aR^{a1})_r$-Q, $C(O)O(CR^aR^{a1})_r$-Q, $C(O)NR^a(CR^aR^{a1})_r$-Q, and $S(O)_p(CR^aR^{a1})_r$-Q;

Q is selected from H, cyclopropyl substituted with 0–1 $R^d$, cyclobutyl substituted with 0–1 $R^d$, cyclopentyl substituted with 0–1 $R^d$, cyclohexyl substituted with 0–1 $R^d$, phenyl substituted with 0–2 $R^d$, and a heteroaryl substituted with 0–3 $R^d$, wherein the heteroaryl is selected from pyridyl, quinolinyl, thiazolyl, furanyl, imidazolyl, and isoxazolyl;

$R^3$ is selected from $Q^1$, $C_{1-4}$ alkylene-$Q^1$, $(CH_2)_{r1}O(CH_2)_r$-$Q^1$, $(CH_2)_{r1}NR^a(CH_2)_r$-$Q^1$, $(CH_2)_{r1}C(O)NR^a(CH_2)_r$-$Q^1$, $(CH_2)_{r1}C(O)(CH_2)_r$-$Q^1$, and $(CH_2)_{r1}SO_2NR^a(CH_2)_r$-$Q^1$;

$Q^1$ is selected from H, phenyl substituted with 0–2 $R^d$, and a heteroaryl substituted with 0–2 $R^d$, wherein the heteroaryl is selected from pyridyl, thiazolyl, furanyl, imidazolyl, and isoxazolyl;

$R^4$ is selected from H and $C_{1-4}$ alkyl;

$R^a$, at each occurrence, is independently selected from H, $CH_3$, and $CH_2CH_3$;

$R^{a1}$, at each occurrence, is independently selected from H, $CH_3$, and $CH_2CH_3$;

$R^{a2}$, at each occurrence, is independently selected from H, $CH_3$, and $CH_2CH_3$;

$R^b$, at each occurrence, is independently selected from $C_{1-4}$ alkyl, $OR^a$, Cl, F, =O, $NR^aR^{a1}$, $C(O)R^a$, $C(O)OR^a$, $C(O)NR^aR^{a1}$, $S(O)_2NR^aR^{a1}$, $S(O)_pR^{a2}$, and $CF_3$;

$R^c$, at each occurrence, is independently selected from $C_{1-6}$ alkyl, $OR^a$, Cl, F, Br, =O, $NO_2$, $NR^aR^{a1}$, $C(O)R^a$, $C(O)NR^aR^{a1}$, $S(O)_2NR^aR^{a1}$, $S(O)_pR^{a2}$, and $CF_3$;

$R^d$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, $CF_3$, and phenyl;

p, at each occurrence, is selected from 0, 1, and 2;

r, at each occurrence, is selected from 0, 1, 2, and 3; and, r1, at each occurrence, is selected from 0, 1, 2, and 3.

[5] In a more preferred embodiment, the present invention provides a novel compound of formula IVa–h

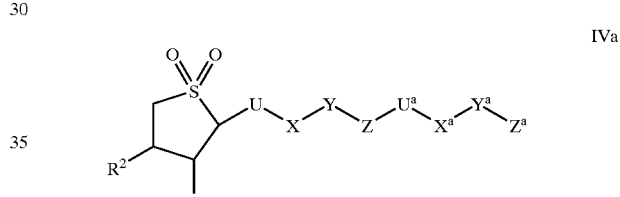

IVa

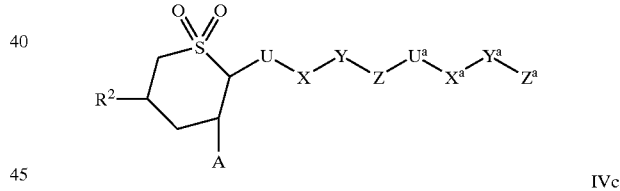

IVb

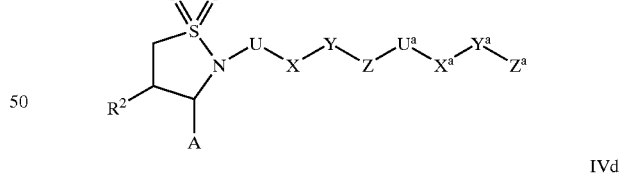

IVc

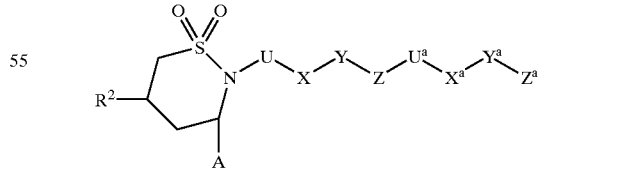

IVd

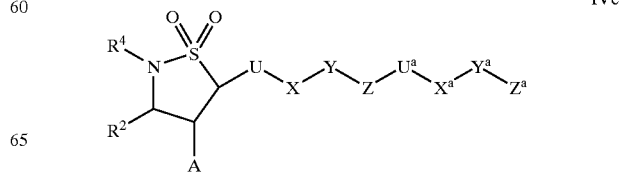

IVe

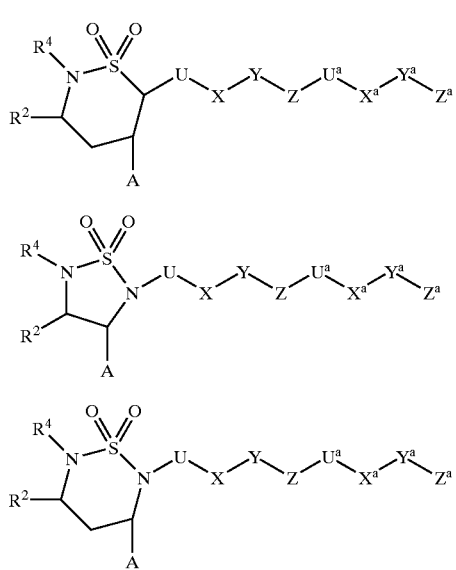

U is absent;
X is absent or is selected from CH$_2$ and CH$_2$CH$_2$;
Y is absent;
Z is phenyl;
U$^a$ is absent or is O;
X$^a$ is absent or is CH$_2$;
Y$^a$ is absent;
Z$^a$ is selected from phenyl substituted with 0–2 R$^c$, pyridyl substituted with 0–1 R$^c$, and quinolinyl substituted with 0–2 R$^c$;
provided that when U-X—Y are CH$_2$ and U$^a$-X$^a$—Y$^a$ are absent, then Z$^a$ is other than a 2-substituted phenyl ring or a 3,5-disubstituted phenyl ring;
R$^2$ is selected from O-Q, CH$_2$O-Q, O(CR$^a$R$^{a1}$)-Q, CH$_2$O (CR$^a$R$^{a1}$)-Q, O(CR$^a$R$^{a1}$)(CR$^a$R$^{a1}$)-Q, CH$_2$O(CR$^a$R$^{a1}$) (CR$^a$R$^{a1}$)-Q, NR$^a$-Q, CH$_2$NR$^a$-Q, NR$^a$(CR$^a$R$^{a1}$)-Q, CH$_2$NR$^a$(CR$^a$R$^{a1}$)-Q, NR$^a$(CR$^a$R$^{a1}$)(CR$^a$R$^{a1}$)-Q, and CH$_2$NR$^a$(CR$^a$R$^{a1}$)(CR$^a$R$^{a1}$)-Q;
Q is selected from H, cyclopropyl substituted with 0–1 R$^d$, cyclobutyl substituted with 0–1 R$^d$, cyclopentyl substituted with 0–1 R$^d$, cyclohexyl substituted with 0–1 R$^d$, phenyl substituted with 0–2 R$^d$, and a heteroaryl substituted with 0–3 R$^d$, wherein the heteroaryl is selected from pyridyl, quinolinyl, thiazolyl, furanyl, imidazolyl, and isoxazolyl;
R$^a$ is independently selected from H, CH$_3$, and CH$_2$CH$_3$;
R$^c$, at each occurrence, is independently selected from CH$_3$, C(CH$_3$)$_3$, OCH$_3$, Cl, F, NO$_2$, NH$_2$, C(O)H, SCH$_3$, S(O)$_2$CH$_3$, and CF$_3$;
R$^d$, at each occurrence, is independently selected from C$_{1-6}$ alkyl, OR$^a$, Cl, F, Br, =O, NR$^a$R$^{a1}$, C(O)R$^a$, C(O)NR$^a$R$^{a1}$, S(O)$_2$NR$^a$R$^{a1}$, S(O)$_p$R$^{a2}$, CF$_3$, and phenyl; and,
p, at each occurrence, is selected from 0, 1, and 2;
r, at each occurrence, is selected from 0, 1, and 2; and,
r1, at each occurrence, is selected from 0, 1, and 2.

In another preferred embodiment, the present invention provides a novel compound, wherein:
U is absent or is selected from: O, NR$^{a1}$, C(O), C(O)O, OC(O), C(O)NR$^{a1}$, and NR$^{a1}$C(O);
X is absent or selected from C$_{1-4}$ alkylene, C$_{2-4}$ alkenylene, and C$_{2-4}$ alkynylene; and,
Y is absent or is selected from: O, NR$^{a1}$, C(O), C(O)O, OC(O), C(O)NR$^{a1}$, and NR$^{a1}$C(O).

In another preferred embodiment, the present invention provides a novel compound, wherein:
U is absent or is selected from: O, NR$^{a1}$, and C(O);
X is absent or is C$_{1-4}$ alkylene; and,
Y is absent or is selected from: O and NR$^{a1}$.

In another preferred embodiment, the present invention provides a novel compound, wherein:
U is absent;
X is absent or is selected from CH$_2$ and CH$_2$CH$_2$; and,
Y is absent.

In another preferred embodiment, the present invention provides a novel compound, wherein:
Z is absent or selected from a C$_{3-6}$ carbocycle substituted with 0–4 R$^b$ and a 5–6 membered heterocycle consisting of: carbon atoms and 1–4 heteroatoms selected from the group consisting of N, O, and S and substituted with 0–3 R$^b$.

In another preferred embodiment, the present invention provides a novel compound, wherein:
Z is absent or selected from a C$_{5-6}$ carbocycle substituted with 0–3 R$^b$ and a 5–6 membered heteroaryl consisting of: carbon atoms and from 1–4 heteroatoms selected from the group consisting of N, O, and S and substituted with 0–3 R$^b$.

In another preferred embodiment, the present invention provides a novel compound, wherein:
Z is absent or selected from phenyl substituted with 0–3 R$^b$ and pyridyl substituted with 0–3 R$^b$.

In another preferred embodiment, the present invention provides a novel compound, wherein:
Z is phenyl.

In another preferred embodiment, the present invention provides a novel compound, wherein:
U$^a$ is absent or is selected from: O, NR$^{a1}$, C(O), C(O)O, C(O)NR$^{a1}$, NR$^{a1}$C(O), S(O)$_p$, and S(O)$_p$NR$^{a1}$;
X$^a$ is absent or is C$_{1-4}$ alkylene; and,
Y$^a$ is absent or selected from O and NR$^{a1}$.

In another preferred embodiment, the present invention provides a novel compound, wherein:
U$^a$ is absent or is selected from: O, NR$^{a1}$, C(O), C(O)NR$^{a1}$, S(O)$_p$, and S(O)$_p$NR$^{a1}$;
X$^a$ is absent or is C$_{1-2}$ alkylene; and,
Y$^a$ is absent or selected from O and NR$^{a1}$.

In another preferred embodiment, the present invention provides a novel compound, wherein:
U$^a$ is absent or is O;
X$^a$ is absent or is CH$_2$ or CH$_2$CH$_2$; and,
Y$^a$ is absent or is O.

In another preferred embodiment, the present invention provides a novel compound, wherein:
U$^a$ is absent or is O;
X$^a$ is absent or is CH$_2$; and,
Y$^a$ is absent.

In another preferred embodiment, the present invention provides a novel compound, wherein:
Z$^a$ is selected from a C$_{3-10}$ carbocycle substituted with 0–5 R$^c$ and a 5–10 membered heterocycle consisting of: carbon atoms and 1–4 heteroatoms selected from the group consisting of N, O, and S and substituted with 0–5 R$^c$;
provided that when U-X—Y are CH$_2$, U$^a$-X$^a$—Y$^a$ are absent, and Z is phenyl, then Z$^a$ is other than a 2-substituted phenyl ring or a 3,5-disubstituted phenyl ring.

In another preferred embodiment, the present invention provides a novel compound, wherein:
Z$^a$ is selected from a C$_{5-6}$ carbocycle substituted with 0–3 R$^c$ and a 5–10 membered heteroaryl consisting of: carbon atoms and from 1–4 heteroatoms selected from the group consisting of N, O, and S and substituted with 0–3 $R^c$;

provided that when U—X—Y are $CH_2$, $U^a$-$X^a$—$Y^a$ are absent, and Z is phenyl, then $Z^a$ is other than a 2-substituted phenyl ring or a 3,5-disubstituted phenyl ring.

In another preferred embodiment, the present invention provides a novel compound, wherein:

$Z^a$ is selected from phenyl substituted with 0–3 $R^c$, pyridyl substituted with 0–3 $R^c$, thienyl substituted with 0–3 $R^c$, furanyl substituted with 0–3 $R^c$, and quinolinyl substituted with 0–3 $R^c$;

provided that when U—X—Y are $CH_2$, $U^a$—$X^a$—$Y^a$ are absent, and Z is phenyl, then $Z^a$ is other than a 2-substituted phenyl ring or a 3,5-disubstituted phenyl ring.

In another preferred embodiment, the present invention provides a novel compound, wherein:

$Z^a$ is selected from phenyl substituted with 0–2 $R^c$, pyridyl substituted with 0–1 $R^c$, and quinolinyl substituted with 0–2 $R^c$;

provided that when U—X—Y are $CH_2$ and $U^a$—$X^a$—$Y^a$ are absent, then $Z^a$ is other than a 2-substituted phenyl ring or a 3,5-disubstituted phenyl ring.

In another preferred embodiment, the present invention provides a novel compound, wherein:

$R^1$ is selected from H, $C_{1-4}$ alkyl, phenyl, and benzyl;

$R^2$ is selected from Q, $C_{1-6}$ alkylene-Q, $C_{2-6}$ alkenylene-Q, $C_{2-6}$ alkynylene-Q, $(CR^aR^{a1})_{r1}O(CR^aR^{a1})_r$-Q, $(CR^a-R^{a1})_{r1}NR^a(CR^aR^{a1})_r$-Q, $(CR^aR^{a1})_{r1}C(O)(CR^aR^{a1})_r$-Q, $(CR^aR^{a1})_{r1}C(O)O(CR^aR^{a1})_r$-Q, $(CR^aR^{a1})_{r1}C(O)NR^aR^{a1}$, $(CR^aR^{a1})_{r1}C(O)NR^a(CR^aR^{a1})_r$-Q, $(CR^aR^{a1})_{r1}S(O)_p(CR^aR^{a1})_r$-Q, and $(CR^aR^{a1})_{r1}SO_2NR^a(CR^aR^{a1})_r$-Q;

$R^3$ is selected from $Q^1$, $C_{1-6}$ alkylene-$Q^1$, $C_{2-6}$ alkenylene-$Q^1$, $C_{2-6}$ alkynylene-$Q^1$, $(CR^aR^{a1})_{r1}O(CH_2)_r$-$Q^1$, $(CR^aR^{a1})_{r1}NR^a(CR^aR^{a1})_r$-$Q^1$, $(CR^aR^{a1})_{r1}NR^aC(O)(CR^aR^{a1})_r$-$Q^1$, $(CR^aR^{a1}))_{r1}C(O)NR^a(CR^aR^{a1})_r$-$Q^1$, $(CR^aR^{a1})_{r1}C(O)(CR^aR^{a1})_r$-$Q^1$, $(CR^aR^{a1})_{r1}C(O)(CR^aR^{a1})_r$-$Q^1$, $(CR^aR^{a1})_{r1}S(O)_p(CR^aR^{a1})_r$-$Q^1$, and $(CR^aR^{a1})_{r1}SO_2NR^a(CR^aR^{a1})_r$-$Q^1$;

alternatively, $R^2$ and $R^3$, when attached to adjacent atoms, combine with the adjacent atoms to form a 5–6 membered carbocycle substituted with 0–2 $R^b$ or a 5–6 membered heterocycle consisting of: carbon atoms and 1–2 heteroatoms selected from the group consisting of N, O, and S and substituted with 0–1 $R^b$;

Q is selected from H, a $C_{3-6}$ carbocycle substituted with 0–5 $R^d$, and a 5–10 membered heterocycle consisting of: carbon atoms and 1–4 heteroatoms selected from the group consisting of N, O, and S and substituted with 0–5 $R^d$;

$Q^1$ is selected from H, phenyl substituted with 0–3 $R^d$, and a 5–6 membered heteroaryl consisting of: carbon atoms and 1–4 heteroatoms selected from the group consisting of N, O, and S and substituted with 0–3 $R^d$;

$R^4$ is selected from $Q^2$, $C_{1-6}$ alkylene-$Q^2$, $C_{2-6}$ alkenylene-$Q^2$, $(CR^aR^{a1})_{r1}O(CH_2)_r$-$Q^2$, $(CR^aR^{a1})_{r1}NR^a(CR^aR^{a1})_r$-$Q^2$, $(CR^aR^{a1})_{r1}NR^aC(O)(CR^aR^{a1})_r$-$Q^2$, $(CR^aR^{a1}))_{r1}C(O)NR^a(CR^aR^{a1})_r$-$Q^2$, $(CR^aR^{a1})_{r1}C(O)(CR^aR^{a1})_r$-$Q^2$, $(CR^aR^{a1}_2)_{r1}S(O)_p(CR^aR^{a1})_r$-$Q^2$, and $(CR^aR^{a1})_{r1}SO_2NR^a(CR^aR^{a1})_r$-$Q^2$; and, $Q^2$ is selected from H, phenyl substituted with 0–3 $R^d$, and a 5–6 membered heteroaryl consisting of: carbon atoms and 1–4 heteroatoms selected from the group consisting of N, O, and S and substituted with 0–3 $R^d$.

In another preferred embodiment, the present invention provides a novel compound, wherein:

$R^1$ is selected from H, $C_{1-4}$ alkyl, phenyl, and benzyl;

$R^2$ is selected from Q, $C_{1-6}$ alkylene-Q, $C_{2-6}$ alkenylene-Q, $C_{2-6}$ alkynylene-Q, $(CR^aR^{a1})_{r1}O(CR^aR^{a1})_r$-Q, $(CR^a-R^{a1})_{r1}NR^a(CR^aR^{a1})_r$-Q, $(CR^aR^{a1})_{r1}C(O)(CR^aR^{a1})_r$-Q, $(CR^aR^{a1})_{r1}C(O)O(CR^aR^{a1})_r$-Q, $(CR^aR^{a2})_{r1}$ $C(O)NR^aR^{a1}$, $(CR^aR^{a2})_{r1}C(O)NR^a(CR^aR^{a1})_r$-Q, and $(CR^aR^{a1})_{r1}S(O)_p(CR^aR^{a1})_r$-Q;

Q is selected from H, a $C_{3-6}$ carbocycle substituted with 0–3 $R^d$, and a 5–10 membered heterocycle consisting of: carbon atoms and 1–4 heteroatoms selected from the group consisting of N, O, and S and substituted with 0–3 $R^d$;

$R^3$ is selected from $Q^1$, $C_{1-6}$ alkylene-$Q^1$, $(CR^aR^{a1})_{r1}O(CH_2)_r$-$Q^1$, $(CR^aR^{a1})_{r1}NR^a(CR^aR^{a1})_r$-$Q^1$, $(CR^aR^{a1})_{r1}C(O)NR^a(CR^aR^{a1})_r$-$Q^1$, $(CR^aR^{a1})_{r1}C(O)(CR^aR^{a1})_r$-$Q^1$, and $(CR^aR^{a1})_{r1}SO_2NR^a(CR^aR^{a1})_r$-$Q^1$;

$Q^1$ is selected from H, phenyl substituted with 0–2 $R^d$, and a 5–6 membered heteroaryl consisting of: carbon atoms and 1–3 heteroatoms selected from the group consisting of N, O, and S and substituted with 0–2 $R^d$;

$R^4$ is selected from $Q^2$, $C_{1-6}$ alkylene-$Q^2$, $(CR^aR^{a1})_{r1}O(CH_2)_r$-$Q^2$, $(CR^aR^{a1})_{r1}NR^a(CR^aR^{a1})_r$-$Q^2$, $(CR^aR^{a1})_{r1}C(O)NR^a(CR^aR^{a1})_r$-$Q^2$, $(CR^aR^{a1})_{r1}C(O)(CR^aR^{a1})_r$-$Q^2$, and $(CR^aR^{a1})_{r1}SO_2NR^a(CR^aR^{a1})_r$-$Q^2$; and, $Q^2$ is selected from H, phenyl substituted with 0–2 $R^d$, and a 5–6 membered heteroaryl consisting of: carbon atoms and 1–3 heteroatoms selected from the group consisting of N, O, and S and substituted with 0–2 $R^d$.

In another preferred embodiment, the present invention provides a novel compound, wherein:

$R^1$ is selected from H, $CH_3$, and $CH_2CH_3$;

$R^2$ is selected from Q, $C_{1-6}$ alkylene-Q, $(CR^aR^{a1})_{r1}O(CR^aR^{a1})_r$-Q, $(CR^aR^{a1})_{r1}NR^a(CR^aR^{a1})_r$-Q, $C(O)(CR^aR^{a1})_r$-Q, $C(O)O(CR^aR^{a1})_r$-Q, $C(O)NR^a(CR^aR^{a1})_r$-Q, and $S(O)_p(CR^aR^{a1})_r$-Q;

Q is selected from H, cyclopropyl substituted with 0–1 $R^d$, cyclobutyl substituted with 0–1 $R^d$, cyclopentyl substituted with 0–1 $R^d$, cyclohexyl substituted with 0–1 $R^d$, phenyl substituted with 0–2 $R^d$, and a heteroaryl substituted with 0–3 $R^d$, wherein the heteroaryl is selected from pyridyl, quinolinyl, thiazolyl, furanyl, imidazolyl, and isoxazolyl;

$R^3$ is selected from $Q^1$, $C_{1-4}$ alkylene-$Q^1$, $(CH_2)_{r1}O(CH_2)_r$-$Q^1$, $(CH_2)_{r1}NR^a(CH_2)_r$-$Q^1$, $(CH_2)_{r1}C(O)NR^a(CH_2)_r$-$Q^1$, $(CH_2)_{r1}C(O)(CH_2)_r$-$Q^1$, and $(CH_2)_{r1}SO_2NR^a(CH_2)_r$-$Q^1$;

$Q^1$ is selected from H, phenyl substituted with 0–2 $R^d$, and a heteroaryl substituted with 0–2 $R^d$, wherein the heteroaryl is selected from pyridyl, thiazolyl, furanyl, imidazolyl, and isoxazolyl; and, $R^4$ is selected from H and $C_{1-4}$ alkyl.

In another preferred embodiment, the present invention provides a novel compound, wherein:

$R^2$ is selected from O-Q, $CH_2$O-Q, $O(CR^aR^{a1})$-Q, $CH_2O(CR^aR^{a1})$-Q, $O(CR^aR^{a1})(CR^aR^{a1})$-Q, $CH_2O(CR^aR^{a1})(CR^aR^{a1})$-Q, $NR^a$-Q, $CH_2NR^a$-Q, $NR^a(CR^aR^{a1})$-Q, $CH_2NR^a(CR^aR^{a1}$-Q, $NR^a(CR^aR^{a1})(CR^aR^{a1})$-Q, and $CH_2NR^a(CR^aR^{a1})(CR^aR^{a1})_r$-Q;

Q is selected from H, cyclopropyl substituted with 0–1 $R^d$, cyclobutyl substituted with 0–1 $R^d$, cyclopentyl substituted with 0–1 $R^d$, cyclohexyl substituted with 0–1 $R^d$, phenyl substituted with 0–2 $R^d$, and a heteroaryl substituted with 0–3 $R^d$, wherein the heteroaryl is selected from pyridyl, quinolinyl, thiazolyl, furanyl, imidazolyl, and isoxazolyl.

In another preferred embodiment, the present invention provides a novel compound, wherein:

$R^a$, at each occurrence, is independently selected from H, $C_{1-4}$ alkyl, phenyl, and benzyl;

$R^{a1}$, at each occurrence, is independently selected from H and $C_{1-4}$ alkyl;

alternatively, $R^a$ and $R^{a1}$ when attached to a nitrogen are taken together with the nitrogen to which they are attached to form a 5 or 6 membered ring consisting of: carbon atoms and from 0–1 additional heteroatoms selected from the group consisting of N, O, and S;

$R^{a2}$, at each occurrence, is independently selected from $C_{1-4}$ alkyl, phenyl, and benzyl;

$R^b$, at each occurrence, is independently selected from $C_{1-6}$ alkyl, $OR^a$, Cl, F, Br, =O, —CN, $NR^aR^{a1}$, $C(O)R^a$, $C(O)OR^a$, $C(O)NR^aR^{a1}$, $S(O)_2NR^aR^{a1}$, $S(O)_pR^{a2}$, and $CF_3$;

$R^c$, at each occurrence, is independently selected from $C_{1-6}$ alkyl, $OR^a$, Cl, F, Br, =O, —CN, $NR^aR^{a1}$, $C(O)R^a$, $C(O)OR^a$, $C(O)NR^aR^{a1}$, $S(O)_2NR^aR^{a1}$, $S(O)_pR^{a2}$, $CF_3$, $C_{3-6}$ carbocycle, and a 5–6 membered heterocycle consisting of: carbon atoms and 1–4 heteroatoms selected from the group consisting of N, O, and S; and, $R^d$, at each occurrence, is independently selected from $C_{1-6}$ alkyl, $OR^a$, Cl, F, Br, =O, —CN, $NR^aR^{a1}$, $C(O)R^a$, $C(O)OR^a$, $C(O)NR^aR^{a1}$, $S(O)_2NR^aR^{a1}$, $S(O)_pR^{a2}$, $CF_3$, $C_{3-6}$ carbocycle, and a 5–6 membered heterocycle consisting of: carbon atoms and 1–4 heteroatoms selected from the group consisting of N, O, and S.

In another preferred embodiment, the present invention provides a novel compound, wherein:

$R^{a1}$ at each occurrence, is independently selected from H, $C_{1-4}$ alkyl, phenyl, and benzyl;

$R^{a1}$, at each occurrence, is independently selected from H and $C_{1-4}$ alkyl;

$R^{a2}$, at each occurrence, is independently selected from $C_{1-4}$ alkyl, phenyl, and benzyl;

$R^b$, at each occurrence, is independently selected from $C_{1-4}$ alkyl, $OR^a$, Cl, F, =O, $NR^aR^{a1}$, $C(O)R^a$, $C(O)OR^a$, $C(O)NR^aR^{a1}$, $S(O)_2NR^aR^{a1}$, $S(O)_pR^{a2}$, and $CF_3$;

$R^c$, at each occurrence, is independently selected from $C_{1-6}$ alkyl, $OR^a$, Cl, F, Br, =O, $NO_2$, $NR^aR^{a1}$, $C(O)R^a$, $C(O)NR^aR^{a1}$, $S(O)_2NR^aR^{a1}$, $S(O)_pR^{a2}$, and $CF_3$;

$R^d$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, $CF_3$, and phenyl.

In another preferred embodiment, the present invention provides a novel compound, wherein:

$R^a$, at each occurrence, is independently selected from H, $CH_3$, and $CH_2CH_3$;

$R^{a1}$, at each occurrence, is independently selected from H, $CH_3$, and $CH_2CH_3$;

$R^{a2}$ at each occurrence, is independently selected from H, $CH_3$, and $CH_2CH_3$;

$R^b$, at each occurrence, is independently selected from $C_{1-4}$ alkyl, $OR^a$, Cl, F, =O, $NR^aR^{a1}$, $C(O)R^a$, $C(O)OR^a$, $C(O)NR^aR^{a1}$, $S(O)_2NR^aR^{a1}$, $S(O)_pR^{a2}$, and $CF_3$;

$R^c$, at each occurrence, is independently selected from $C_{1-6}$ alkyl, $OR^a$, Cl, F, Br, =O, $NO_2$, $NR^aR^{a1}$, $C(O)R^a$, $C(O)NR^aR^{a1}$, $S(O)_2NR^aR^{a1}$, $S(O)_pR^{a2}$, and $CF_3$;

$R^d$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, $CF_3$, and phenyl.

In another preferred embodiment, the present invention provides a novel compound, wherein:

$R^a$ is independently selected from H, $CH_3$, and $CH_2CH_3$;

$R^c$, at each occurrence, is independently selected from $CH_3$, $C(CH_3)3$, $OCH_3$, Cl, F, $NO_2$, $NH_2$, $C(O)H$, $SCH_3$, $S(O)_2CH_3$, and $CF_3$;

$R^d$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, $CF_3$, and phenyl; and, p, at each occurrence, is selected from 0, 1, and 2.

[6] In another preferred embodiment, the present invention provides a compound selected from the group:

(R/S) 2-([1,1'-biphenyl]-4-ylmethyl)-N-hydroxy-3-isothiazolidinecarboxamide 1,1-dioxide;

(R/S) 2-(2-[1,1'-biphenyl]-4-ylethyl)-N-hydroxy-3-isothiazolidinecarboxamide 1,1-dioxide;

(R/S)N-Hydroxy-2-(2-phenylethyl)-3-isothiazolidinecarboxamide 1,1-dioxide;

(R/S) 2-[1,1'-biphenyl]-4-yl-N-hydroxy-3-isothiazolidinecarboxamide 1,1-dioxide;

(R/S)N-Hydroxy-[2-((4'-methoxy-[1,1'-biphenyl]-4-yl)methyl]-3-isothiazolidinecarboxamide 1,1-dioxide;

(R/S)N-Hydroxy-2-[4-(3-thienyl)benzyl]-3-isothiazolidinecarboxamide 1,1-dioxide;

(R/S) 2-[4-(2-furyl)benzyl]-N-Hydroxy-3-isothiazolidinecarboxamide 1,1-dioxide;

(R/S)N-Hydroxy-2-(4-phenoxybenzyl)-3-isothiazolidinecarboxamide 1,1-dioxide;

(R/S)N-Hydroxy-2-[4-(4-methoxyphenoxy)benzyl]-3-isothiazolidinecarboxamide 1,1-dioxide;

(R/S)N-Hydroxy-2-{4-[4-(trifluoromethyl)phenoxy]benzyl}-3-isothiazolidinecarboxamide 1,1-dioxide;

(R/S)N-Hydroxy-2-[4-(4-pyridinylmethoxy)benzyl]-3-isothiazolidinecarboxamide 1,1-dioxide;

(3R) 2-([1,1'-biphenyl]-4-ylmethyl)-N-hydroxy-3-isothiazolidinecarboxamide 1,1-dioxide;

(3R) 2-([1,1'-biphenyl]-4-ylmethyl)tetrahydro-N-hydroxy-2H-1,2-thiazine-3-carboxamide 1,1-dioxide;

(3R)-N-hydroxy-2-((3',4'-dimethoxy[1,1'-biphenyl]-4-yl)methyl)tetrahydro-2H-1,2-thiazine-3-carboxamide 1,1-dioxide;

(3R)-N-hydroxy-2-((4'-methoxy[1,1'-biphenyl]-4-yl)methyl)tetrahydro-2H-1,2-thiazine-3-carboxamide 1,1-dioxide;

(3R)-N-hydroxy-2-((4'-trifluoromethyl[1,1'-biphenyl]-4-yl)methyl)tetrahydro-2H-1,2-thiazine-3-carboxamide 1,1-dioxide;

(3R)-N-hydroxy-2-((4'-tert-butyl[1,1'-biphenyl]-4-yl)methyl)tetrahydro-2H-1,2-thiazine-3-carboxamide 1,1-dioxide;

(3R)-N-hydroxy-2-((4'-chloro[1,1'-biphenyl]-4-yl)methyl)tetrahydro-2H-1,2-thiazine-3-carboxamide 1,1-dioxide;

(3R)-N-hydroxy-2-((4'-methylthio[1,1'-biphenyl]-4-yl)methyl)tetrahydro-2H-1,2-thiazine-3-carboxamide 1,1-dioxide;

(3R)-N-hydroxy-2-((4'-methylsulfonyl[1,1'-biphenyl]-4-yl)methyl)tetrahydro-2H-1,2-thiazine-3-carboxamide 1,1-dioxide;

(3R)-N-hydroxy-2-((3',4'-dichloro[1,1'-biphenyl]-4-yl)methyl)tetrahydro-2H-1,2-thiazine-3-carboxamide 1,1-dioxide;

(3R)-N-hydroxy-2-((4'-methoxycarbonyl[1,1'-biphenyl]-4-yl)methyl)tetrahydro-2H-1,2-thiazine-3-carboxamide 1,1-dioxide;

(3R)-N-hydroxy-2-((3',4'-methylenedioxy[1,1'-biphenyl]-4-yl)methyl)tetrahydro-2H-1,2-thiazine-3-carboxamide 1,1-dioxide;

(3R)-N-hydroxy-2-((4'-nitro[1,1'-biphenyl]-4-yl)methyl)tetrahydro-2H-1,2-thiazine-3-carboxamide 1,1-dioxide;

(3R)-N-hydroxy-2-((4'-amino[1,1'-biphenyl]-4-yl)methyl)tetrahydro-2H-1,2-thiazine-3-carboxamide 1,1-dioxide;

(3R)-N-hydroxy-2-(4-(5-chloro-2-thienyl)benzyl)tetrahydro-2H-1,2-thiazine-3-carboxamide 1,1-dioxide;

(3R)-N-hydroxy-2-(4-(3'-fluorobiphenyl)benzyl)tetrahydro-2H-1,2-thiazine-3-carboxamide 1,1-dioxide;
(3R)-N-hydroxy-2-(4-(2-benzo[b]thiophene)benzyl)tetrahydro-2H-1,2-thiazine-3-carboxamide 1,1-dioxide;
(3R)-N-hydroxy-2-(4-(3-formyl-2-thiophene)benzyl)tetrahydro-2H-1,2-thiazine-3-carboxamide 1,1-dioxide;
(3R)-N-hydroxy-2-(4-(3-pyridinyl)benzyl)tetrahydro-2H-1,2-thiazine-3-carboxamide 1,1-dioxide;
(3R)-N-hydroxy-2-(4-(4-pyridinyl)benzyl)tetrahydro-2H-1,2-thiazine-3-carboxamide 1,1-dioxide;
(3R)-N-hydroxy-2-(4-(2-pyridinyl)benzyl)tetrahydro-2H-1,2-thiazine-3-carboxamide 1,1-dioxide;
(3R)-N-hydroxy-2-(4-(4-methoxy-3-pyridinyl)benzyl)tetrahydro-2H-1,2-thiazine-3-carboxamide 1,1-dioxide;
(3R)-N-hydroxy-2-{4-[(6-methoxy-3-pyridinyl)oxy]benzyl}tetrahydro-2H-1,2-thiazine-3-carboxamide 1,1-dioxide;
N-hydroxy-2-{4-[(2-methyl-4-quinolinyl)methoxy]benzyl}-3-isothiazolidinecarboxamide 1,1-dioxide;
N-hydroxy-2-{4-[(2-methyl-4-quinolinyl)methoxy]phenyl}-3-isothiazolidinecarboxamide 1,1 dioxide;
N-hydroxy-2-(2-{4-[(2-methyl-4-quinolinyl)methoxy]phenyl}ethyl)-3-isothiazolidinecarboxamide 1,1-dioxide;
N-hydroxy-2-{4-[(2-methyl-4-quinolinyl)methoxy]benzyl}tetrahydro-2H-1,2-thiazine-3-carboxamide 1,1-dioxide;
N-hydroxy-2-{4[(2-methyl-4-quinolinyl)methoxy]phenyl}tetrahydro-2H-1,2-thiazine-3-carboxamide 1,1-dioxide;
N-hydroxy-2-{4-[(2-methyl-4-quinolinyl)methoxy]benzyl}tetrahydro-3-thiophenecarboxamide 1,1-dioxide;
N-hydroxy-2-{4-[(2-methyl-4-quinolinyl)methoxy]phenyl}-1,2,5-thiadiazolidine-3-carboxamide 1,1-dioxide;
or a pharmaceutically acceptable salt form thereof.

In another embodiment, the present invention provides a novel pharmaceutical composition, comprising: a pharmaceutically acceptable carrier and a therapeutically effective amount of a compound of the present invention or a pharmaceutically acceptable salt form thereof.

In another embodiment, the present invention provides a novel method for treating an inflammatory disorder, comprising: administering to a patient in need thereof a therapeutically effective amount of a compound of the present invention or a pharmaceutically acceptable salt form thereof.

In another preferred embodiment, the present invention provides a novel method of treating an inflammatory disorder, wherein the disorder is a condition or disease mediated by MMPs, ADAMs, TNF, aggrecanase, or a combination thereof in a mammal, comprising: administering to the mammal in need of such treatment a therapeutically effective amount of a compound of the present invention or a pharmaceutically acceptable salt form thereof.

In another preferred embodiment, the present invention provides a novel method of treating, wherein the condition or disease is referred to as acute infection, acute phase response, age related macular degeneration, alcoholism, allergy, allergic asthma, aneurism, anorexia, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

In another embodiment, the present invention provides novel compounds of the present invention for use in therapy.

In another embodiment, the present invention provides the use of novel compounds of the present invention for the manufacture of a medicament for the treatment of a condition or disease mediated by MMPs, ADAMs, TNF, aggrecanase, or a combination thereof.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

In one of the provisos for $Z^a$, the phrase "wherein the substituent is 1–3 atoms in length" is intended to correspond to a substituent whose length is determined by counting the non-hydrogen atoms. For example, the group "C(O)NH$_2$" would be considered two atoms in length, and the group "CH$_2$CH$_2$CH$_3$" would be considered three atoms in length.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^b$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. $C_{1-10}$ alkyl (or alkylene), is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl.

"Haloalkyl" is intended to include both branched and straight-chain saturated aliphatic hydrocarbon groups having the specified number of carbon atoms, substituted with 1 or more halogen (for example-$C_vF_w$ where v=1 to 3 and w=1 to (2v+1)). Examples of haloalkyl include, but are not limited to, trifluoromethyl, trichloromethyl, pentafluoroethyl, and pentachloroethyl.

"Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy.

"Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups.

"Alkenyl" or "alkenylene" is intended to include hydrocarbon chains of either a straight or branched configuration and one or more unsaturated carbon-carbon bonds which may occur in any stable point along the chain, such as ethenyl and propenyl. $C_{2-10}$ alkenyl (or alkenylene), is intended to include $C_2$, $C_3$, $C_4$, $C_5$, $C_6$, $C_7$, $C_8$, $C_9$, and $C_{10}$ alkenyl groups.

"Alkynyl" or "alkynylene" is intended to include hydrocarbon chains of either a straight or branched configuration and one or more triple carbon-carbon bonds which may occur in any stable point along the chain, such as ethynyl and propynyl. $C_{2-10}$ alkynyl (or alkynylene), is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo. "Counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl.

As used herein, the term "heterocycle" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, NH, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc. . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention or an amount of the combination of compounds claimed effective to inhibit a desired metalloprotease in a host. The combination of compounds is preferably a synergistic combination. Synergy, as described for example by Chou and Talalay, Adv. Enzyme Regul. 22:27–55 (1984), occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. In the schemes, $R^{10}$ is intended to represent an ester group (e.g., alkyl, phenyl, or benzyl).

A series of compounds of formula 5 are prepared via the methods shown in Scheme 1. Derivatives of cysteine disulfide 1 can be oxidized by the action of chlorine gas to provide the sulfonyl chloride 2 (Luisi, G.; Pinnen, F. *Arch. Pharm.* 1993, 326, 139). This material can be cyclized with $Et_3N$ to provide the sultam 3. There are many techniques available to preform the next step that is functionalization of the "NH." Several methods are shown which include: a) alkyation with a base and a halide (RX=eletrophile where X==Cl, Br, I, OTs, OMs, and OTf), b) Mitsunobu conditions, and c) copper insertion chemistry (Chan, D. M. T. et al, *Tetrahedron Lett.* 1998, 39, 2933). After the apropiate group has been placed on the nitrogen, the ester can be converted into the hydroxamic acid. If a methyl ester 4 (R$^{10}$=Me) is present, the conversion can be accomplished with basic hydroxylamine to yield the hydroxamic acid 5.

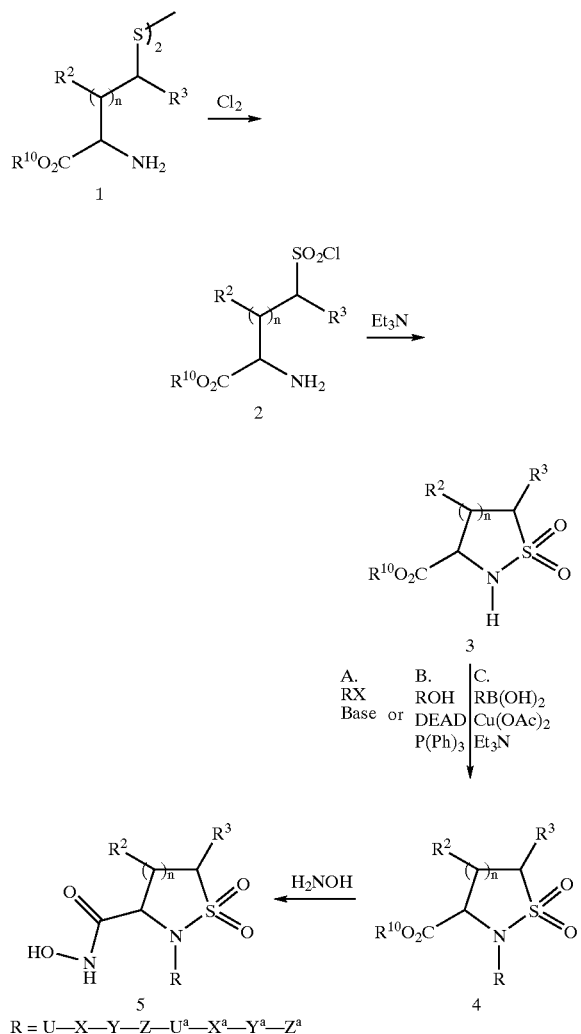

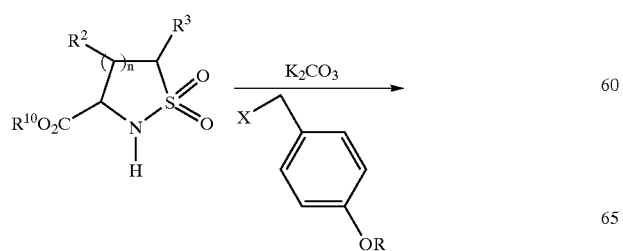

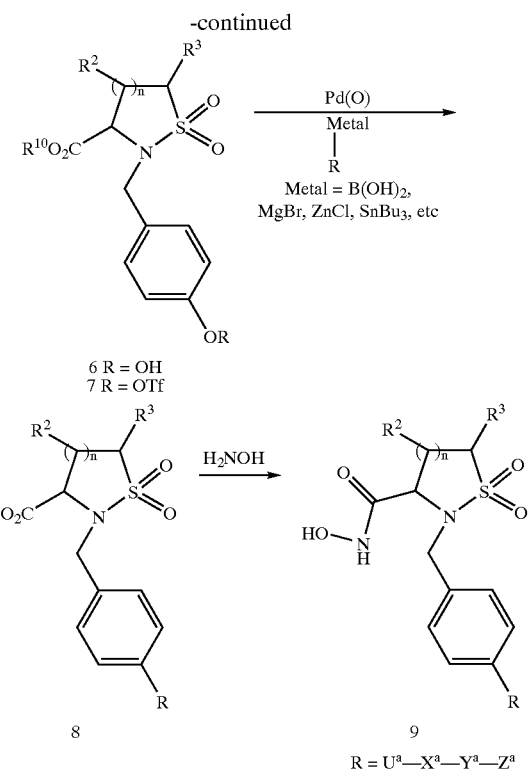

A series of compounds of formula 9 are available as shown in Scheme 2. The sultam 3 can be alkylated with a benzyl halide to give 6. The free phenol can be converted to the triflate 7 with Tf$_2$O. The triflate 7 can participate in a variety of metal catalyzed coupling reactions (Malleron, J. -L. et al, Handbook of Palladium Catalysed Reactions, Academic Press, 1997) to give 8, which is converted to the hydroxamate 9.

A series of compounds of formula 11 are synthesized as shown in Scheme 3. The phenol 6 can be functionalized in many ways, one of which is the copper insertion chemistry (Chan, D. M. T. et al, *Tetrahedron Lett*. 1998, 39, 2933) with a boronic acid. This gives substituted phenol 10, which can be coverted to the hydroxamate 11. The same intermediate 10 can be synthesized by standard alkylation chemistry with K$_2$CO$_3$ and an alkylating agent RX.

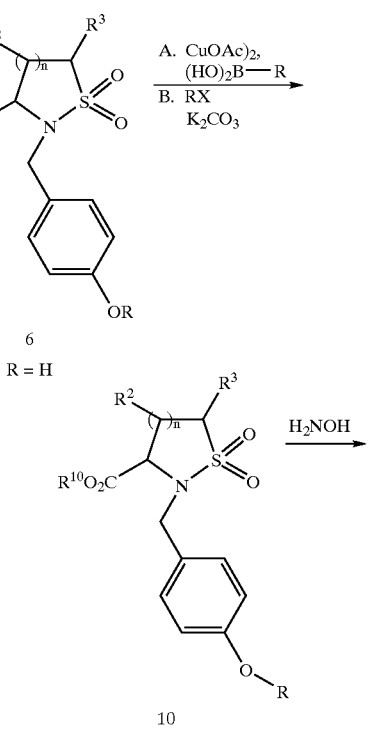

-continued

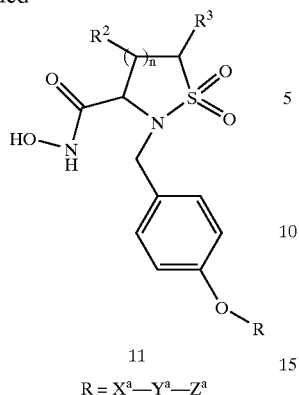

11
R = X$^a$—Y$^a$—Z$^a$

-continued

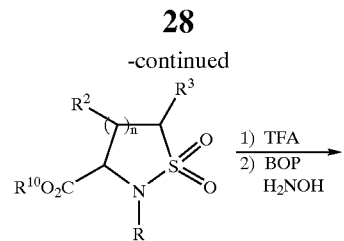

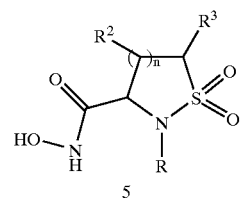

5
R = U-X-Y-Z-U$^a$-X$^a$-Y$^a$-Z$^a$

A series of compounds of formula 5 are also available as shown in Scheme 4. An amino acid derived aldehyde 12 can under go a Grignard addition to yield alcohol 13. Mitsunobu chemistry is then performed to give the thioacetate 14. This material can be oxidized with chlorine gas to yield the sulfonyl chloride 15, which is deprotected to the amine 2. From the amine 2, the same steps to the hydroxamate are followed as in Scheme 1. If the ester in 4 is tert-butyl ($R^{10}$=t-Bu), then it must first be converted to the carboxylic acid with TFA (or other strong acid). This carboxylic acid can be converted to the hydroxamate through any number of coupling procedures like BOP/H$_2$NOH.

A series of compounds of formula 9 are prepared via the methods shown in Scheme 5. The sultam 3 can be alkylated with 4-bromobenzyl bromide to give the alkylated material 16. This alkylated material can be substituted via a wide variety of metal catalyzed cross couplings. For example, a Suzuki reaction with phenyl boronic acid gives 8 (R=Ph), which can be converted to the hydroxamate 9.

Scheme 4

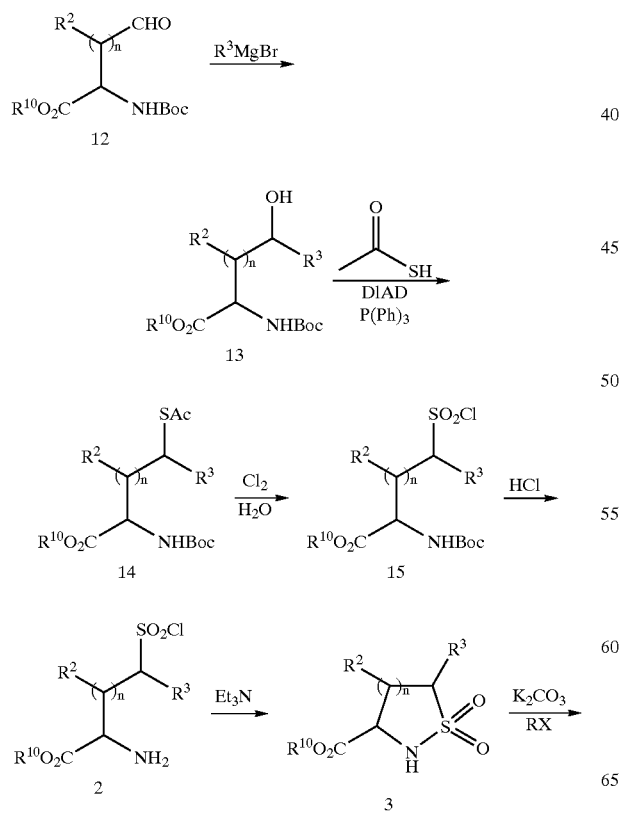

Scheme 5

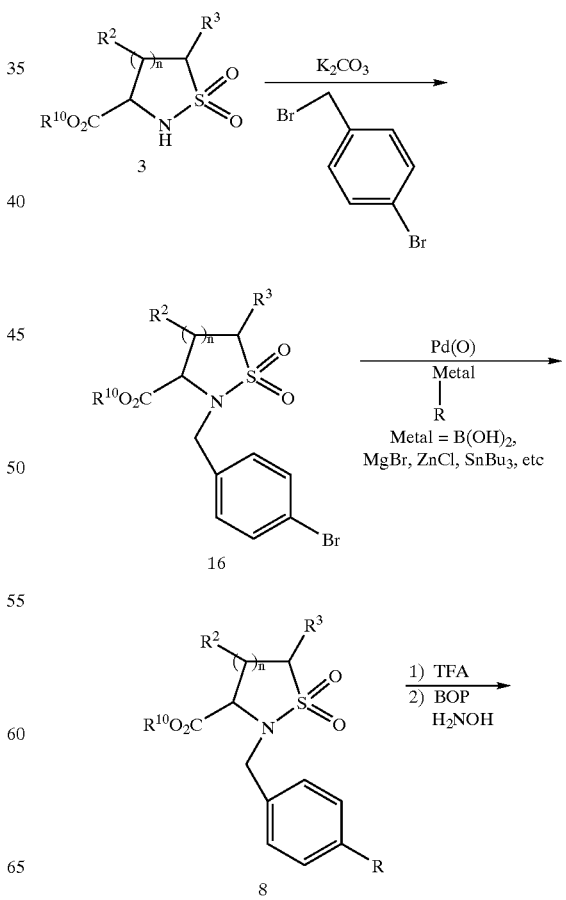

-continued

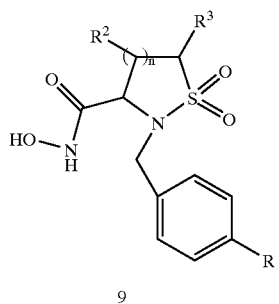

R = U$^a$-X$^a$-Y$^a$-Z$^a$

A series of compounds of formula 22 are synthesized as shown in Scheme 6. The phosphoglycinate 17 (Schmidt, U. et al, *Synthesis*. 1984, 53) can be condensed with the ketone 18 (many are commercially available like methyl acetoacetate; R$^2$=Me; R$^3$=H; R$^4$=O; R$^{11}$=Me) to give, after reduction and protection, the conjugated system 19. At this piont two paths are available. Reduction and deprotection gives the alcohol 20, which can be taken into Scheme 4 to the hydroxamate. In the second option, a conjugate addition (or Michael reaction) can be preformed on 19 to give the disubstituted case 23. After deprotection, this can also be transformed into a hydroxamate via Scheme 4.

Scheme 6

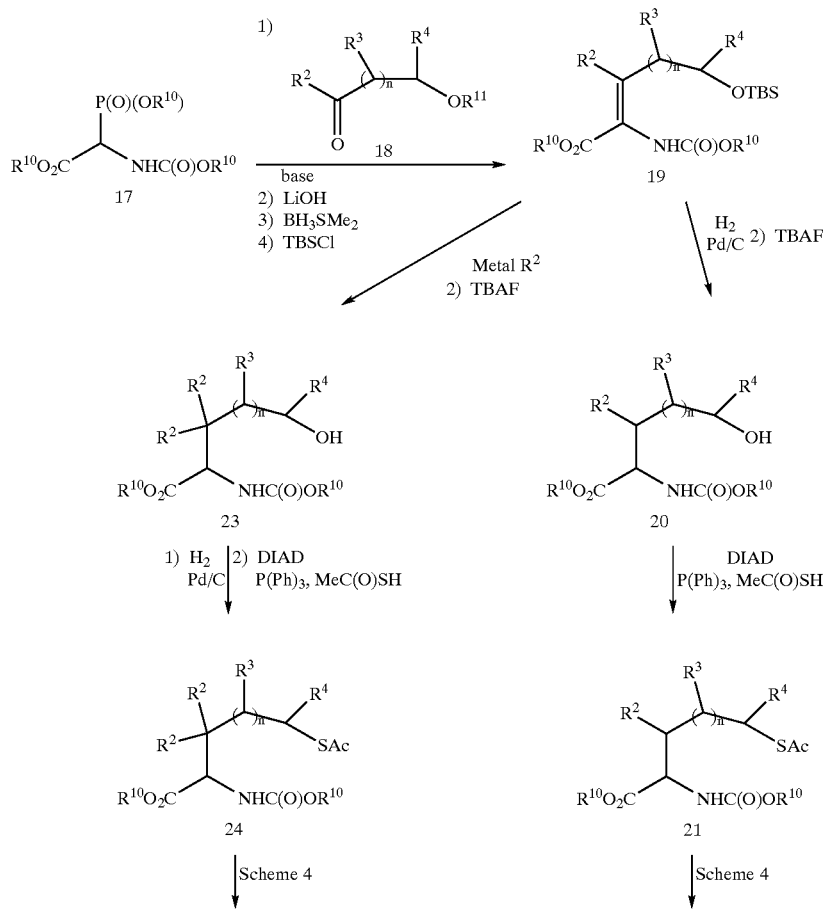

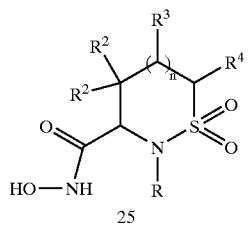

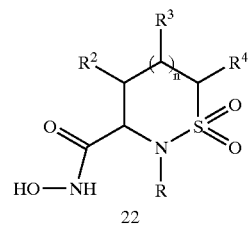

R$^2$ = selected independently
R = U—X—Y—Z—U$^a$—X$^a$—Y$^a$—Z$^a$

Compounds of formula 33 can be prepared starting from diamino esters 26 as shown in Scheme 7. The side chain amine can be protected as the PMB (para-methoxybenzyl) group via reductive alkylation to give 27. The alpha-amino group can be deprotected and cyclized with sulfamide to yield the sulfonyl urea 29. Alkyation of the free amino group affords 30. Oxidative deprotection and then alkylation gives the di-substiuted urea 32. By the standard protocols, the ester of 32 can be converted into the hydroxamate 33.

Compounds of formula 41 can be prepared as shown in Scheme 8. Again, starting from a diamino ester one can protect the alpha-amine as a PMB. The resulting amine 35 can be converted to the sulfonamide 36 with chloromethane-sulfonyl chloride. Deprotection followed by cyclization with triethylamine affords the sultam 37. The free amino group can be alkylated to give 38. Deprotection and then alkylation gives the di-substituted material 40. Once again the ester of 40 can be converted to the hydroxamate 41 via standard chemistry.

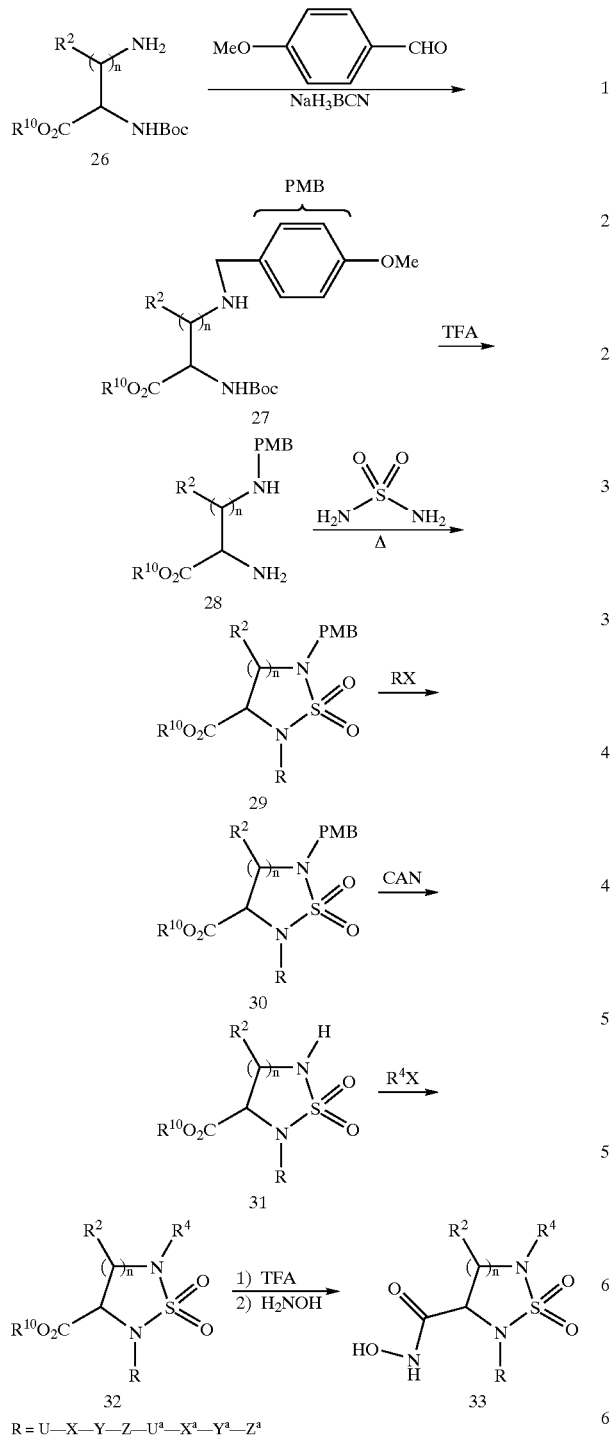

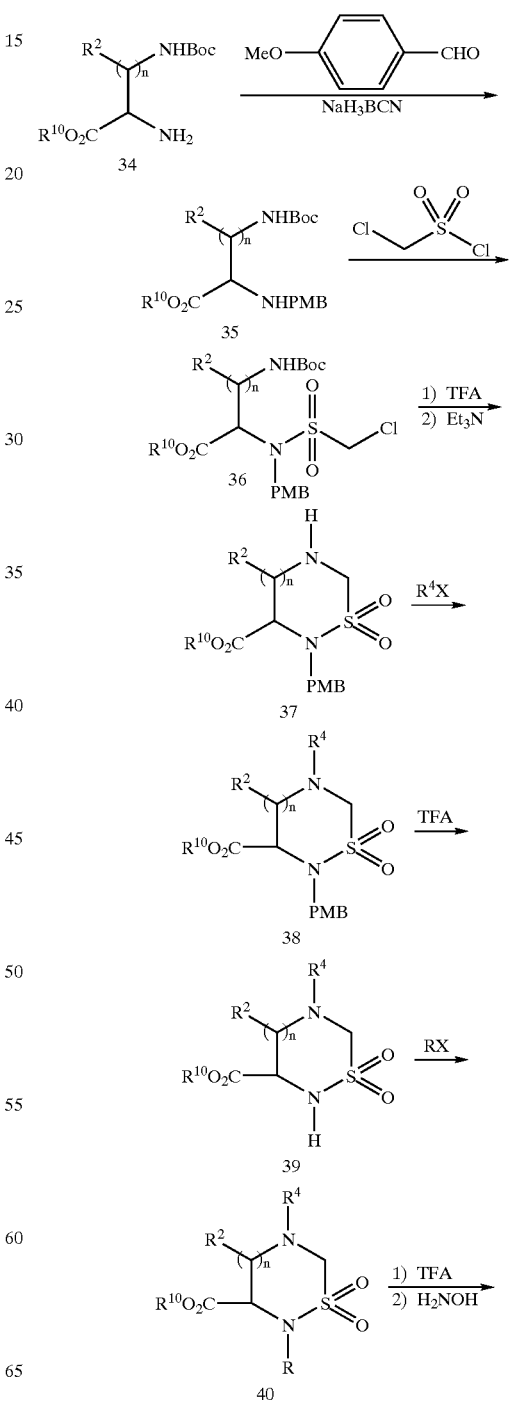

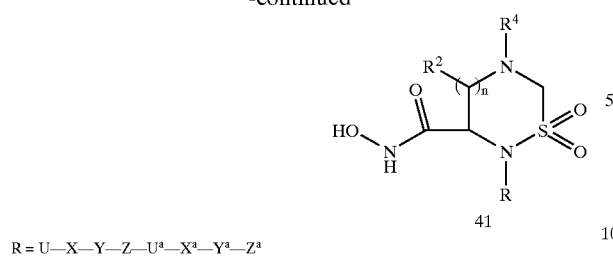

R = U—X—Y—Z—U$^a$—X$^a$—Y$^a$—Z$^a$

A series of compounds of formula 49 are synthesized as shown in Scheme 9. The commercially available 42 (R$^{10}$=Me) can under go a condensation (Ghosh, A. K. et al, *J. Org. Chem.* 1995, 60, 6198) with NaH to give the keto-ester 43. Oxidation with MCPBA gives the sulfone 44. Several options are available at this point. Reduction to the alcohol followed by a Mitsunobu reaction affords the substituted sulfone 45. In the second option (pathway B), a Wittig can be performed followed by reduction of the double bond to provide again the sulfone 45. The ester can be converted to acid 46, which can be akylated alpha to the sulfone to give 47. Using the same strategy, the sulfone can be alkylated at the other position to afford 48. This acid can be converted to the hydroxamate 49 via a BOP coupling with H$_2$NOH added Scheme 9

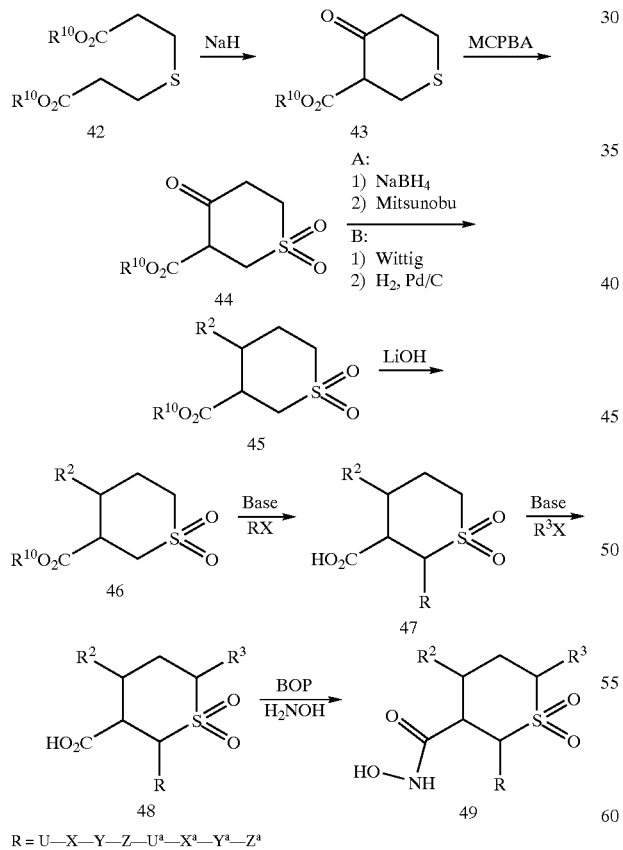

R = U—X—Y—Z—U$^a$—X$^a$—Y$^a$—Z$^a$

A series of compounds of formula 54 are available as shown in Scheme 10. Commercially available thiophenes 50 can be reduced with sodium to afford 51. This material can be oxidized with MCPBA to the sulfone 52. The ester of 52 can be converted to the carboxylate, which can under go a selective alkylation to give 53. This carboxylate can be converted to the hydroxamate 54 via a coupling reaction with BOP and H$_2$NOH.

Scheme 10

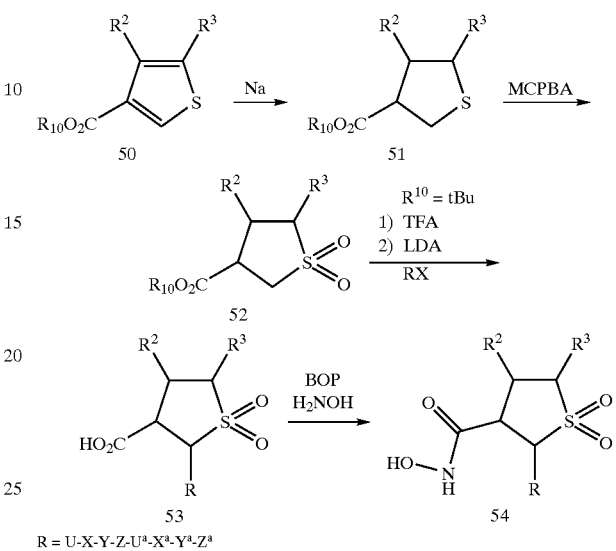

R = U-X-Y-Z-U$^a$-X$^a$-Y$^a$-Z$^a$

A series of compounds of formula 63 are prepared via the methods shown in Scheme 11. The ester 55, derived from aspatic or glutamic acid, can be alkyated with TrisN$_3$ to give 56. The side chain ester can be reduced to give the alcohol, which can undergo a Mitsunobu reaction to give the thioacetate 57. This material can be converted into the sulfonyl chloride 58 by standard exposure with chlorine gas. The nitrogen can be deprotected and cyclized to give the sultam 59. This can be alkyated on the nitrogen to give the substituted sultam 60. Hydrogenation of the azide gives amine 61, which can also be alkylated to afford 62. The ester of 62 can then be converted into the hydroxamate 63 by methods already described.

Scheme 11

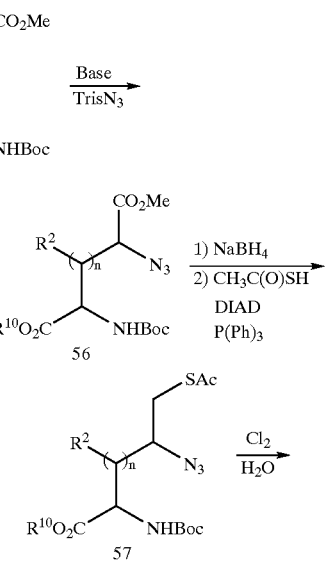

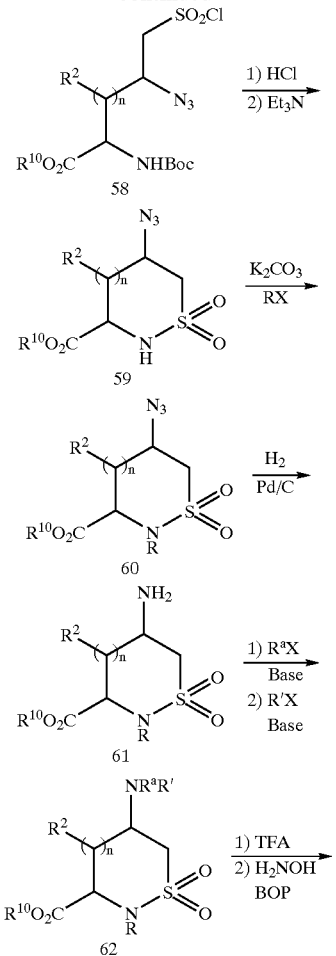

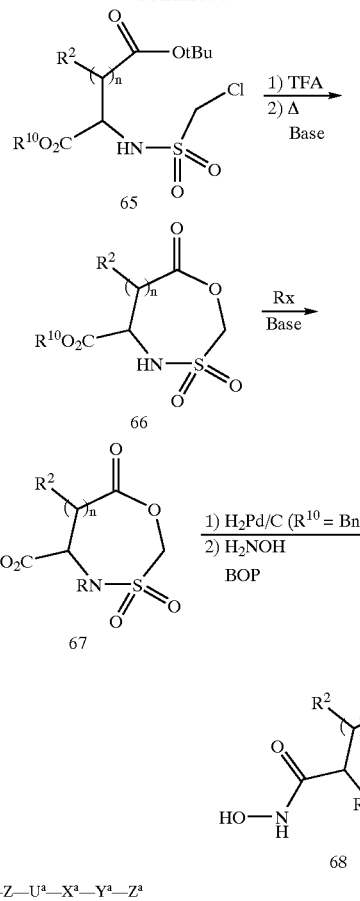

R = U—X—Y—Z—U$^a$—X$^a$—Y$^a$—Z$^a$

R = U—X—Y—Z-U$^a$—X$^a$—Y$^a$—Z$^a$

A series of compounds of formula 68 are synthesized as shown in Scheme 12. The amino acid derived 64 can be converted to the sulfonamide 65 with chloromethanesulfonyl chloride. The ester of 65 can be removed and cyclized to provide the lactone 66. This material can be alkylated to give 67, which can be converted into the hydroxamate 68 by methods already described.

Scheme 12

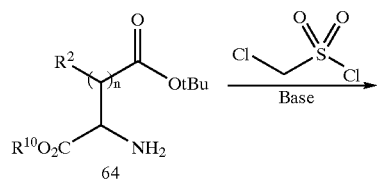

A series of compounds of formula 75 are available as shown in Scheme 13. The amino acid 69 can be converted to the amide 70 via a BOP coupling. The amine can be deprotected and converted to the sulfonamide 72. This material can be cyclized to give the sultam 73. Alkyation of the sultam nitrogen followed by conversion of the ester to the hydroxamate provides 75.

Scheme 13

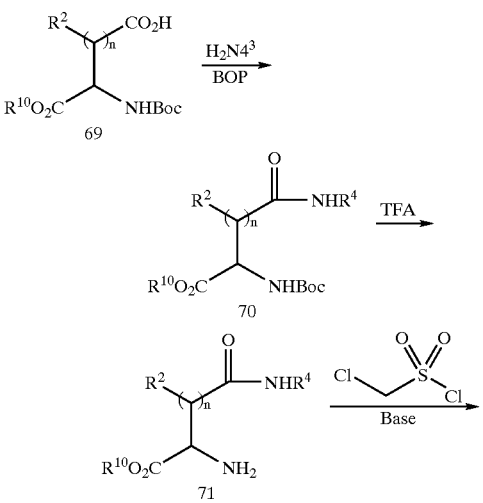

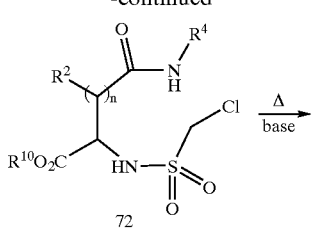

72

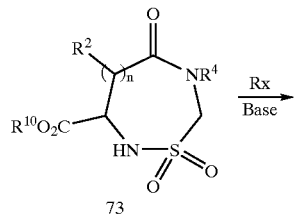

73

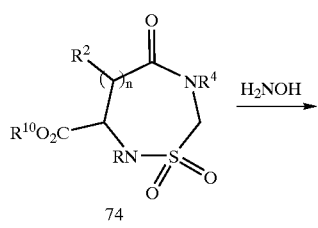

74

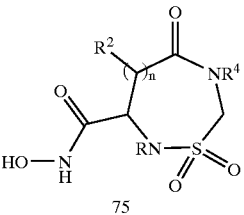

75

R = U—X—Y—Z—U$^a$—X$^a$—Y$^a$—Z$^a$

A series of compounds of formula 80 are synthesized as shown in Scheme 14. The cysteine derivative 76 can be converted to the sulfonamide 77 with chloromethanesulfonyl chloride. The trityl (Tr) can be removed to give the thiol, which can be cyclized to give 78. The free nitrogen can be alkyated under standard conditions to afford 79. This ester can then be converted to the hydroxamate 80 via methods already described.

Scheme 14

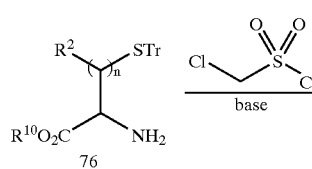

76

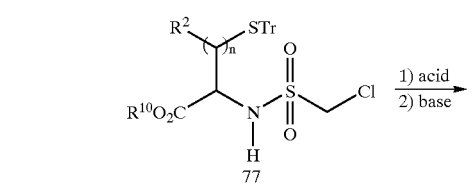

77

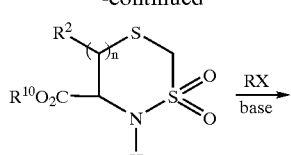

78

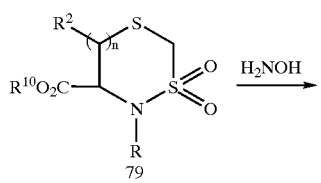

79

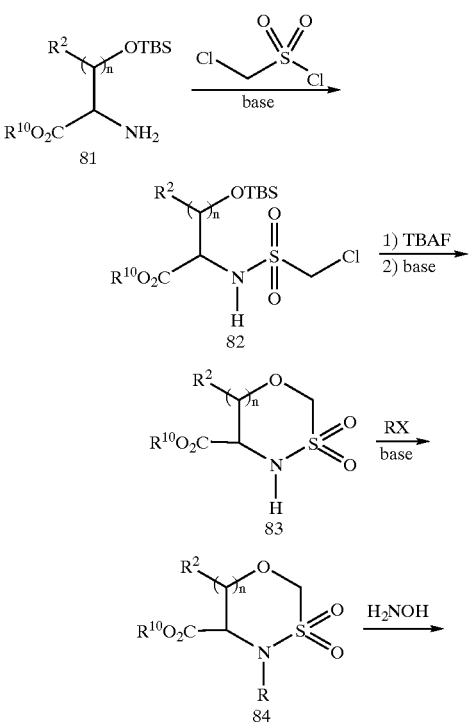

80

R = U—X—Y—Z—U$^a$—X$^a$—Y$^a$—Z$^a$

A series of compounds of formula 85 are available as shown in Scheme 15. The serine derivative 81 can be converted to the sulfonamide 82 with chloromethanesulfonyl chloride. The alcohol of 82 can be unmasked and cyclized to give 83. The nitrogen can be alkylated to afford 84, which can then be converted to the hydroxamate 85 via conditions already described.

Scheme 15

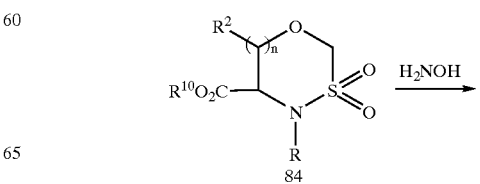

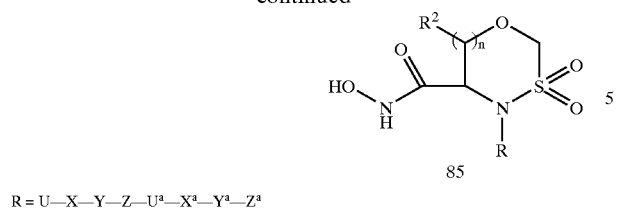

85

R = U—X—Y—Z—U$^a$—X$^a$—Y$^a$—Z$^a$

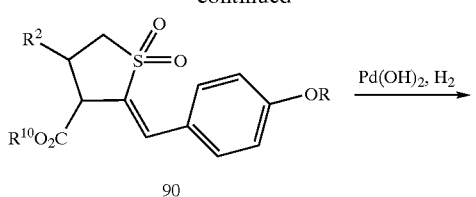

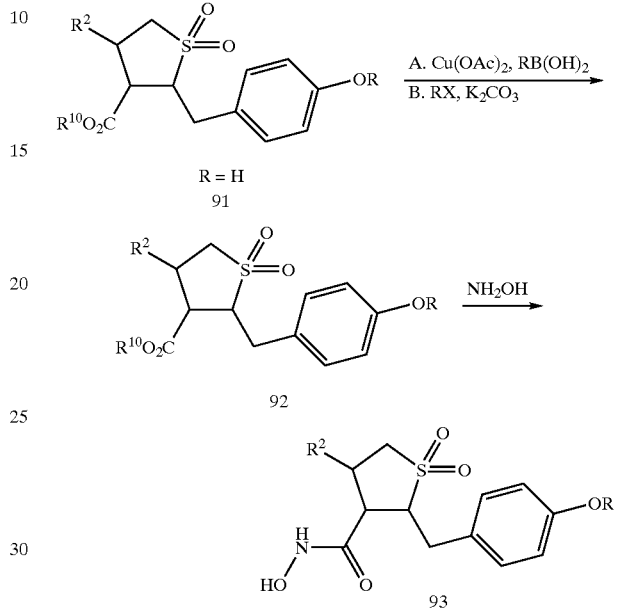

R = U—X—Y—Z—U$^a$—X$^a$—Y$^a$—Z$^a$

A series of compounds of formula 93 are prepared according to Scheme 16. Treatment of bis-(trimethylsilyl)methyl (trimethylsilyl)methyl sulfide 86 with n-butyllithium and an aldehyde can give olefin 87 (Achiwa, K. et al, *Heterocycles* 1995, 40, 249). Oxidation of the sulfide to the sulfoxide 88 can be accomplished with M-CPBA. Reaction of sulfoxide 88 with substituted crotonates in HMPA at 100° C. can result in the formation of cyclic sulfide 89. Oxidation to the sulfone followed by reduction of the olefin and/or removal of a phenol protecting group can lead to sulfone 91. The phenol of 91 can be further functionalized in many ways, one of which involves copper acetate couplings with boronic acids (Chan, D. M. et al, *Tetrahedron Letters* 1998, 39, 2933). Other options include, but are not limited to, simple alkylations with alkyl halides in the presence of potassium carbonate. Final conversion of the functionalized sulfone 92 to hydroxamic acid 93 can be accomplished with basic hydroxylamine solution.

Scheme 16

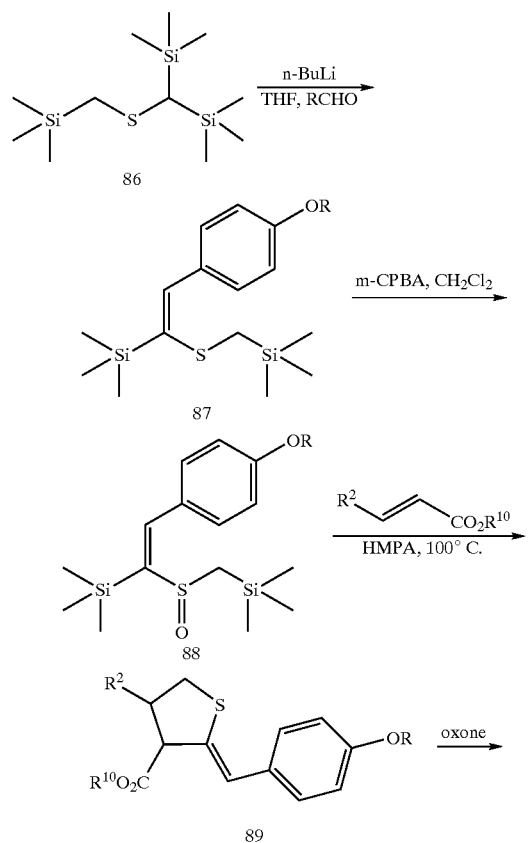

A series of compounds of formula 102 are synthesized as depicted in Scheme 17. Addition of t-butanol to chlorosulfonyl isocyanate 94 followed by the addition of benzyl amine 95 can lead to bis-protected sulfonyl urea 96. Intramolecular cyclization can be accomplished with Mitsonobu type conditions to provide cyclic sulfonyl urea 97. Removal of the benzyl protecting group under standard hydrogenation conditions followed by functionalization of the nitrogen can give 99. Options for functionalizing the nitrogen include but are not limited to copper mediated couplings and simple alkylations. Removal of the Boc protecting group with trifluoroacetic acid allows for the functionalization of the second sulfonyl urea nitrogen through similar chemistry previously described to give ester 101. Final elaboration to hydroxamic acid 102 can be achieved with basic hydroxylamine.

Scheme 17

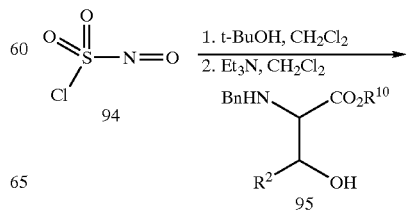

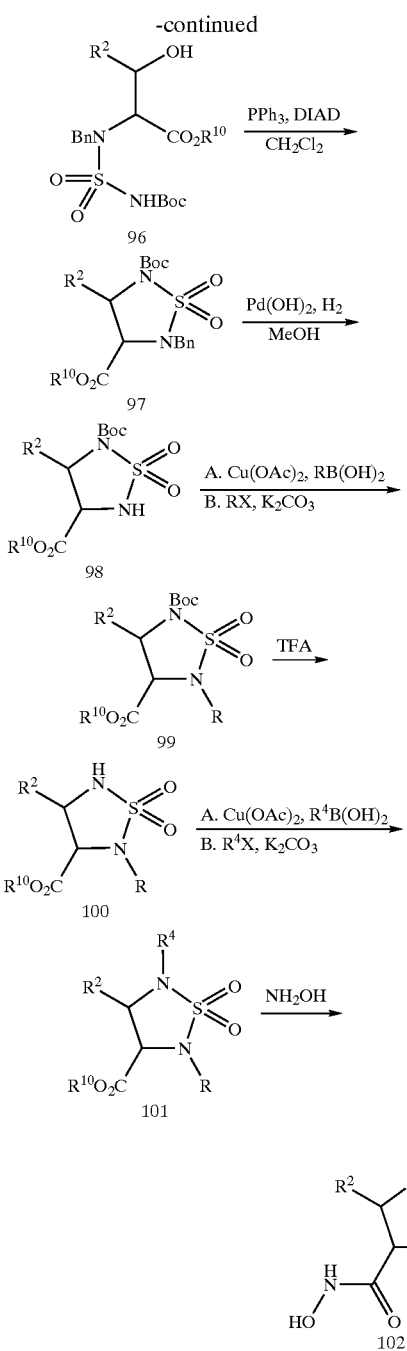

R = U—X—Y—Z—U$^a$—X$^a$—Y$^a$—Z$^a$

Scheme 18

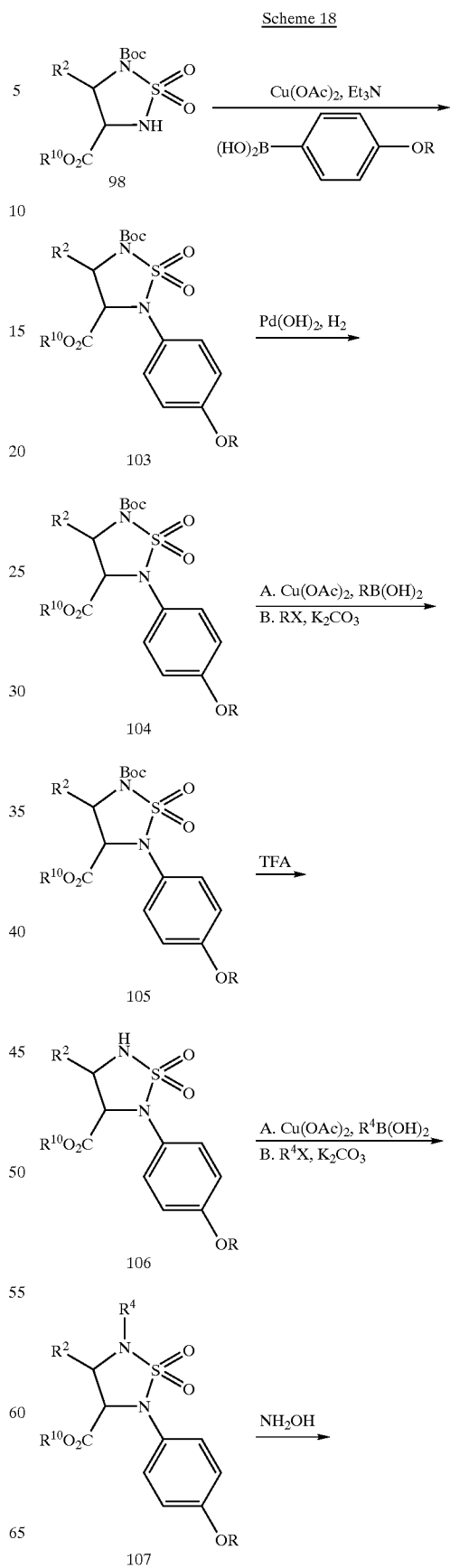

A series of compounds of formula 108 are available as shown in Scheme 18. Copper acetate mediated coupling of sulfonyl urea 98 with an aryl boronic acid can provide 103. When R=benzyl, exposure of ester 103 to hydrogen and a palladium catalyst can give rise to phenol 104. Phenol 104 can be elaborated through many known methods to give functionalized ester 105. Deprotection followed by additional functionalization can provide ester 107. Conversion to hydroxamic acid 108 can be completed using standard conditions.

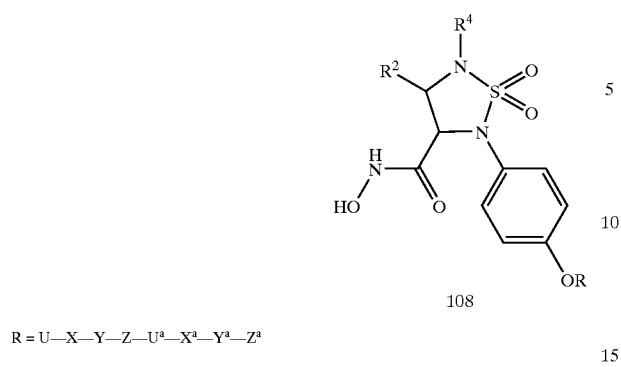

108

R = U—X—Y—Z—U$^a$—X$^a$—Y$^a$—Z$^a$

One stereoisomer of a compound of the present invention may display superior activity compared with the others. Thus, the stereoisomers of the formulas shown in the above description are considered to be part of the present invention. In addition, the following preferred stereoisomers are considered to be a part of the present invention.

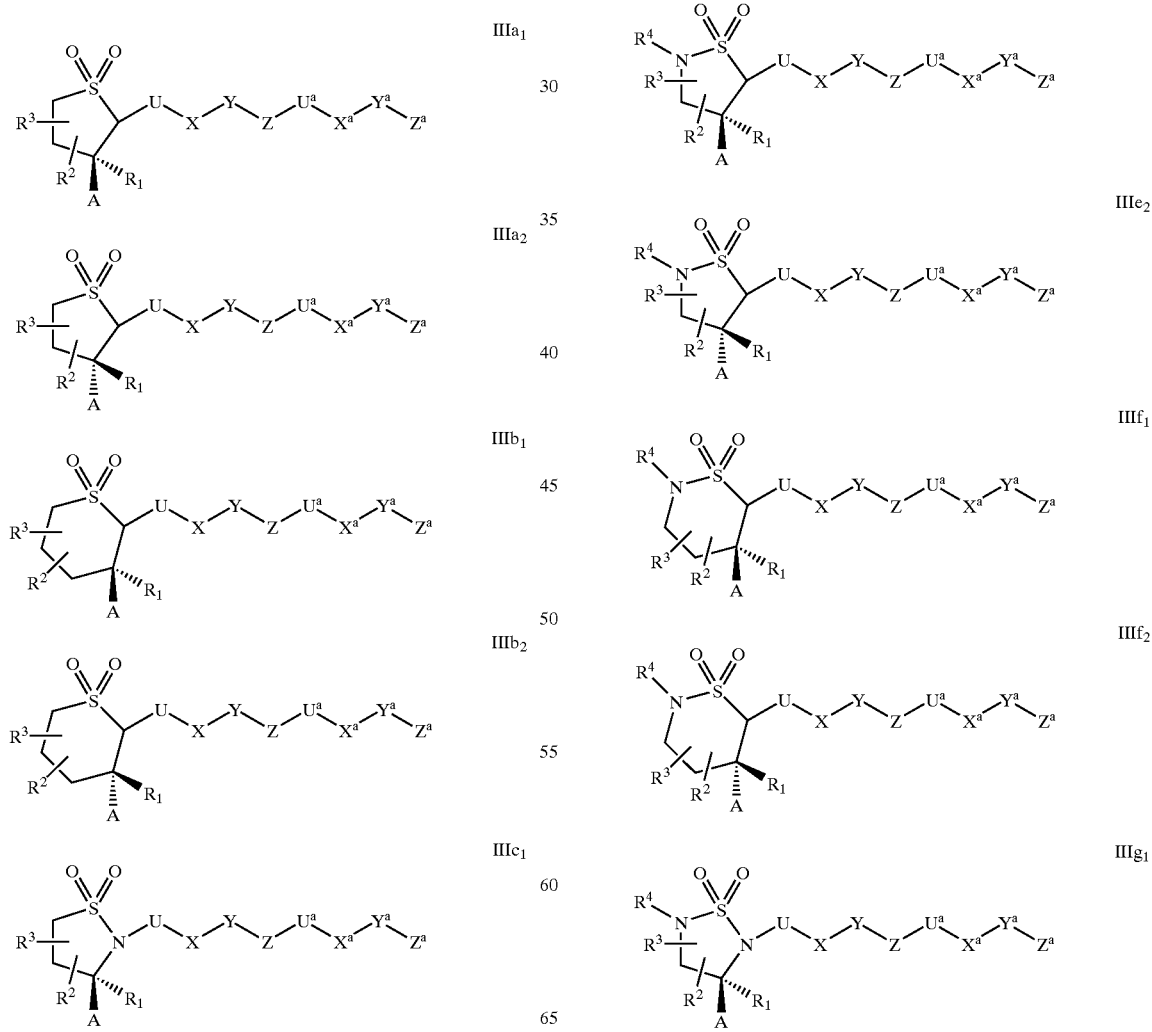

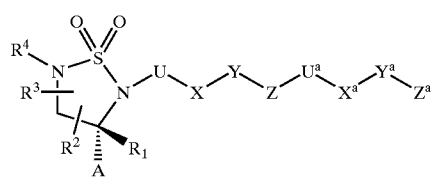
IIIg₂
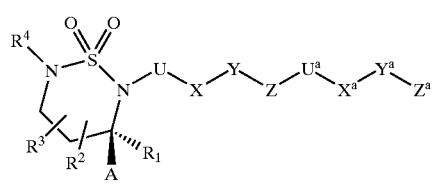
IIIh₁
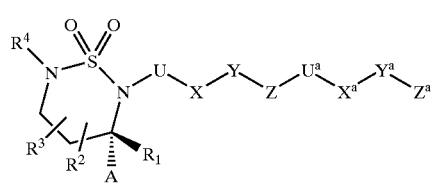
IIIh₂
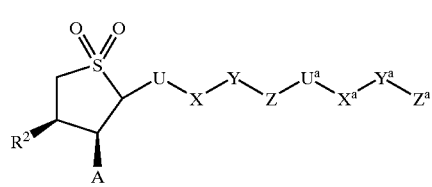
IVa₁
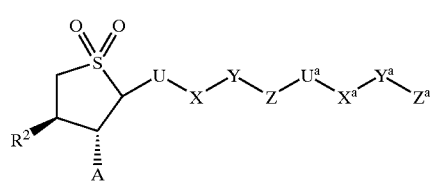
IVa₂
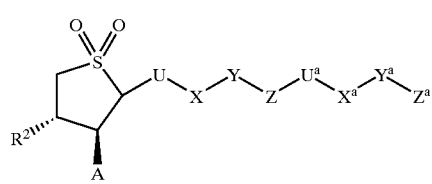
IVa₃
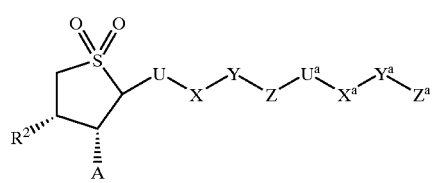
IVa₄
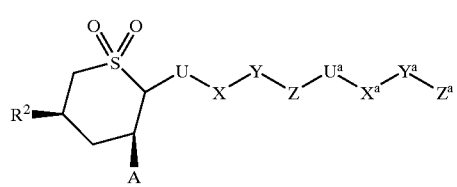
IVb₁
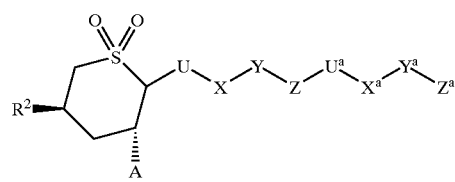
IVb₂
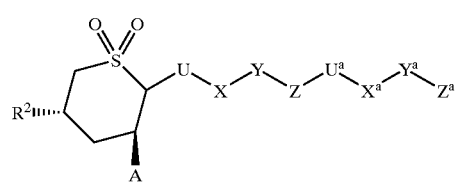
IVb₃
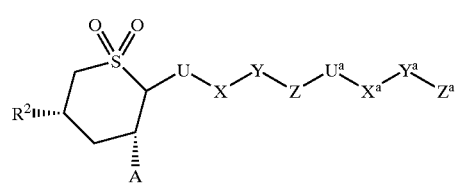
IVb₄
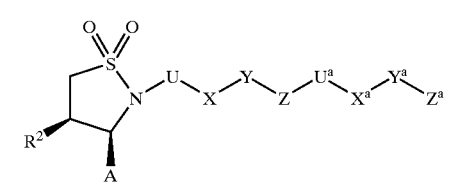
IVc₁
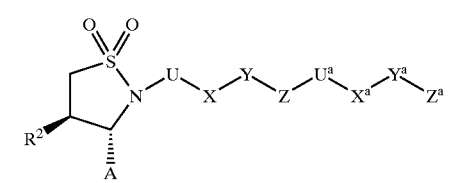
IVc₂
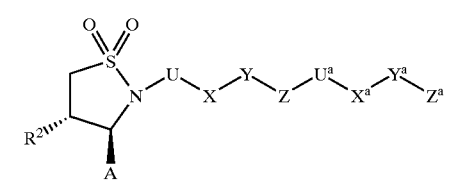
IVc₃
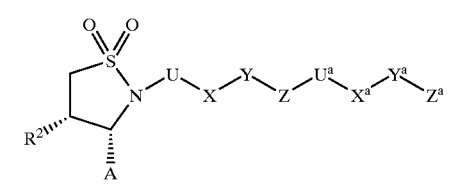
IVc₄
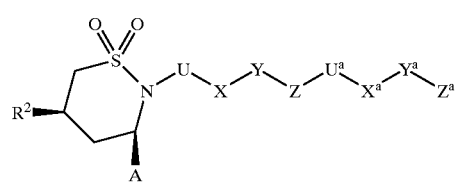
IVd₁

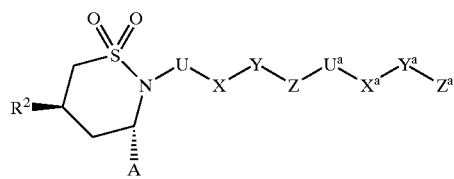 IVd₂
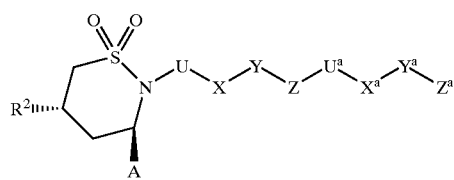 IVd₃
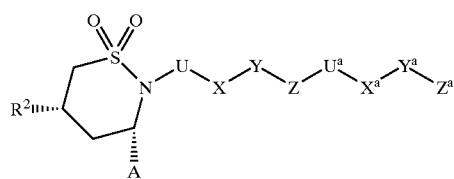 IVd₄
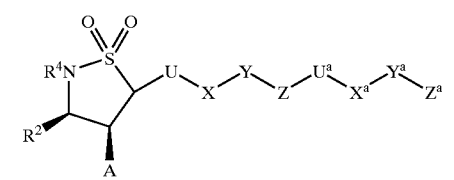 IVe₁
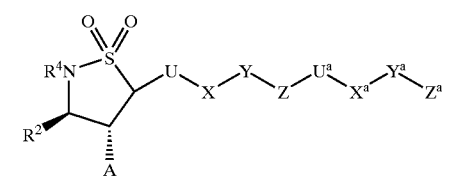 IVe₂
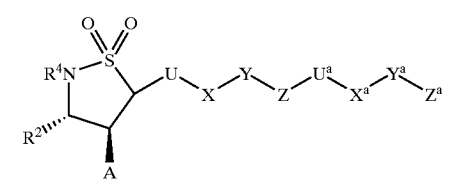 IVe₃
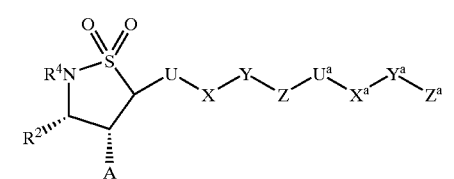 IVe₄
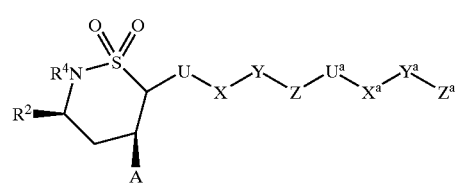 IVf₁
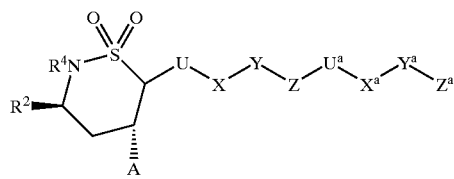 IVf₂
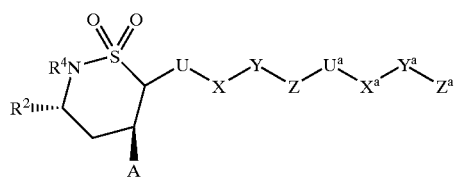 IVf₃
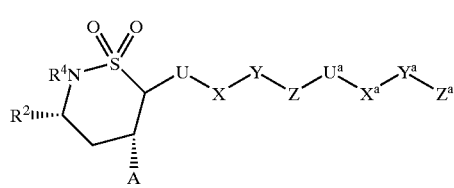 IVf₄
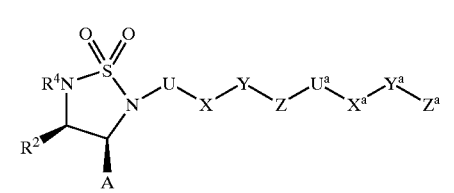 IVg₁
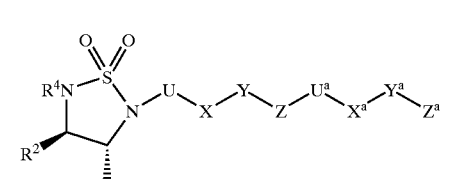 IVg₂
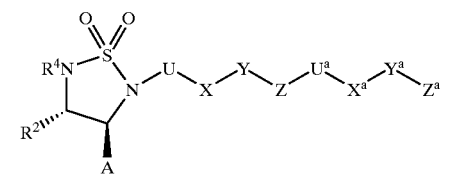 IVg₃
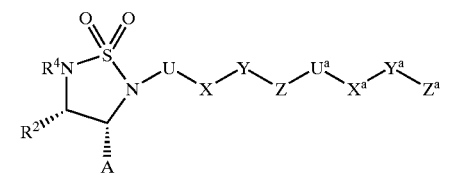 IVg₄
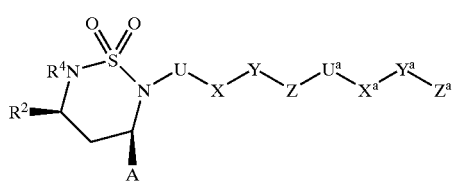 IVh₁

-continued

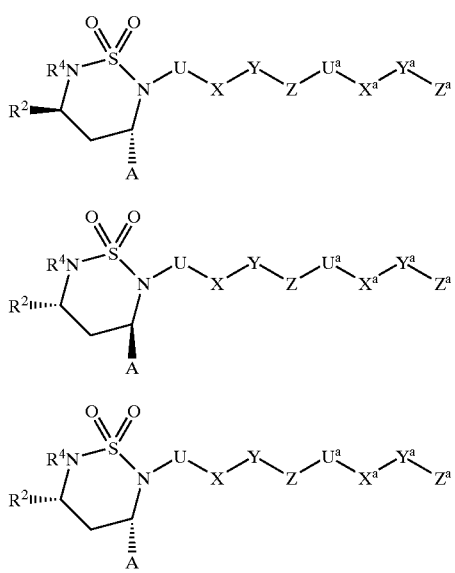

When required, separation of the racemic material can be achieved by HPLC using a chiral column or by a resolution using a resolving agent such as camphonic chloride as in Steven D. Young, et al, *Antimicrobial Agents and Chemotheraphy*, 1995, 2602–2605. A chiral compound of the present invention may also be directly synthesized using a chiral catalyst or a chiral ligand, e.g., Andrew S. Thompson, et al, *Tetr. Lett.* 1995, 36, 8937–8940.

Other features of the invention will become apparent in the course of the following descriptions of exemplary embodiments that are given for illustration of the invention and are not intended to be limiting thereof.

EXAMPLES

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "α", "β", "R" and "S" are stereochemical designations familiar to those skilled in the art.

Example 1

(R/S) 2-([1,1'-biphenyl]-4-ylmethyl)-N-hydroxy-3-isothiazolidinecarboxamide 1,1-dioxide (1a) (R/S)-Homocystine disulfide 1 ($R^2$, $R^3$=H; $R^{10}$=Me; n=1) (7.8 g) was dissolved in a mixture of EtOH and $CHCl_3$. This was cooled to 0° C., and a stream of chlorine gas was bubbled through the solution. After 10 min a precipitate was observed, and the addition of chlorine was stopped. The solution was concentrated and placed on a high vacuum overnight. The resulting residue was taken up in $CHCl_3$ and cooled to −5° C. While at −5° C., $Et_3N$ (20 mL) was added dropwise. After the addition was complete, the solution was warmed to rt. After 30 min, the solution was concentrated. Flash chromatography of the resulting residue gave the sultam 3 ($R^2$, $R^3$=H; $R^{10}$=Me; n=1) (5.7 g). MS found: $(2M+Na)^+$=381.1.

(1b) The sultam 3 ($R^2$, $R^3$=H; $R^{10}$=me; n=1) (2.67 g) was dissolved in DMF prior to the addition of $K_2CO_3$ (6.2 g), 4-benzyloxybenzyl chloride (10.4 g), and $Bu_4NI$ (catalytic). After 5 hrs at rt, the reaction was diluted with EtOAc and brine. The EtOAc layer was washed with additional brine (×2) and dried with $MgSO_4$. The filtered solution was concentrated. Flash chromatography of the resulting material gave the alkylated sultam 4 ($R^2$, $R^3$=H; R=4-benzyloxybenzyl; $R^{10}$=Me; n=1) (5.0 g). MS found: $(M+Na)^+$=398.1.

(1c) Preparation of hydroxylamine/potassium hydroxide solution: A solution of potassium hydroxide (2.81 g, 1.5 eq) in methanol (7 mL) was added to a hot solution of hydroxylamine hydrochloride (2.34 g, 33.7 mmol) in methanol (12 mL). After the mixture was cooled to room temperature, the precipitate was removed by filtration. The filtrate was used fresh with an assumed hydroxylamine concentration of 1.76 M.

The above freshly prepared 1.76 M hydroxylamine solution (2 mL) was added to methyl ester 4 ($R^2$, $R^3$=H; R=4-benzyloxybenzyl; $R^{10}$=Me; n=1) (161 mg) from reaction (1b) and was stirred at room temperature for 1 h (as judged for completion by tlc). The mixture was adjusted to pH 7 with 1 N hydrochloric and filtered. Reverse phase HPLC purification (gradient elution, water/acetonitrile/TFA) provided the title hydroxamic acid 5 ($R^2$, $R^3$=H; R=4-benzyloxybenzyl; n=1) (96 mg). MS found: $(M+Na)^+$=399.1.

Example 2

(R/S) 2-(2-[1,1'-biphenyl]-4-ylethyl)-N-hydroxy-3-isothiazolidinecarboxamide 1,1-dioxide (2a) The sultam 3 ($R^2$, $R^3$=H; $R^{10}$=Me; n=1) (300 mg) was dissolved in THF along with $P(Ph)_3$ (658 mg) and [1,1'-biphenyl]-2-ethanol (498 mg). The mixture was cooled to 0° C. and DEAD was added. The reaction was warmed to rt and stirred overnight. The solvent was removed. Flash chromatography of the resulting material gave the alkylated sultam 4 ($R^2$, $R^3$=H; R=biphenylethyl; $R^{10}$=Me; n=1) (556 mg). MS found: $(M+Na)^+$=382.2.

(2b) The alkylated sultam 4 ($R^2$, $R^3$=H; R=biphenylethyl; n=1) (273 mg) was treated as in (1c) to yield the title hydroxamate 5 ($R^2$, $R^3$=H; R=biphenylethyl; n=1) (273 mg). MS found: $(M+Na)^+$=383.1.

Example 3

(R/S)N-Hydroxy-2-(2-phenylethyl)-3-isothiazolidinecarboxamide 1,1-dioxide (3a) Phenethyl alcohol (204 mg) was incorporated into the above procedures, (2a)–(2b), to give the title hydroxamate 5 ($R^2$, $R^3$=H; R=phenethyl; n=1) (273 mg). MS found: $(M+Na)^+$=306.1.

Example 4

(R/S) 2-[1,1'-biphenyl]-4-yl-N-hydroxy-3-isothiazolidinecarboxamide 1,1-dioxide (4a) The sultam 3 ($R^2$, $R^3$=H; $R^{10}$=Me; n=1) (300 mg) was dissolved in $CH_2Cl_2$ along with $Cu(OAc)_2$ (193 mg), $Et_3N$ (410 mg), 4 Å molecular sieves (140 mg), and 4-biphenylboronic acid (321 mg). The reaction was stirred in open air for 3 days. The reaction was partitioned between 1 N HCl and $CH_2Cl_2$. The organic layer was dried, filtered, and concentrated. Flash chromatography of the resulting residue gave the alkylated sultam 4 ($R^2$, $R^3$=H; R=4-biphenyl; $R^{10}$=Me; n=1) (35 mg). MS found: $(2M+Na)^+$=685.3.

(4b) The sultam 4 ($R^2$, $R^3$=H; R=4-biphenyl; $R^{10}$=Me; n=1) (35 mg) was treated as in (1c) to yield the title hydroxamate 5 ($R^2$, $R^3$=H; R=4-biphenyl; n=1) (6.6 mg). MS found: $(M+H)^+$=333.2.

Example 5

(R/S)N-Hydroxy-2-((4'-methoxy-[1,1'-biphenyl]-4-yl)methyl]-3-isothiazolidinecarboxamide 1,1-dioxide (5a) The sultam 4 ($R^2$, $R^3$=H; R=4-benzyloxybenzy; $R^{10}$=Me; n=1) (7.0 g) was dissolved in MeOH prior to the addition of 5% Pd/BaSO$_4$ (4 g). A hydrogen balloon was added, and the solution was stirred for 2.5 h. The hydrogen balloon was removed, and the solution was filtered and concentrated. This gave the phenol 6 ($R^2$, $R^3$=H; R=H; $R^{10}$=Me; n=1) (quant.) ready for subsequent reactions. MS found: $(M+Na)^+$=308.1.

(5b) The phenol 6 ($R^2$, $R^3$=H; R=H; $R^{10}$=Me; n=1) (506 mg) was dissolved in CH$_2$Cl$_2$ and Hunig's base (0.93 mL) was added. This was cooled to −78° C. and Tf$_2$O (0.3 mL) was added. After 2 hrs, the reaction was quenched with NH$_4$Cl and was extracted with CH$_2$Cl$_2$. The organic layer was washed with brine, dried, and concentrated. Flash chromatography of the resulting material gave the triflate 7 ($R^2$, $R^3$=H; R=Tf; $R^{10}$=Me; n=1) (5.0 g). MS found: $(M+Na)^+$=440.0.

(5c) The triflate 7 ($R^2$, $R^3$=H; R=Tf; $R^{10}$=Me; n=1) (200 mg) was dissolved in toluene prior to the addition of K$_2$CO$_3$ (265 mg), P(Ph)$_3$ (126 mg), Pd(OAc)$_2$ (21 mg), and 4-methoxybenzeneboronic acid (146 mg). This mixture was heated at 70° C. for 4 hrs. After cooling, the reaction was quenched with 1 N HCl and extracted with CH$_2$Cl$_2$. The organic layer was washed with NaHCO$_3$ solution and brine. The organic layer was dried, filtered, and concentrated. Flash chromatography of the resulting residue gave the biaryl 8 ($R^2$, $R^3$=H, R=4-methoxybenzyl; $R^{10}$=Me; n=1) (161 mg). MS found: $(M+Na)^+$=398.1.

(5d) The biaryl 8 ($R^2$, $R^3$=H, R=4-methoxybenzyl; $R^{10}$=Me; n=1) (35 mg) was treated as in (1c) to yield the title hydroxamate 9 ($R^2$, $R^3$=H, R=4-methoxybenzyl; n=1) (96 mg). MS found: $(2M-H)^-$=751.4.

Example 6

(R/S)N-Hydroxy-2-[4-(3-thienyl)benzyl]-3-isothiazolidinecarboxamide 1,1-dioxide (6a) Thiophene-3-boronic acid (105 mg) was incorporated into the above procedures, (5c)–(5d), to give the title hydroxamate 9 ($R^2$, $R^3$=H; R=3-thiophene; n=1) (46 mg). MS found: $(2M-H)^+$=703.2.

Example 7

(R/S) 2-[4-(2-furyl)benzyl]-N-Hydroxy-3-isothiazolidinecarboxamide 1,1-dioxide (7a) Furan-2-boronic acid (94 mg) was incorporated into the above procedures, (5c)–(5d), to give the title hydroxamate 9 ($R^2$, $R^3$=H; R=2-furanyl; n=1) (5 mg) $^1$H NMR (300 MHz, DMSO-d$_6$) ppm δ 2.24 (m, 1H), 2.42 (m, 1H), 3.16 (m, 1H), 3.34 (m, 1H), 3.57 (m, 1H), 3.78 (d, 1H), 4.06 (d, 1H), 6.68 (d, 1H), 6.94 (m, 1H), 7.5–7.3 (m, 5H).

Example 8

(R/S)N-Hydroxy-2-(4-phenoxybenzyl)-3-isothiazolidinecarboxamide 1,1-dioxide (8a) The phenol 6 ($R^2$, $R^3$=H; R=H; $R^{10}$=Me; n=1) (172 mg) was dissolved in CH$_2$Cl$_2$ along with Cu(OAc)$_2$ (144 mg), Et$_3$N (305 mg), 4A molecular sieves (170 mg), and benzeneboronic acid (147 mg). The reaction was stirred in open air overnight. The reaction was partitioned between 1 N HCl and CH$_2$Cl$_2$. The organic layer was dried, filtered, and concentrated. Flash chromatography of the resulting residue gave the alkylated phenol 10 ($R^2$, $R^3$=H; R=phenyl; $R^{10}$=Me; n=1) (71 mg). MS found: $(M+Na)^+$=384.1.

(8b) The alkylated phenol 10 ($R^2$, $R^3$=H; R=phenyl; $R^{10}$=Me; n=1) (35 mg) was treated as in (1c) to yield the title hydroxamate 11 ($R^2$, $R^3$=H; R=phenyl; n=1) (36 mg). MS found: $(2M+Na)^+$=744.4.

Example 9

(R/S)N-Hydroxy-2-[4-(4-methoxyphenoxy)benzyl]-3-isothiazolidinecarboxamide 1,1-dioxide (9a) 4-Methoxybenzeneboronic acid (121 mg) was incorporated into the above procedures, (8a)–(8b), to give the title hydroxamate 11 ($R^2$, $R^3$=H; R=4-methoxyphenyl; n=1) (62 mg). MS found: $(2M-H)^-$=783.4.

Example 10

(R/S)N-Hydroxy-2-{4-[4-(trifluoromethyl)phenoxy]benzyl}-3-isothiazolidinecarboxamide 1,1-dioxide (10a) 4-(Trifluoromethyl)benzeneboronic acid (153 mg) was incorporated into the above procedures, (8a)–(8b), to give the title hydroxamate 11 ($R^2$, $R^3$=H; R=4-trifluoromethylphenyl; n=1) (52 mg). MS found: $(2M-H)^+$=859.2.

Example 11

(R/S)N-Hydroxy-2-[4-(4-pyridinylmethoxy)benzyl]-3-isothiazolidinecarboxamide 1,1-dioxide (11a) The phenol 6 ($R^2$, $R^3$=H; R=H; $R^{10}$=Me; n=1) (177 mg) was dissolved in DMF prior to the addition of Cs$_2$CO$_3$ (1 g) and 4-picolyl chloride hydrogen chloride (203 mg). After stirring overnight at rt, the reaction was diluted with EtOAc and water. The EtOAc layer was washed with additional brine and dried with MgSO$_4$. The filtered solution was concentrated. Flash chromatography of the resulting residue gave the alkylated phenol 12 ($R^2$, $R^3$=H; R=4-picolyl; $R^{10}$=Me; n=1) (46 mg). MS found: $(M+Na)^+$=399.1.

(11b) The alkylated phenol 12 ($R^2$, $R^3$=H; R=4-picolyl; $R^{10}$=Me, n=1) (35 mg) was treated as in (1c) to yield the title hydroxamate 5 ($R^2$, $R^3$=H; R=4-picolyl; n=1) (6.6 mg). MS found: $(M+Na)^+$=378.2.

Example 12

(3R) 2-([1,1'-biphenyl]-4-ylmethyl)-N-hydroxy-3-isothiazolidinecarboxamide 1,1-dioxide (12a) P(Ph)$_3$ (9.7 g) was dissolved in THF and cooled to 0° C. prior to the addition of DIAD (7.5 g). N-[(1,1-dimethylethoxy)carbonyl]-R-homoserine 1,1-dimethylethyl ester 13 ($R^2$, $R^3$=H; $R^{10}$=tBu; n=1) (5.1 g) and thioacetic acid (2.8 g) as a mixture in THF were added dropwise. This mixture was stirred for 1 h at 0° C. and 1 h at rt. EtOAc and brine were added. The organic layer was washed with NaHCO$_3$ solution, dried, filtered, and concentrated. Flash chromatography of the resulting residue gave the (3R)-thioacetate 14 ($R^2$, $R^3$=H; $R^{10}$=t-Bu; n=1) (4.9 g). MS found: $(M+Na)^+$=356.2.

(12b) The (3R)-thioacetate 14 ($R^2$, $R^3$=H; $R^{10}$=t-Bu; n=1) (790 mg) was suspended in water and chlorine gas was bubbled through the mixture. After 35 min, chlorine addition was stopped. The mixture was partially concentrated. The remaining aqueous layer was extracted with $CH_2Cl_2$. The organic layer was dried, filtered, and concentrated. This residue was dissolved in EtOAc and 1M HCl in dioxane (190 mL) was added. The solution was concentrated and dried on a high vacuum. This residue was dissolved in $CHCl_3$ and cooled to −5° C. prior to the addition of $Et_3N$ (1.6 mL) The reaction was stirred overnight at rt. This mixture wash quenched with 1 N HCl solution. The organic layer was washed with brine, dried, filtered, and concentrated. Flash chromatography of the resulting residue gave the (3R)-sultam 3 ($R^2$, $R^3$=H; $R^{10}$=t-Bu; n=1) (135 mg). $^1H$ NMR (300 MHz, $CDCl_3$) ppm δ 1.45 (s, 9H), 2.48 (m, 1H), 2.75 (m, 1H), 2.94 (m, 1H), 3.15 (m, 1H), 4.05 (m, 1H), 5.01 (br s, 1H).

(12c) The (3R)-sultam 3 ($R^2$, $R^3$=H; $R^{10}$=t-Bu; n=1) (103 mg) was dissolved in acetone prior to the addition of 4-bromomethyl biphenyl (150 mg). At rt, $K_2CO_3$ (193 mg) was added and the reaction was stirred overnight. This solution was filtered and concentrated. Flash chromatography of the resulting residue gave the alkylated sultam 4 ($R^2$, $R^3$=H; R=biphenylmethyl; $R^{10}$=t-Bu; n=1) (168 mg). MS found: $(M+Na)^+$=410.1.

(12d) The alkylated (3R)-sultam 4 ($R^2$, $R^3$=H; R=4-biphenyl methyl; $R^{10}$=tBu; n=1) (168 mg) was dissolved in $CH_2Cl_2$ (10 mL) prior to the addition of TFA (2.5 mL). After 3 h, the solution was concentrated. The resulting residue was dissolved in DMF and Hunigs's base (101 mg) was added. After cooling to 0° C., BOP (327 mg) was added. This solution was stirred 30 min before and mixture of $H_2NOHHCl$ (160 mg) and Hunig's base (52 mg) was added. This material was filtered and reverse phase HPLC purification (gradient elution, water/acetonitrile/TFA) provided the title hydroxamic acid 5 ($R^2$, $R^3$=H; R=4-biphenyl methyl; n=1) (40 mg). MS found: $(M+H)^+$=347.1.

Example 13

(3R) 2-([1,1'-biphenyl]-4-ylmethyl)tetrahydro-N-hydroxy-2H-1,2-thiazine-3-carboxamide 1,1-dioxide (13a) The alcohol N-[(1,1-dimethylethoxy)carbonyl]-D-Novaline 1,1-dimethylethyl ester 13 ($R^2$, $R^3$=H; $R^{10}$=t-Bu; n=2) (14.5 g) was incorporated into the above procedures, (12a)–(12b), to give the sultam 3 ($R^2$, $R^3$=H; $R^{10}$=tBu; n=2) (5.5 g). MS found: $(M+H)^+$=236.1.

(13b) The (3R)-sultam 3 ($R^2$, $R^3$=H; $R^{10}$=t-Bu; n=2) (150 mg) was treated as in procedure (12c)–(12d) to give the title hydroxamic acid 5 ($R^2$, $R^3$=H; R=4-biphenyl methyl; n=2) (15 mg). MS found: $(M+H)^+$=361.2.

Example 14

(3R)-N-hydroxy-2-((3',4'-dimethoxy[1,1'-biphenyl]-4-yl)methyl)tetrahydro-2H-1,2-thiazine-3-carboxamide 1,1-dioxide (14a) The (3R)-sultam 3 ($R^2$, $R^3$=H; $R^{10}$=t-Bu; n=2) (2 g) was dissolved in DMF prior to the addition of $K_2CO_3$ (3.5 g), 4-benzyloxybenzyl chloride (2.5 g), and $Bu_4NI$ (catalytic). After 6 hrs at rt, the reaction was diluted with EtOAc and water. The organic layer was washed with additional brine (×2) and dried with $MgSO_4$. The filtered solution was concentrated. Flash chromatography of the resulting material gave the alkylated (3R)-sultam 4 ($R^2$, $R^3$=H; R=4-benzyloxybenzyl; $R^{10}$=tBu; n=2) (3.6 g). MS found: $(M+Na)^+$=454.2.

(14b) The (3R)-sultam 4 ($R^2$, $R^3$=H; R=4-benzyloxybenzyl; $R^{10}$=t-Bu; n=2) (3.7 g) was dissolved in MeOH prior to the addition of 5% $Pd/BaSO_4$ (2 g). A hydrogen balloon was added, and the solution was stirred for 2.5h. The hydrogen balloon was removed, and the solution was filtered and concentrated. This gave the (3R)-phenol 6 ($R^2$, $R^3$=H; $R^{10}$=t-Bu; n=2) (2.5 g) ready for subsequent reactions. MS found: $(M+Na)^+$=364.2.

(14c) The (3R)-phenol 6 ($R^2$, $R^3$=H; $R^{10}$=t-Bu; n=2) (1.5 g) was dissolved in $CH_2Cl_2$ and Hunig's base (1.1 mL) was added. This was cooled to −78° C. and $Tf_2O$ (0.89 mL) was added. After 2 hrs, the reaction was quenched with $NH_4Cl$ and was extracted with $CH_2Cl_2$. The organic layer was washed with brine, dried, and concentrated. Flash chromatography of the resulting material gave the (3R)-triflate 7 ($R^2$, $R^3$=H; $R^{10}$=t-Bu; n=2) (3.6 g). MS found: $(M+Na)^+$=496.1.

(14d) The (3R)-triflate 7 ($R^2$, $R^3$=H; $R^{10}$=t-Bu; n=2) (200 mg) was dissolved in toluene prior to the addition of $K_2CO_3$ (233 mg), $P(Ph)_3$ (111 mg), $Pd(OAc)_2$ (19 mg), and 3,4-dimethoxybenzeneboronic acid (154 mg). This mixture was heated at 70° C. for 3 hrs. After cooling, the reaction was quenched with water and extracted with $CH_2Cl_2$. The organic layer was washed with $NaHCO_3$ solution and brine. The organic layer was dried, filtered, and concentrated. Flash chromatography of the resulting residue gave the (3R)-biaryl 8 ($R^2$, $R^3$=H, R=3,4-dimethoxyphenyl; $R^{10}$=t-Bu; n=2) (40 mg). MS found: $(M+Na)^+$=484.2.

(14e) The (3R)-biaryl 8 ($R^2$, $R^3$=H, R=3,4-dimethoxyphenyl; $R^{10}$=t-Bu; n=2) (40 mg) was dissolved in $CH_2Cl_2$ (3 mL) prior to the addition of TFA (0.6 mL). After 5 h, the solution was concentrated. The resulting residue was dissolved in DMF and 4-methylmorpholine (0.32 mL) was added. After cooling to −22° C., the solution was treated with n-propyl chloroformate (0.22 mL). After an additional 30 min, a mixture of $H_2NOHHCl$ (267 mg) and 4-methylmorpholine (0.53 mL) in DMF was added. This mixture was stirred an additional 30 min and then was warmed to rt over 1 h. This material was filtered and reverse phase HPLC purification (gradient elution, water/acetonitrile/TFA) provided the title hydroxamic acid 9 ($R^2$, $R^3$=H, R=3,4-dimethoxyphenyl; n=2) (8 mg). MS found: $(M+H)^+$=386.1.

Example 15

(3R)-N-hydroxy-2-((4'-methoxy[1,1'-biphenyl]-4-yl)methyl)tetrahydro-2H-1,2-thiazine-3-carboxamide 1,1-dioxide (15a) 4-Methoxybenzeneboronic acid (128 mg) was incorporated into the above procedures, (14d)–(14e), to give the title hydroxamate 9 ($R^2$, $R^3$=H, R=4-methoxyphenyl; n=2) (32 mg). MS found: $(M+H)^+$=391.3.

Example 16

(3R)-N-hydroxy-2-((4'-trifluoromethyl[1,1'-biphenyl]-4-yl)methyl)tetrahydro-2H-1,2-thiazine-3-carboxamide 1,1-dioxide (16a) 4-Trifluoromethylbenzeneboronic acid (163 mg) was incorporated into the above procedures, (14d)–(14e), to give the title hydroxamate 9 ($R^2$, $R^3$=H, R=4-trifluoromethylphenyl; n=2) (11 mg). MS found: $(M−1)^+$=427.1.

Example 17

(3R)-N-hydroxy-2-((4'-tert-butyl[1,1'-biphenyl]-4-yl)methyl)tetrahydro-2H-1,2-thiazine-3-carboxamide 1,1-dioxide (17a) 4-Tertbutylbenzeneboronic acid (146 mg) was incorporated into the above procedures, (14d)–(14e), to give the title hydroxamate 9 ($R^2$, $R^3$=H, R=4-tert-butylphenyl; n=2) (30 mg). MS found: $(M-1)^-$=415.5.

Example 18

(3R)-N-hydroxy-2-((4'-chloro[1,1'-biphenyl]-4-yl) methyl)tetrahydro-2H-1,2-thiazine-3-carboxamide 1, 1-dioxide (18a) 4-Chlorobenzeneboronic acid (139 mg) was incorporated into the above procedures, (14d)–(14e), to give the title hydroxamate 9 ($R^2$, $R^3$=H, R=4-chlorophenyl; n=2) (39 mg). MS found: $(2M-1)^-$=787.3.

Example 19

(3R)-N-hydroxy-2-((4'-methylthio[1,1'-biphenyl]-4-yl)methyl)tetrahydro-2H-1,2-thiazine-3-carboxamide 1,1-dioxide (19a) 4-(Methylthio)benzeneboronic acid (367 mg) was incorporated into the above procedures, (14d)–(14e), to give the title hydroxamate 9 ($R^2$, $R^3$=H, R=4-methylthiophenyl; n=2) (65 mg). MS found: $(M-1)^-$=405.4.

Example 20

(3R)-N-hydroxy-2-((4'-methylsulfonyl[1,1'-biphenyl]-4-yl)methyl)tetrahydro-2H-1,2-thiazine-3-carboxamide 1,1-dioxide (20a) Some of the intermediate from (19a) (3R)-ester 8 ($R^2$, $R^3$=H, R=4-methylthiophenyl; $R^{10}$=t-Bu; n=2) (210 mg) was dissolved in $CH_2Cl_2$ and cooled to 0° C. MCPBA (202 mg) was added and the reaction was warmed to rt. After stirring overnight, the reaction was quenched with $NaHCO_3$ solution. The organic layer was washed with $NaHCO_3$ solution, $Na_2S_2O_3$ solution, and brine. This organic layer was dried, filtered, and concentrated. Flash chromatography of the resulting residue gave the (3R)-sulfone 8 ($R^2$, $R^3$=H, R=4-methanesulfonylphenyl; $R^{10}$=t-Bu; n=2) (40 mg). MS found: $(M-H)^-$=478.3.

(20b) The (3R)-sulfone 8 ($R^2$, $R^3$=H, R=4-methanesulfonylphenyl; $R^{10}$=t-Bu; n=2) (189 mg) was incorporated into the above procedure, (14e), to give the title hydroxamate 9 ($R^2$, $R^3$=H, R=4-methanesulfonylphenyl; n=2) (96 mg). MS found: $(2M+H)^+$=877.2.

Example 21

(3R)-N-hydroxy-2-((3',4'-dichloro[1,1'-biphenyl]-4-yl)methyl)tetrahydro-2H-1,2-thiazine-3-carboxamide 1,1-dioxide (21a) 3,4-Dichlorobenzeneboronic acid (168 mg) was incorporated into the above procedures, (14d)–(14e), to give the title hydroxamate 9 ($R^2$, $R^3$=H, R=3,4-dichlorophenyl; n=2) (12 mg). MS found: $(2M+Na)^+$=881.0.

Example 22

(3R)-N-hydroxy-2-((4'-methoxycarbonyl[1,1'-biphenyl]-4-yl)methyl)tetrahydro-2H-1,2-thiazine-3-carboxamide 1,1-dioxide (22a) 4-Methoxycarbonylbenzeneboronic acid (155 mg) was incorporated into the above procedures, (14d–(14e), to give the title hydroxamate 9 ($R^2$, $R^3$=H, R=4-methoxycarbonylphenyl; n=2) (40 mg). MS found: $(2M-1)^-$=835.2.

Example 23

(3R)-N-hydroxy-2-((3',4'-methylenedioxy[1,1'-biphenyl]-4-yl)methyl)tetrahydro-2H-1,2-thiazine-3-carboxamide 1,1-dioxide (23a) 3,4-Methylenedioxybenzeneboronic acid (139 mg) was incorporated into the above procedures, (14d)–(14e), to give the title hydroxamate 9 ($R^2$, $R^3$=H, R=3,4-methylenedioxyphenyl; n=2) (18 mg). MS found: $(M-1)^+$=403.3.

Example 24

(3R)-N-hydroxy-2-((4'-nitro[1,1'-biphenyl]-4-yl) methyl) tetrahydro-2H-1,2-thiazine-3-carboxamide 1,1-dioxide (24a) The (3R)-triflate 7 ($R^2$, $R^3$=H; R=t-Bu; n=2) (184 mg) was dissolved in DMF prior to the addition of $K_2CO_3$ (80 mg), Pd $(Ph_3)_4$ (13 mg), and 4-nitro-benzeneboronic acid (130 mg). This mixture was heated at 85° C. overnight. After cooling, the reaction was diluted with EtOAc and filtered. Flash chromatography gave the (3R)-biaryl 8 ($R^2$, $R^3$=H, R=4-nitrophenyl; $R^{10}$=t-Bu; n=2) (quant.). MS found: $(M+Na)^+$=445.2.

(24b) The (3R)-biaryl 8 ($R^2$, $R^3$=H, R=4-nitrophenyl; $R^{10}$= t-Bu; n=2) (220 mg) was incorporated into the above procedure, (14e), to give the title hydroxamate 9 ($R^2$, $R^3$=H, R=4-nitrophenyl; n=2) (10 mg). MS found: $(2M-1)^+$=809.5.

Example 25

(3R)-N-hydroxy-2-((4'-amino[1,1'-biphenyl]-4-yl) methyl)tetrahydro-2H-1,2-thiazine-3-carboxamide 1, 1-dioxide (25a) The material from above 9 (24b) ($R^2$, $R^3$=H, R=4-nitrophenyl; n=2) (16 mg) was dissolved in MeOH prior to the addition of 5% $Pd/BaSO_4$ (27 mg). A hydrogen balloon was added and the reaction was stirred for 30 min. The hydrogen was removed and the solution was filtered. The solution was concentrated give the title hydroxamate 9 ($R^2$, $R^3$=H, R=4-aminophenyl; n=2) (11 mg). MS found: $(M+1)^+$=398.1.

Example 26

(3R)-N-hydroxy-2-(4-(5-chloro-2-thienyl)benzyl) tetrahydro-2H-1,2-thiazine-3-carboxamide 1,1-dioxide (26a) The (3R)-sultam 3 ($R^2$, $R^3$=H; $R^{10}$=t-Bu; n=2) (2 g) was dissolved in DMF prior to the addition of $K_2CO_3$ (2.3 g) and 4-bromobenzyl bromide (4.2 g). After overnight at rt, the reaction was diluted with EtOAc and water. The organic layer was washed with additional brine (×2) and dried with $MgSO_4$. The filtered solution was concentrated. Flash chromatography of the resulting material gave the alkylated (3R)-sultam 16 ($R^2$, $R^3$=H; $R^{10}$=t-Bu; n=2) (3.2 g). MS found: $(M+H)^+$=405.1.

(26b) The (3R)-sultam 16 ($R^2$, $R^3$=H; $R^{10}$=t-Bu; n=2) was dissolved in DME prior to the addition of 2M $K_2CO_3$ (1 mL), P(o-tolyl)$_3$ (15 mg), $Pd(OAc)_2$ (6 mg), and 5-chlorothiophene-2-boronic acid (161 mg). This mixture was heated at 80° C. for 4 hrs. After cooling, the solution was filtered and concentrated. Flash chromatography of the resulting residue gave the (3R)-biaryl 8 ($R^2$, $R^3$=H, R=5-chloro-2-thiophene; $R^{10}$=t-Bu; n=2) (198 mg). $^1$H NMR (300 MHz, $CDCl_3$) ppm δ 1.47 (s, 9H), 1.65 (m, 1H), 2.1 (m, 2H), 2.55 (m, 1H), 3.05 (m, 1H), 3.15 (m, 1H), 3.88 (m, 1H), 4.43 (d, 1H), 4.76 (d, 1H), 6.88 (d, 1H), 7.08 (d, 1H), 7.39 (d, 2H), 7.48 (d, 2H).

(26c) The (3R)-biaryl 8 ($R^2$, $R^3$=H, R=5-chloro-2-thiophene; $R^{10}$=t-Bu; n=2) (189 mg) was incorporated into the above procedure, (14e), to give the title hydroxamate 9 ($R^2$, $R^3$=H, R=5-chloro-2-thiophene; n=2) (12 mg). MS found: $(2M-1)^+$=799.2.

Example 27

(3R)-N-hydroxy-2-(4-(3'-fluorobiphenyl)benzyl) tetrahydro-2H-1,2-thiazine-3-carboxamide 1,1-dioxide (27a) 3-Fluorobiphenyl-4-boronic acid (189 mg) was incorporated into the above procedures, (26b-26c), to give the title hydroxamate 9 (R$^2$, R$^3$=H, R=3-fluoro-4-biphenyl; n=2) (8 mg). MS found: (M−1)$^+$=453.1.

Example 28

(3R)-N-hydroxy-2-(4-(2-benzo[b]thiophene)benzyl) tetrahydro-2H-1,2-thiazine-3-carboxamide 1,1-dioxide (28a) Benzo[b]thiophene-2-boronic acid (176 mg) was incorporated into the above procedures, (26b-26c), to give the title hydroxamate 9 (R$^2$, R$^3$=H, R=2-benzo[b]thiophene; n=2) (7 mg). MS found: (M−1)$^+$=415.5.

Example 29

(3R)-N-hydroxy-2-(4-(3-formyl-2-thiophene)benzyl) tetrahydro-2H-1,2-thiazine-3-carboxamide 1,1-dioxide (29a) 3-Formylthiophene-2-boronic acid (153 mg) was incorporated into the above procedures, (26b-26c), to give the title hydroxamate 9 (R$^2$, R$^3$=H, R=[3′-formyl]-2-thiophene; n=2) (10 mg). MS found: (M−1)$^+$=415.5.

Example 30

(3R)-N-hydroxy-2-(4-(3-pyridinyl)benzyl) tetrahydro-2H-1,2-thiazine-3-carboxamide 1,1-dioxide (30a) The (3R)-sultam 16 (R$^2$, R$^3$=H; R$^{10}$=t-Bu; n=2) (200 mg) was dissolved in DMF prior to the addition of KOAc (144 mg) and bis(pinacolato)diboron (151 mg). After being flushed with nitrogen, PdCl$_2$(dppf) (12 mg) was added and the solution was heated at 80° C. After 2 h, the reaction was cooled to rt and 3-bromopyridine (155 mg), PdCl$_2$(dppf) (12 mg), and 2M Na$_2$CO$_3$ (1.2 mL) were added. The reaction was returned to 80° C. and was stirred overnight. After cooling, water and EtOAc were added. The organic layer was washed with addition water, brine, dried, and concentrated. Flash chromatography of the resulting residue gave the (3R)-biaryl 8 (R$^2$, R$^3$=H, R=3-pyridinyl; R$^{10}$=t-Bu; n=2) (120 mg). MS found: (M+H)$^+$=403.

(30b) The (3R)-biaryl 8 (R$^2$, R$^3$=H, R=3-pyridinyl; R$^{10}$=t-Bu; n=2) (110 mg) was incorporated into the above procedure, (14e), to give the title hydroxamate 9 (R$^2$, R$^3$=H, R=3-pyridinyl; n=2) (30 mg). MS found: (M+1)$^+$=362.

Example 31

(3R)-N-hydroxy-2-(4-(4-pyridinyl)benzyl) tetrahydro-2H-1,2-thiazine-3-carboxamide 1,1-dioxide (31a) 4-Bromopyridine hydrogen chloride (385 mg) was incorporated into the above procedures, (30a-30b), to give the title hydroxamate 9 (R$^2$, R$^3$=H, R=4-pyridinyl; n=2) (30 mg). MS found: (M+1)$^+$=362.

Example 32

(3R)-N-hydroxy-2-(4-(2-pyridinyl)benzyl) tetrahydro-2H-1,2-thiazine-3-carboxamide 1,1-dioxide (32a) 2-Bromopyridine hydrogen chloride (250 mg) was incorporated into the above procedures, (30a-30b), to give the title hydroxamate 9 (R$^2$, R$^3$=H, R=2-pyridinyl; n=2) (5 mg). MS found: (M+1)$^+$=362.2.

Example 33

(3R)-N-hydroxy-2-(4-(4-methoxy-3-pyridinyl) benzyl)tetrahydro-2H-1,2-thiazine-3-carboxamide 1,1-dioxide (33a) 4-methoxy-3-pyridinyl boronic acid (189 mg) was incorporated into the above procedures, (30a-30b), to give the title hydroxamate 9 (R$^2$, R$^3$=H, R=4-methoxy-3-pyridinyl; n=2) (5 mg). MS found: (M+1)$^+$=362.2.

Example 34

(3R)-N-hydroxy-2-{4-[(6-methoxy-3-pyridinyloxy] benzyl}tetrahydro-2H-1,2-thiazine-3-carboxamide 1,1-dioxide (34a) The (3R)-phenol 6 (R$^2$, R$^3$=H; R$^{10}$=t-Bu; n=2) (200 mg) was dissolved in CH$_2$Cl$_2$ along with Cu(OAc)$_2$ (236 mg), pyridine (0.23 mL), 4 Å molecular sieves (100 mg), and 4-methoxy-3-pyridinyl boronic acid (181 mg). The reaction was stirred in open air overnight. The reaction was concentrated and dried. Flash chromatography of the resulting residue gave the arylated (3R)-phenol 10 (R$^2$, R$^3$ H; R=4-methoxy-3-pyridinyl; R$^{10}$=t-Bu; n=2) (228 mg). MS found: (M+H)$^+$=449.2.

(34b) The arylated (3R)-phenol 10 (R$^2$, R$^3$=H; R=4-methoxy-3-pyridinyl; R$^{10}$=t-Bu; n=2) (228 mg) was dissolved in CH$_2$Cl$_2$ (3 mL) prior to the addition of TFA (3 mL). After 3 h, the solution was concentrated. The resulting residue was dissolved in THF prior to the addition of BnONH$_2$HCl (488 mg). After cooling to 0° C., EDC (312 mg) was added as a solution in H$_2$O/THF (1:1). This solution was warmed to rt and was stirred overnight. The reaction was quenched with 1 N HCl and EtOAc. The organic layer was dried, filtered and concentrated. The resuling residue was dissolved in MeOH prior to the addition of 5% Pd/BaSO$_4$ (200 mg). A hydrogen balloon was added, and the solution was stirred for 1 h. The hydrogen balloon was removed, and the solution was filtered and concentrated. This material was filtered and reverse phase HPLC purification (gradient elution, water/acetonitrile/TFA) provided the title hydroxamic acid 11 (R$^2$, R$^3$=H; R=4-methoxy-3-pyridinyl; n=2) (8 mg). MS found: (M+H)$^+$=408.1.

Example 35

N-hydroxy-2-{4-[(2-methyl-4-quinolinyl)methoxy] benzyl}-3-isothiazolidinecarboxamide 1,1-dioxide (35a) To a solution of the phenol 6 (R$^2$, R$^3$=H; R=H; R$^{10}$=Me; n=1) (350 mg) from reaction (5a), triphenylphosphine (656 mg), and (2-methylquinolin-4-yl)-methanol (432 mg) in THF (10 mL) at 0° C. was added diethyl azodicarboxylate (522 mg). The mixture was allowed to warm to rt overnight. The mixture was partitioned between ethyl acetate and H$_2$O and the layers separated. The organic layer was washed further with H$_2$O and brine, dried (MgSO$_4$), and concentrated in vacuo. Purification of the residue by silica gel column chromatography (1:1 ethyl acetate:hexanes) gave the desired ester 10 (R$^2$, R$^3$=H; R=(2-methyl-4-quinolinyl)methyl; R$^{10}$=Me; n=1) (353 mg, 65%). MS found: (M+H)$^+$=441.

(35b) Preparation of the hydroxylamine/sodium methoxide solution: Sodium methoxide (11.9 mL, 51.8 mmol), as a 25 w/w % solution in methanol, was added to a hot solution of hydroxylamine hydrochloride (2.40 g, 34.5 mmol) in methanol (9 mL). After the mixture cooled to rt, the precipitate was removed by filtration. The filtrate was used fresh and was assumed to have a hydroxylamine concentration of 1.64 M.

The basic hydroxylamine solution (4 mL, 1.64 M) was added to methyl ester 10 (R$^2$, R$^3$=H; R=(2-methyl-4-quinolinyl)methyl; R$^{10}$=Me; n=1) (350 mg). After stirring for 30 min at rt, the reaction was acidified to pH 7 with concentrated HCl. The mixture was filtered to remove the precipitated salts and the material purified by reverse phase HPLC (15–40% acetonitrile/water) to provide hydroxamic acid 11 (R$^2$, R$^3$=H; R=4-[(2-methyl-4-quinolinyl)methoxy] benzyl; n=1) (83 mg, 19%). MS found: (M+H)$^+$=442.

Example 36

N-hydroxy-2-{4-[(2-methyl-4-quinolinyl)methoxy]phenyl}-3-isothiazolidinecarboxamide 1,1 dioxide (36a) The sultam 3 ($R^2$, $R^3$=H; $R^{10}$=Me; n=1) (96 mg) was dissolved in methylene chloride along with copper (II) acetate (97 mg), triethylamine (271 mg), 4 Å molecular sieves (140 mg), and 4-benzyloxybenzeneboronic acid (244 mg). The reaction was stirred open to air overnight. The mixture was filtered and concentrated. Purification of the crude material by silica gel chromatography (25–75% ethyl acetate/hexanes) provided the sulfonamide 4 ($R^2$, $R^3$=H; R=4-benzyloxyphenyl; $R^{10}$=Me; n=1) (50 mg, 26%). MS found: $(M+H)^+$=362.

(36b) The sulfonamide 4 ($R^2$, $R^3$=H; R=4-benzyloxyphenyl; $R^{10}$=Me; n=1) (50 mg) was dissolved in methanol prior to the addition of 20% Pd(OH)$_2$/C (5 mg). A hydrogen balloon was added, and the solution was stirred overnight. The hydrogen balloon was removed, and the solution was filtered and concentrated. This gave the phenol 4 ($R^2$, $R^3$=H; R=4-hydroxyphenyl; $R^{10}$=Me; n=1) (quant.) ready for subsequent reactions. MS found: $(M+H)^+$=272.

(36c) A solution of phenol 4 ($R^2$, $R^3$=H; R=4-hydroxyphenyl; $R^{10}$=Me; n=1) (50 mg), potassium carbonate (57 mg), and 2-methyl-4-chloromethylquinoline (26 mg) in acetonitrile was heated at reflux for 2 hr. The solution was cooled to rt, filtered, and concentrated. The material was purified by reverse phase HPLC (15–40% acetonitrile/water) to provide ester 4 ($R^2$, $R^3$=H; R=4-[(2-methyl-4-quinolinyl)methoxy]phenyl; $R^{10}$=Me; n=1) (40 mg) MS found: $(M+H)^+$=427.

(36d) The ester 4 ($R^2$, $R^3$=H; R=4-[(2-methyl-4-quinolinyl)methoxy]phenyl; $R^{10}$=Me; n=1) (40 mg) was treated as in (35b) to yield the title hydroxamate 5 ($R^2$, $R^3$=H; R=4-[(2-methyl-4-quinolinyl)methoxy]phenyl; n=1) (30 mg). MS found: $(M+H)^+$=428.

Example 37

N-hydroxy-2-(2-{4-[(2-methyl-4-quinolinyl)methoxy]phenyl}ethyl)-3-isothiazolidinecarboxamide 1,1-dioxide (37a) To a solution of sodium hydride (35 mg, 60% dispersion in mineral oil) in THF/DMF (1:1) was added sulfonamide 3 ($R^2$, $R^3$=H; $R^{10}$=Me; n=1) (150 mg). After 15 min, 2-(4-benzyloxyphenyl)ethyl bromide was added and the mixture heated at 75° C. for 2 h. The solution was cooled and diluted with ethyl acetate. The organic layer was washed with H$_2$O and brine (2×), dried, and concentrated. This gave the benzyl ether 4 ($R^2$, $R^3$=H; R=2-(4-benzyloxyphenyl)ethyl; $R^{10}$=Me; n=1) (241 mg) ready for subsequent reactions. MS found: $(M+H)^+$=390.

(37b) The benzyl ether 4 ($R^2$, $R^3$=H; R=2-(4-benzyloxyphenyl)ethyl; $R^{10}$=Me; n=1) (241 mg) was treated as in (36b) to yield the phenol 4 ($R^2$, $R^3$=H; R=2-(4-hydroxyphenyl)ethyl; $R^{10}$=Me; n=1) (185 mg). MS found: $(M+H)^+$=300.

(37c) The phenol 4 ($R^2$, $R^3$=H; R=2-(4-hydroxyphenyl)ethyl; $R^{10}$=Me; n=1) (185 mg) was treated as in (36c) to yield the quinoline 4 ($R^2$, $R^3$=H; R=2-{4-[2-methyl-4-quinolinyl)methoxy]phenyl}ethyl; $R^{10}$=Me; n=1) (142 mg). MS found: $(M+H)^+$=455.

(37d) The ester 4 ($R^2$, $R^3$=H; R=2-{4-[(2-methyl-4-quinolinyl)methoxy]phenyl}ethyl; $R^{10}$=Me; n=1) (142 mg) was treated as in (35b) to yield the title hydroxamate 5 ($R^2$, $R^3$=H; R=2-{4-[(2-methyl-4-quinolinyl)methoxy]phenyl}ethyl; n=1) (54 mg). MS found: $(M+H)^+$=456.

Example 38

N-hydroxy-2-{4-[(2-methyl-4-quinolinyl)methoxy]benzyl}tetrahydro-2H-1,2-thiazine-3-carboxamide 1,1-dioxide (38a) A solution of phenol 6 ($R^2$, $R^3$=H; R=H; $R^{10}$=t-Bu; n=2) (192 mg), potassium carbonate (207 mg), and 2-methyl-4-chloromethylquinoline hydrochloride (171 mg) in acetonitrile was heated at reflux overnight. The solution was cooled to rt, filtered, and concentrated. The crude material was purified by column chromatography (50% ethyl acetate/hexanes) to provide ester 10 ($R^2$, $R^3$=H; R=(2-methyl-4-quinolinyl)methyl; $R^{10}$=t-Bu; n=2) (226 mg) MS found: $(M+H)^+$=497.

(38b) To a solution of the t-butyl ester 10 ($R^2$, $R^3$=H; R=(2-methyl-4-quinolinyl)methyl; $R^{10}$=t-Bu; n=2) (220 mg) in methanol was bubbled HCl (g) for 15 min. The mixture was allowed to stir for 30 min and concentrated to give the methyl ester 10 ($R^2$, $R^3$=H; R=(2-methyl-4-quinolinyl)methyl; $R^{10}$=Me; n=2) (200 mg). MS found: $(M+H)^+$=455.

(38c) The ester 10 ($R^2$, $R^3$=H; R=(2-methyl-4-quinolinyl)methyl; $R^{10}$=Me; n=2) (200 mg) was treated as in (35b) to yield the title hydroxamate 11 ($R^2$, $R^3$=H; R=(2-methyl-4-quinolinyl)methyl; n=2) (102 mg). MS found: $(M+H)^+$=456.

Example 39

N-hydroxy-2-{4[(2-methyl-4-quinolinyl)methoxy]phenyl}tetrahydro-2H-1,2-thiazine-3-carboxamide 1,1-dioxide (39a) The sultam 3 ($R^2$, $R^3$=H; $R^{10}$=t-Bu; n=2) (198 mg) was dissolved in methylene chloride along with copper (II) acetate (153 mg), triethylamine (426 mg), 4 Å molecular sieves (180 mg), and 4-benzyloxybenzeneboronic acid (384 mg). The reaction was stirred open to air for 3 days. The mixture was filtered and concentrated. Purification of the crude material by silica gel chromatography (10–45% ethyl acetate/hexanes) provided the sulfonamide 4 ($R^2$, $R^3$=H; R=4-benzyloxyphenyl; $R^{10}$=t-Bu; n=2) (190 mg, 54%). MS found: $(M+Na+MeCN)^+$=481.

(39b) The sulfonamide 4 ($R^2$, $R^3$=H; R=4-benzyloxyphenyl; $R^{10}$=t-Bu; n=2) (190 mg) was dissolved in methanol prior to the addition of 20% Pd(OH)$_2$/C (20 mg). A hydrogen balloon was added, and the solution was stirred overnight. The hydrogen balloon was removed, and the solution was filtered and concentrated. This gave the phenol 4 ($R^2$, $R^3$=H; R=4-hydroxyphenyl; $R^{10}$=t-Bu; n=2) (quant.) ready for subsequent reactions. MS found: $(M+Na+MeCN)^+$=391.

(39c) A solution of phenol 4 ($R^2$, $R^3$=H; R=4-hydroxyphenyl; $R^{10}$=t-Bu; n=2) (149 mg), potassium carbonate (314 mg), and 2-methyl-4-chloromethylquinoline (87 mg) in acetonitrile was heated at reflux for 2 hr. The solution was cooled to rt, filtered, and concentrated. The crude material was purified by silica gel chromatography (20–65% acetonitrile/water) to provide ester 4 ($R^2$, $R^3$=H; R=4-[(2-methyl-4-quinolinyl)methoxy]phenyl; $R^{10}$=t-Bu; n=2) (140 mg) MS found: $(M+H)^+$=483.

(39d) To a solution of ester 4 ($R^2$, $R^3$=H; R=4-[(2-methyl-4-quinolinyl)methoxy]phenyl; $R^{10}$=t-Bu; n=2) (140 mg) in methanol was added thionyl chloride (3.0 g). The mixture was allowed to stir for 1 h and concentrated to give methyl ester 4 ($R^2$, $R^3$=H; R=4-[(2-methyl-4-quinolinyl)methoxy]phenyl; $R^{10}$=Me; n=2) (quant.). MS found: $(M+H)^+$=441.

(39e) The ester 4 ($R^2$, $R^3$=H; R=4-[(2-methyl-4-quinolinyl)methoxy]phenyl; $R^{10}$=Me; n=2) (128 mg) was treated as in (35b) to yield the title hydroxamate 5 ($R^2$, $R^3$=H; R=4-[(2-methyl-4-quinolinyl)methoxy]phenyl; n=2) (15 mg). MS found: $(M+H)^+$=442.

Example 40

N-hydroxy-2-{4-[(2-methyl-4-quinolinyl)methoxy]benzyl}tetrahydro-3-thiophenecarboxamide 1,1-dioxide (40a) To a solution of bis-(trimethylsilyl)methyl (trimethylsilyl)methyl sulfide (4.13 g) in THF was added tetramethylethylenediamine (1.70 g) followed by n-butyllithium (11 mL of a 1.6 M solution in hexanes). After stirring for 1 h, 4-benzyloxybenzaldehyde (3.14 g) was added and the resulting mixture was stirred for 1 h. The reaction was quenched with $H_2O$ and extracted with ethyl acetate. The organic layer was dried and concentrated. Purification of the crude material by silica gel chromatography (100% hexanes) provided olefin 87 (R=benzyl) (5.9 g). MS found: $(M+H)^+=401$.

(40b) To a solution of sulfide 87 (R=benzyl) (5.9 g) in methylene chloride at −40° C. was added m-chloroperoxybenzoic acid (3.0 g). After 2 h, 500 mg more of m-chloroperoxybenzoic acid was added and the resulting mixture was stirred for an additional hour. The solution was filtered and the organic layer washed with saturated sodium bicarbonate solution, dried, and concentrated. This provided sulfoxide 88 (R=benzyl) (6.16 g) which was ready for subsequent reactions. MS found: $(M+H)^+=417$.

(40c) A solution of sulfoxide 88 (R=benzyl) (6.16 g) and methyl acrylate (2.09 g) in hexamethylphosphoramide was heated at 100° C. for 40 min. The solution was cooled to rt and diluted with ethyl acetate. The organic layer was washed with saturated potassium dihydrogenphosphate, dried, and concentrated. Purification of the crude material by silica gel chromatography (hexanes-10% ethyl acetate/hexanes) provided an inseparable mixture of sulfide 89 ($R^2$ H; R=benzyl; $R^{10}$=Me) and the regioisomeric cycloaddition product (1.0 g). MS found: $(M+H)^+=341$.

(40d) To a solution of sulfide 89 ($R^2$=H; R=benzyl; $R^{10}$=Me) (1.0 g, contaminated with regioisomer from 40c) in methylene chloride, methanol, and water was added oxone (5.0 g). The mixture was stirred for 4 h prior to quenching with saturated sodium bisulfite. The mixture was diluted with additional methylene chloride and the layers separated. The organic layer was dried and concentrated. Purification of the crude material by silica gel chromatography (33% ethyl acetate/hexanes) provided sulfone 90 ($R^2$=H; R=benzyl; $R^{10}$=Me) (470 mg, contaminated with regioisomer from 40c). MS found: $(M+H)^+=373$.

(40e) The sulfone 90 ($R^3$=H; R=benzyl; $R^3$=Me) (470 mg, contaminated with regioisomer from 40c) was dissolved in methanol prior to the addition of 20% $Pd(OH)_2/C$ (40 mg). The solution was pressurized with 50 psi of $H_2$, and was shaken overnight. The solution was filtered and concentrated. This gave the phenol 91 ($R^2$=H; R=H; $R^{10}$=Me) (62 mg) ready for subsequent reactions. MS found: $(M+H)^+=285$.

(40f) The phenol 91 ($R^2$=H; R=H; $R^{10}$=Me) (62 mg) was treated as in (35a) to yield the sulfone 92 ($R^2$=H; R=(2-methyl-4-quinolinyl)methyl; $R^{10}$=Me) (73 mg). MS found: $(M+H)^+=440$.

(40g) The sulfone 92 ($R^2$=H; R=(2-methyl-4-quinolinyl)methyl; $R^{10}$=Me) (73 mg) was treated as in (35b) to yield the title hydroxamate 93 ($R^2$=H; R=(2-methyl-4-quinolinyl)methyl) (26 mg). MS found: $(M+H)^+=441$.

Example 41

N-hydroxy-2-{4-[(2-methyl-4-quinolinyl)methoxy]phenyl}-1,2,5-thiadiazolidine-3-carboxamide 1,1-dioxide (41a) To a solution of chlorosulfonyl isocyanate 94 (2.07 g) in methylene chloride was added t-butanol (1.09 g) at 0° C. After 30 min, triethylamine (3.05 g) was added followed by the dropwise addition of benzyl protected amine 95 ($R^2$=H; $R^{10}$=Me). The mixture was allowed to warm to rt and stir for 2 h. The mixture was diluted with additional methylene chloride and washed with 0.1 N HCl. The organic layer was dried and concentrated. Purification of the crude material by silica gel chromatography (25% ethyl acetate/hexanes) provided sulfonyl urea 96 ($R^2$=H; $R^{10}$=Me) (3.0 g, 53%). MS found: $(M+H)^+=389$.

(41b) To a solution of sulfonyl urea 96 ($R^2$=H; $R^{10}$=Me) (2.2 g) and triphenylphosphine (2.26 g) in methylene chloride was added diisopropyl azodicarboxylate (1.75 g). The mixture was allowed to stir for 2 h. The solvent was removed in vacuo and the residue diluted with diethyl ether. The insoluble material was removed by filtration and the filtrate concentrated. Purification of the crude product by silica gel chromatography (25% ethyl acetate/hexanes) gave cyclic sulfonyl urea 97 ($R^2$=H; $R^{10}$=Me) (1.4 g, 67%). MS found: $(M+H)^+=371$.

(41c) The benzyl sulfonamide 97 ($R^2$=H; $R^{10}$=Me) (1.4 g) was treated as in (40e) to yield the sulfonyl urea 98 ($R^2$=H; $R^{10}$=Me) (273 mg, 26%). MS found: $(M+H)^+=281$.

(41d) The sulfonyl urea 98 ($R^2$=H; $R^{10}$=Me) (273 mg) was dissolved in methylene chloride along with copper (II) acetate (182 mg), triethylamine (508 mg), 4 Å molecular sieves (180 mg), and 4-benzyloxybenzeneboronic acid (456 mg). The reaction was stirred open to air for 2 days. The mixture was filtered and concentrated. Purification of the crude material by silica gel chromatography (methylene chloride) provided the sulfonyl urea 103 ($R^2$=H; R=benzyl; $R^{10}$=Me) (93 mg, 20%). MS found: $(M+H)^+=463$.

(41e) The benzyl ether 103 ($R^2$=H; R=benzyl; $R^{10}$=Me) (93 mg) was treated as in (36b) to yield the phenol 104 ($R^2$=H; R=H; $R^{10}$=Me) (74 mg). MS found: $(M+H)^+=373$.

(41f) The phenol 104 ($R^2$=H; R=H; $R^{10}$=Me) (74 mg) was treated as in (35a) to yield the ether 105 ($R^2$=H; R=(2-methyl-4-quinolinyl)methyl; $R^{10}$=Me) (35 mg). MS found: $(M+H)^+=528$.

(41g) The ester 105 ($R^2$=H; R=(2-methyl-4-quinolinyl)methyl; $R^{10}$=Me) (35 mg) was treated as in (35b) to yield the title hydroxamate 108 ($R^2$, $R^3$=H; R=(2-methyl-4-quinolinyl)methyl) (8 mg). MS found: $(M+H)^+=429$.

TABLE 1

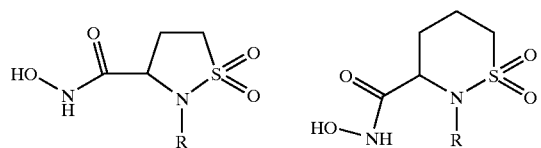

Example 1–12 and 35–37

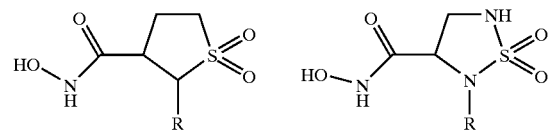

Example 40

Example 13–34 and 38–39

Example 41

| Ex | R | MS |
| --- | --- | --- |
| 1 | [1,1'-biphenyl]-4-ylmethyl | 399.1 |
| 2 | 2-[1,1'-biphenyl]-4-ylethyl | 383.1 |
| 3 | 2-phenylethyl | 306.1 |
| 4 | [1,1'-biphenyl]-4-yl | 333.2 |
| 5 | (4'methoxy-[1,1'-biphenyl]-4-yl)methyl | 751.4 |
| 6 | 4-(3-thienyl)benzyl | 703.2 |
| 7 | 4-(2-furyl)benzyl | |
| 8 | 4-phenoxybenzyl | 744.4 |
| 9 | 4-(4-methoxyphenoxy)benzyl | 783.4 |
| 10 | 4-[4-(trifluoromethyl)phenoxy]benzyl | 859.2 |

TABLE 1-continued

Example 1–12 and 35–37

Example 13–34 and 38–39

Example 40

Example 41

| Ex | R | MS |
|---|---|---|
| 11 | 4-(4-pyridinylmethoxy)benzyl | 378.2 |
| 12 | [1,1'-biphenyl]-4-ylmethyl | 347.1 |
| 13 | [1,1'-biphenyl]-4-ylmethyl | 361.2 |
| 14 | (3',4'-dimethoxy[1,1'-biphenyl]-4-yl)methyl | 386.1 |
| 15 | (4'-methoxy[1,1'-biphenyl]-4-yl)methyl | 391.3 |
| 16 | (4'-trifluoromethyl[1,1'-biphenyl]-4-yl)methyl | 427.1 |
| 17 | (4'-tert-butyl[1,1'-biphenyl]-4-yl)methyl | 415.5 |
| 18 | (4'-chloro[1,1'-biphenyl]-4-yl)methyl | 787.3 |
| 19 | (4'-methylthio[1,1'-biphenyl]-4-yl)methyl | 405.4 |
| 20 | (4'-methylsulfonyl[1,1'-biphenyl]-4-yl)methyl | 877.2 |
| 21 | (3',4'-dichloro[1,1'-biphenyl]-4-yl)methyl | 881.0 |
| 22 | (4'-methoxycarbonyl[1,1'-biphenyl]-4-yl)methyl | 835.2 |
| 23 | (3',4'-methylenedioxy[1,1'-biphenyl]-4-yl)methyl | 403.3 |
| 24 | (4'-nitro[1,1'-biphenyl]-4-yl)methyl | 809.5 |
| 25 | (4'-amino[1,1'-biphenyl]-4-yl)methyl | 398.1 |
| 26 | 4-(5-chloro-2-thienyl)benzyl | 799.2 |
| 27 | 4-(3'-fluorobiphenyl)benzyl | 453.1 |
| 28 | 4-(2-benzo[b]thiophene)benzyl | 415.5 |
| 29 | 4-(3-formyl-2-thiophene)benzyl | 415.5 |
| 30 | 4-(3-pyridinyl)benzyl | 362 |
| 31 | 4-(4-pyridinyl)benzyl | 362 |
| 32 | 4-(2-pyridinyl)benzyl | 362 |
| 33 | 4-(4-methoxy-3-pyridinyl)benzyl | 362.2 |
| 34 | 4-[(6-methoxy-3-pyridinyl)oxy]benzyl | 408.1 |
| 35 | 4-[(2-methyl-4-quinolinyl)methoxy]benzyl | 442 |
| 36 | 4-[(2-methyl-4-quinolinyl)methoxy]phenyl | 428 |
| 37 | 2-{4-[(2-methyl-4-quinolinyl)methoxy]phenyl}ethyl | 456 |
| 38 | 4-[(2-methyl-4-quinolinyl)methoxy]benzyl | 456 |
| 39 | 4[(2-methyl-4-quinolinyl)methoxy]phenyl | 442 |
| 40 | 4-[2-methyl-4-quinolinyl)methoxy]benzyl | 441 |
| 41 | 4-[(2-methyl-4-quinolinyl)methoxy]phenyl | 429 |

The following tables contain representative examples of the present invention. Each entry in each table is intended to be paired with each formula at the start of the table. For example, example 1 is intended to be paired with each of formulae A–Z.

TABLE 2

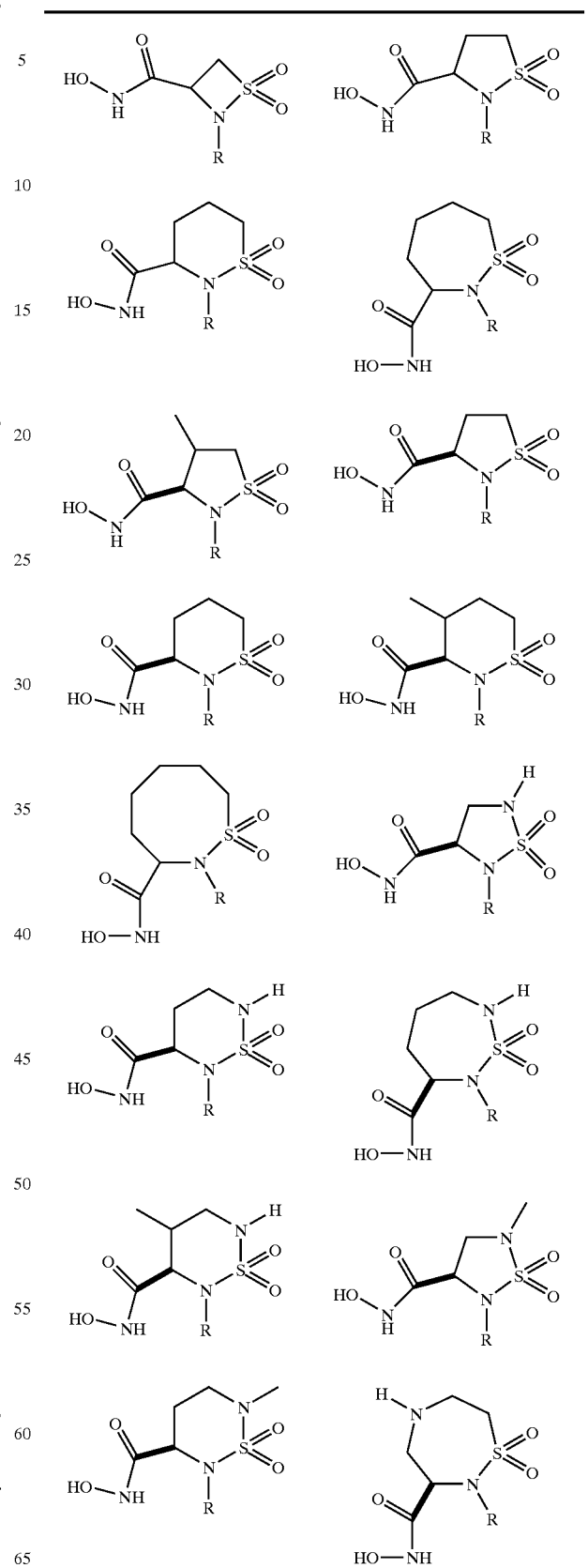

TABLE 2-continued
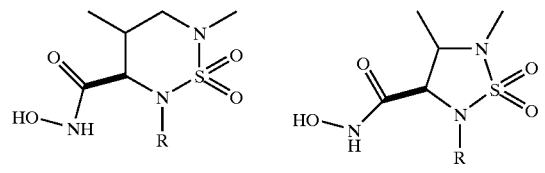
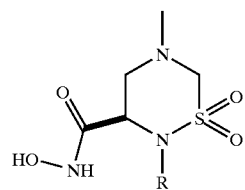
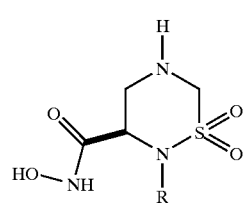
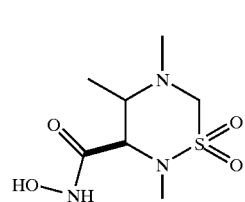
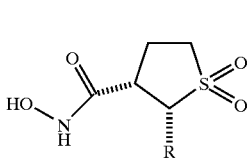
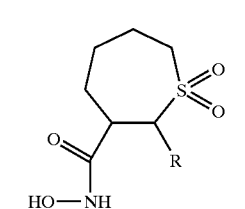
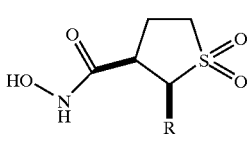
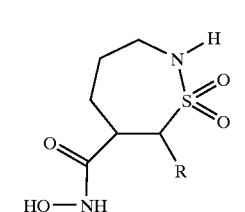
TABLE 2-continued
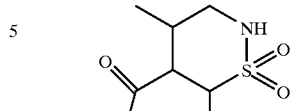
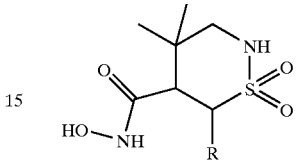
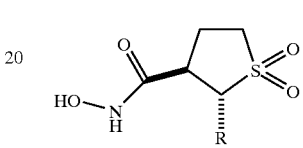
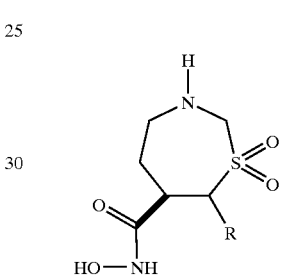
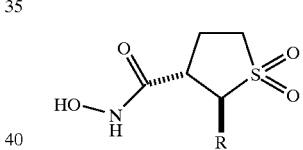
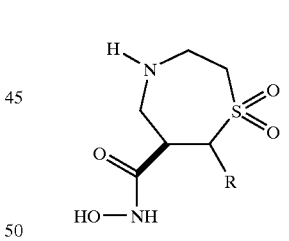
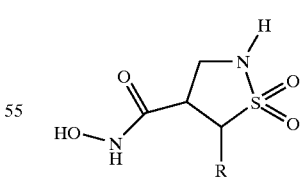
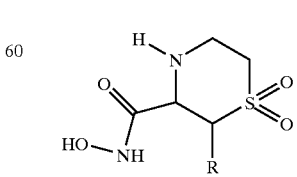

TABLE 2-continued

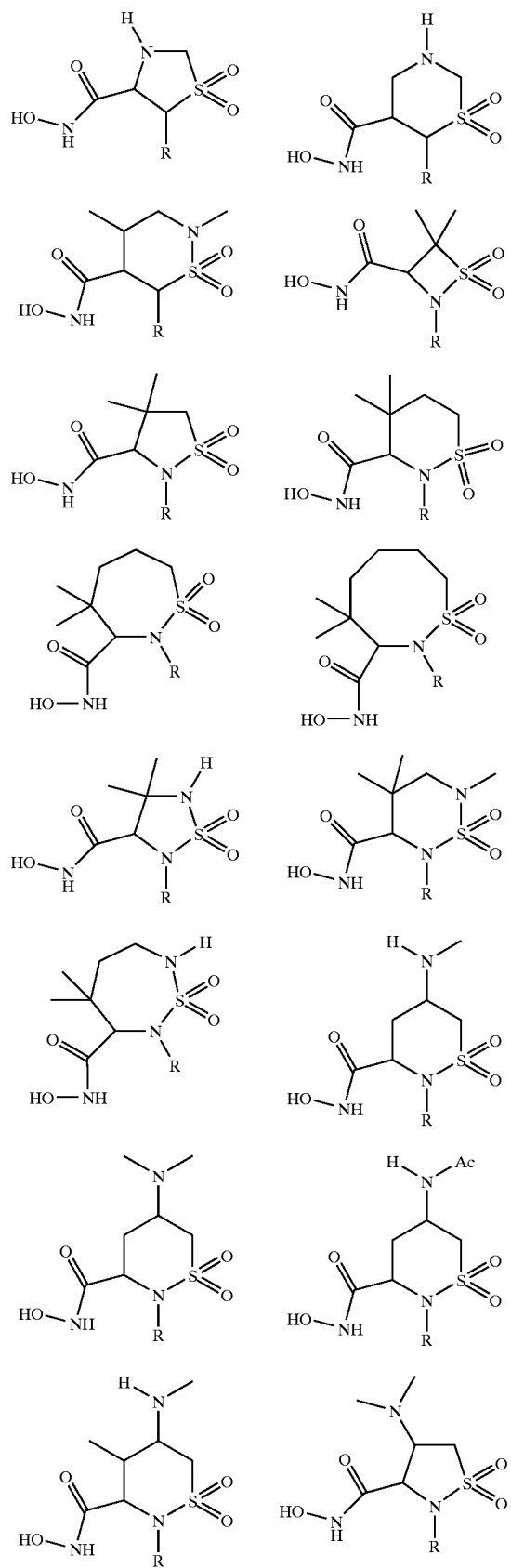

| Example # | R |
|---|---|
| 1. | 4-biphenylmethyl |
| 2. | 4-(4-methoxyphenyl)benzyl |
| 3. | 4-(4-trifluoromethylphenyl)benzyl |
| 4. | 4-(4-aminophenyl)benzyl |
| 5. | 4-(4-nitrophenyl)benzyl |
| 6. | 4-(4-methylthiophenyl)benzyl |
| 7. | 4-(4-methylsulfonylphenyl)benzyl |
| 8. | 4-(4-chlorophenyl)benzyl |
| 9. | 4-(4-tert-butylphenyl)benzyl |
| 10. | 4-(4-fluorophenyl)benzyl |
| 11. | 4-(4-methoxycarbonylphenyl)benzyl |
| 12. | 4-(3,4-methylenedioxyphenyl)benzyl |
| 13. | 4-(3,4-dichlorophenyl)benzyl |
| 14. | 4-(3-thienyl)benzyl |
| 15. | 4-(2-furyl)benzyl |
| 16. | 4-(3-formyl-2-thienyl)benzyl |
| 17. | 4-(5-chloro-2-thienyl)benzyl |
| 18. | 4-(2-benzothienyl)benzyl |
| 19. | 4-(4-pyridinyl)benzyl |
| 20. | 4-(3-pyridinyl)benzyl |
| 21. | 4-(2-pyridinyl)benzyl |
| 22. | 4-(6-methoxy-3-pyridinyl)benzyl |
| 23. | 4-[(6-methoxy-3-pyridinyl)oxy]benzyl |
| 24. | 4-(3,4-dimethoxyphenyl)benzyl |
| 25. | 4-(4-phenoxy)benzyl |
| 26. | 4-(benzyloxy)benzyl |
| 27. | 4-phenethyl |
| 28. | 4-biphenylethyl |
| 29. | 4-(4-methylphenyl)benzyl |
| 30. | 4-(4-pyridinylmethoxy)benzyl |
| 31. | 4-(4-pyridinyloxy)benzyl |
| 32. | 4-(4-methoxyphenoxy)benzyl |
| 33. | 4-(4-trifluoromethylphenoxy)benzyl |
| 34. | biphenyl |
| 35. | 4-(4-ethoxyphenoxy)benzyl |
| 36. | 4-(5-quinolinyl)benzyl |
| 37. | 4-(4-pyridinyloxy)benzyl |
| 38. | 4-(4-cyanophenoxy)benzyl |
| 39. | 4-(4-bromophenyl)benzyl |
| 40. | 4-(4-bromophenoxy)benzyl |
| 41. | 4-(4-cyanophenoxy)benzyl |
| 42. | 4-(4-fluorophenoxy)benzyl |
| 43. | 4-(3,4-difluorophenyl)benzyl |
| 44. | 4-(phenoxymethyl)benzyl |
| 45. | 4-(3,4-dibromophenyl)benzyl |
| 46. | 4-(4-methoxy-phenoxymethyl)benzyl |
| 47. | 4-(4-chloro-phenoxymethyl)benzyl |

TABLE 2-continued

| | |
|---|---|
| 48. | 4-(4-iso-butylphenyl)benzyl |
| 49. | 4-(4-iso-propylphenyl)benzyl |
| 50. | 4-(4-chloro-phenoxymethyl)benzyl |
| 51. | 4-(4-methylphenyl)benzyl |
| 52. | 4-(4-aminophenoxy)benzyl |
| 53. | 4-(4-chloro-benzyloxy)benzyl |
| 54. | 4-(4-amino-benzyloxy)benzyl |
| 55. | 4-(4-fluoro-benzyloxy)benzyl |
| 56. | 4-(phenmethyl)benzyl |
| 57. | 4-(4-pyridinylmethyl)benzyl |
| 58. | 4-(4-methoxy-phenmethyl)benzyl |
| 59. | 4-(4-fluoro-phenmethyl)benzyl |
| 60. | 4-(4-amino-phenmethyl)benzyl |
| 61. | 4-(4-pyridinylethyl)benzyl |
| 62. | 4-(phenethyl)benzyl |

Utility

The compounds of formula I are expected to possess matrix metalloprotease and/or aggrecanase and/or TNF-α and/or ADAM inhibitory activity. The MMP inhibitory activity of the compounds of the present invention is demonstrated using assays of MMP activity, for example, using the assay described below for assaying inhibitors of MMP activity. The compounds of the present invention are expected to be bioavailable in vivo as demonstrated, for example, using the ex vivo assay described below. The compounds of formula I are expected to have the ability to suppress/inhibit cartilage degradation in vivo, for example, as demonstrated using the animal model of acute cartilage degradation described below.

The compounds provided by this invention should also be useful as standards and reagents in determining the ability of a potential pharmaceutical to inhibit MPs. These would be provided in commercial kits comprising a compound of this invention.

Metalloproteases have also been implicated in the degradation of basement membranes to allow infiltration of cancer cells into the circulation and subsequent penetration into other tissues leading to tumor metastasis (Stetler-Stevenson, Cancer and Metastasis Reviews, 9, 289–303, 1990). The compounds of the present invention should be useful for the prevention and treatment of invasive tumors by inhibition of this aspect of metastasis.

The compounds of the present invention should also have utility for the prevention and treatment of osteopenia associated with matrix metalloprotease-mediated breakdown of cartilage and bone which occurs in osteoporosis patients.

Compounds that inhibit the production or action of TNF and/or Aggrecanase and/or MMP's are potentially useful for the treatment or prophylaxis of various inflammatory, infectious, immunological or malignant diseases or conditions. Thus, the present invention relates to a method of treating various inflammatory, infectious, immunological or malignant diseases. These include acute infection, acute phase response, age related macular degeneration, alcoholism, allergy, allergic asthma, aneurism, anorexia, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

As used herein "µg" denotes microgram, "mg" denotes milligram, "g" denotes gram, "µL" denotes microliter, "mL" denotes milliliter, "L" denotes liter, "nM" denotes nanomolar, "µM" denotes micromolar, "mM" denotes millimolar, "M" denotes molar and "nm" denotes nanometer. "Sigma2 stands for the Sigma-Aldrich Corp. of St. Louis, Mo.

A compound is considered to be active if it has an $IC_{50}$ or $K_i$ value of less than about 10 µM for the inhibition of a desired MP. Preferred compounds of the present invention have $K_i$'s or $IC_{50}$'s of ≦1 µM. More preferred compounds of the present invention have $K_i$'s or $IC_{50}$'s of ≦0.1 µM. Even more preferred compounds of the present invention have $K_i$'s or $IC_{50}$'s of ≦0.01 µM. Still more preferred compounds of the present invention have $K_i$'s or $IC_{50}$'s of ≦0.001 µM. Some compounds of the present invention have been shown to be active against an MMP, ADAM, TNF, and/or aggrecanase.

Aggrecanase Enzymatic Assay

A novel enzymatic assay was developed to detect potential inhibitors of aggrecanase. The assay uses active aggrecanase accumulated in media from stimulated bovine nasal cartilage (BNC) or related cartilage sources and purified cartilage aggrecan monomer or a fragment thereof as a substrate.

The substrate concentration, amount of aggrecanases time of incubation and amount of product loaded for Western analysis were optimized for use of this assay in screening putative aggrecanase inhibitors. Aggrecanase is generated by stimulation of cartilage slices with interleukin-1 (IL-1), tumor necrosis factor alpha (TNF-α) or other stimuli. Matrix metalloproteases (MMPs) are secreted from cartilage in an inactive, zymogen form following stimulation, although active enzymes are present within the matrix. We have shown that following depletion of the extracellular aggrecan matrix, active MMPs are released into the culture media (Tortorella, M. D. et. al. Trans. Ortho. Res. Soc. 20, 341, 1995). Therefore, in order to accumulate BNC aggrecanase in culture media, cartilage is first depleted of endogenous aggrecan by stimulation with 500 ng/ml human recombinant IL-β for 6 days with media changes every 2 days. Cartilage is then stimulated for an additional 8 days without media change to allow accumulation of soluble, active aggrecanase in the culture media. In order to decrease the amount of other matrix metalloproteases released into the media during aggrecanase accumulation, agents that inhibit MMP-1, -2, -3, and-9 biosynthesis are included during stimulation. This BNC conditioned media, containing aggrecanase activity is then used as the source of aggrecanase for the assay. Aggrecanase enzymatic activity is detected by monitoring production of aggrecan fragments produced exclusively by cleavage at the Glu373-Ala374 bond within the aggrecan core protein by Western analysis using the monoclonal antibody, BC-3 (Hughes, CE, et al., Biochem J 306:799–804, 1995). This antibody recognizes aggrecan fragments with the N-terminus, 374ARGSVIL, generated upon cleavage by aggrecanase. The BC-3 antibody recognizes this neoepitope only when it is at the N-terminus and not when it is present internally within aggrecan fragments or within the aggrecan protein core. Other proteases produced by cartilage in response to IL-1 do not cleave aggrecan at the Glu373-Ala374 aggrecanase site; therefore, only products produced upon cleavage by aggrecanase are detected. Kinetic studies using this assay yield a Km of 1.5+/−0.35 uM for aggrecanase.

To evaluate inhibition of aggrecanase, compounds are prepared as 10 mM stocks in DMSO, water or other solvents and diluted to appropriate concentrations in water. Drug (50 ul) is added to 50 ul of aggrecanase-containing media and 50 ul of 2 mg/ml aggrecan substrate and brought to a final volume of 200 ul in 0.2 M Tris, pH 7.6, containing 0.4 M NaCl and 40 mM $CaCl_2$. The assay is run for 4 hr at 37° C., quenched with 20 mM EDTA and analyzed for aggrecanase-generated products. A sample containing enzyme and substrate without drug is included as a positive control and enzyme incubated in the absence of substrate serves as a measure of background.

Removal of the glycosaminoglycan side chains from aggrecan is necessary for the BC-3 antibody to recognize the ARGSVIL epitope on the core protein. Therefore, for analysis of aggrecan fragments generated by cleavage at the Glu373-Ala374 site, proteoglycans and proteoglycan fragments are enzymatically deglycosylated with chondroitinase ABC (0.1 units/10 ug GAG) for 2 hr at 37° C. and then with keratanase (0.1 units/10 ug GAG) and keratanase II (0.002 units/10 ug GAG) for 2 hr at 37° C. in buffer containing 50 mM sodium acetate, 0.1 M Tris/HCl, pH 6.5. After digestion, aggrecan in the samples is precipitated with 5 volumes of acetone and resuspended in 30 ul of Tris glycine SDS sample buffer (Novex) containing 2.5% beta mercaptoethanol. Samples are loaded and then separated by SDS-PAGE under reducing conditions with 4–12% gradient gels, transferred to nitrocellulose and immunolocated with 1:500 dilution of antibody BC3. Subsequently, membranes are incubated with a 1:5000 dilution of goat anti-mouse IgG alkaline phosphatase second antibody and aggrecan catabolites visualized by incubation with appropriate substrate for 10–30 minutes to achieve optimal color development. Blots are quantitated by scanning densitometry and inhibition of aggrecanase determined by comparing the amount of product produced in the presence versus absence of compound.

PBMC Assay

Human peripheral blood mononuclear cells (PBMC) were obtained from normal donor blood by leukophoresis and isolated by Ficoll-Paque density separation. PBMCs were suspended in 0.5 ml RPMI 1640 with no serum at $2 \times 10^6$ cells/ml in 96 well polystyrene plates. Cells were preincubated 10 minutes with compound, then stimulated with 1 μg/ml LPS(Lipopolysaccharide, Salmonella typhimurium) to induce TNF production. After an incubation of 5 hours at 37° C. in 95% air, 5% $CO_2$ environment, culture supernatants were removed and tested by standard sandwich ELISA for TNF production.

TNF Human Whole Blood Assay

Blood is drawn from normal donors into tubes containing 143 USP units of heparin/10 ml. 225 μl of blood is plated directly into sterile polypropylene tubes. Compounds are diluted in DMSO/serum free media and added to the blood samples so the final concentration of compounds are 50, 10, 5, 1, 0.5, 0.1, and 0.01 μM. The final concentration of DMSO does not exceed 0.5%. Compounds are preincubated for 15 minutes before the addition of 100 ng/ml LPS. Plates are incubated for 5 hours in an atmosphere of 5% $CO_2$ in air. At the end of 5 hours, 750 ul of serum free media is added to each tube and the samples are spun at 1200 RPM for 10 minutes. The supernatant is collected off the top and assayed for TNF-alpha production by a standard sandwich ELISA. The ability of compounds to inhibit TNF-alpha production by 50% compared to DMSO treated cultures is given by the $IC_{50}$ value.

MMP Assays

The enzymatic activities of recombinant MMP-1, 2, 3, 7, 8, 9, 13, 14, and 15 were measured at 25° C. with a fluorometric assay (Copeland, R. A.; Lombardo, D.; Giannaras, J. and Decicco, C. P. *Bioorganic Med. Chem. Lett.* 1995, 5, 1947–1952). Final enzyme concentrations in the assay were between 0.05 and 10 nM depending on the enzyme and the potency of the inhibitor tested. The permissive peptide substrate, MCA-Pro-Leu-Gly-Leu-DPA-Ala-Arg-$NH_2$, was present at a final concentration of 10 uM in all assays. Initial velocities, in the presence or absence of inhibitor, were measured as slopes of the linear portion of the product progress curves. $IC_{50}$ values were determined by plotting the inhibitor concentration dependence of the fractional velocity for each enzyme, and fitting the data by non-linear least squares methods to the standard isotherm equation (Copeland, R. A. *Enzymes: A practical Introduction to Structure, Mechanism and Data Analysis*, Wiley-VHC, New York, 1996, pp 187–223). All of the compounds studied here were assumed to act as competitive inhibitors of the enzyme, binding to the active site Zn atom as previously demonstrated by crystallographic studies of MMP-3 complexed with related hydroxamic acids (Rockwell, A.; Melden, M.; Copeland, R. A.; Hardman, K.; Decicco, C. P. and DeGrado, W. F. *J. Am. Chem. Soc.* 1996, 118, 10337–10338). Based on the assumption of competitive inhibiton, the IC50 values were converted to $K_i$ values as previously described.

Compounds tested in the above assays are considered to be active if they exhibit a $K_i$ of $\leq 10$ μM. Preferred compounds of the present invention have $K_i$'s of $\leq 1$ μM. More preferred compounds of the present invention have $K_i$'s of $\leq 0.1$ μM. Even more preferred compounds of the present invention have $K_i$'s of $\leq 0.01$ μM. Still more preferred compounds of the present invention have $K_i$'s of $\leq 0.001$ μM.

Using the methodology described above, a number of compounds of the present invention were found to exhibit $K_i$'s of $\leq 10$ μM, thereby confirming the utility of the compounds of the present invention.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiinflammatory and antiarthritic agent.

The compounds of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in Remington's Pharmaceutical Sciences, Mack Publishing Company, a standard reference text in this field. Useful pharmaceutical dosage-forms for administration of the compounds of this invention can be illustrated as follows:

Capsules

Capsules are prepared by conventional procedures so that the dosage unit is 500 milligrams of active ingredient, 100 milligrams of cellulose and 10 milligrams of magnesium stearate.

A large number of unit capsules may also prepared by filling standard two-piece hard gelatin capsules each with 100 milligrams of powdered active ingredient, 150 milligrams of lactose, 50 milligrams of cellulose, and 6 milligrams magnesium stearate.

| Syrup | |
|---|---|
| | Wt. % |
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

| Aqueous Suspension | |
|---|---|
| | Wt. % |
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

| Resuspendable Powder | |
|---|---|
| | Wt. % |
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

| Semi-Solid Gel | |
|---|---|
| | Wt. % |
| Active Ingredient | 10 |
| Sodium Saccharin | 0.02 |
| Gelatin | 2 |
| Flavor, Colorant and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

| Semi-Solid Paste | |
|---|---|
| | Wt. % |
| Active Ingredient | 10 |
| Gelcarin ® (Carrageenin gum) | 1 |
| Sodium Saccharin | 0.01 |
| Gelatin | 2 |
| Flavor, Colorant and Preservative | as required |
| Water | as required |

Gelcarin® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

| Emulsifiable Paste | |
|---|---|
| | Wt. % |
| Active Ingredient | 30 |
| Tween ® 80 and Span ® 80 | 6 |
| Keltrol ® | 0.5 |
| Mineral Oil | 63.5 |

All the ingredients are carefully mixed together to make a homogenous paste.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

Tablets may be prepared by conventional procedures so that the dosage unit is 500 milligrams of active ingredient, 150 milligrams of lactose, 50 milligrams of cellulose and 10 milligrams of magnesium stearate.

A large number of tablets may also be prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent, especially non-steroidal anti-inflammatory drugs (NSAID's). The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent may be administered essentially at the same time, or in any order; for example the compound of Formula I may be administered first, followed by administration of the second agent. When not administered at the same time, preferably the administration of the compound of Formula I and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above. Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the treatment or prevention of osteoarthritis or rheumatoid arthritis, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of formula I:

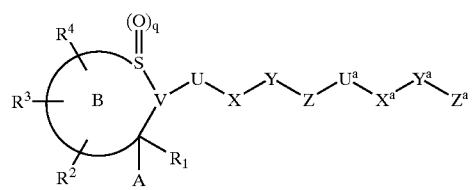

or a stereoisomer or pharmaceutically acceptable salt form thereof, wherein;

A is selected from —CONHOH, —CONHOR$^5$, —CONHOR$^6$, and —N(OH)COR$^5$;

V is N;

ring B, including V and S(O)$_q$, is a 5–6 membered non-aromatic heterocycle consisting of: S(O)$_q$, V, and carbon atoms;

U is absent or is selected from: O, $NR^{a1}$, C(O), C(O)O, OC(O), C(O)$NR^{a1}$, $NR^{a1}$C(O), OC(O)O, OC(O)$NR^{a1}$, $NR^{a1}$C(O)O, $NR^{a1}$C(O)$NR^{a1}$, S(O)$_p$, S(O)$_p NR^{a1}$, $NR^{a1}$S(O)$_p$, and $NR^{a1}$SO$_2 NR^{a1}$;

X is absent or selected from $C_{1-10}$ alkylene, $C_{2-10}$ alkenylene, and $C_{2-10}$ alkynylene;

Y is absent or is selected from: O, $NR^{a1}$, C(O), C(O)O, OC(O), C(O)$NR^{a1}$, $NR^{a1}$C(O), OC(O)O, OC(O)$NR^{a1}$, $NR^{a1}$C(O)O, $NR^{a1}$C(O)$NR^{a1}$, S(O)$_p$, S(O)$_p NR^{a1}$, $NR^{a1}$S(O)$_p$, and $NR^{a1}$SO$_2 NR^{a1}$;

Z is absent or selected from a $C_{3-13}$ carbocycle substituted with 0–5 $R^b$ and a 5–14 membered heterocycle consisting of: carbon atoms and 1–4 heteroatoms selected from the group consisting of N, O, and S and substituted with 0–5 $R^b$;

$U^a$ is absent or is selected from: O, $NR^{a1}$, C(O), C(O)O, OC(Q), C(O)$NR^{a1}$, $NR^{a1}$C(O), OC(O)O, OC(O)$NR^{a1}$, $NR^{a1}$C(O)O, $NR^{a1}$C(O)$NR^{a1}$, S(O)$_p$, S(O)$_p NR^{a1}$, $NR^{a1}$S(O)$_p$, and $NR^{a1}$SO$_2 NR^{a1}$;

$X^a$ is absent or selected from $C_{1-10}$ alkylene, $C_{2-10}$ alkenylene, and $C_{2-10}$ alkynylene;

$Y^a$ is absent or is selected from: O, $NR^{a1}$, C(O), C(O)O, OC(O), C(O)$NR^{a1}$, $NR^{a1}$C(O), OC(O)O, OC(O)$NR^{a1}$, $NR^{a1}$C(O)O, $NR^{a1}$C(O)$NR^{a1}$, S(O)$_p$, S(O)$_p NR^{a1}$, $NR^{a1}$S(O)$_p$, and $NR^{a1}$SO$_2 NR^{a1}$;

$Z^a$ is selected from a $C_{3-13}$ carbocycle substituted with 0–5 $R^c$ and a 5–14 membered heterocycle consisting of: carbon atoms and 1–4 heteroatoms selected from the group consisting of N, O, and S and substituted with 0–5 $R^c$;

provided that when U—X—Y are CH$_2$, $U^a$-$X^a$—$Y^a$ are absent, and Z is phenyl, then $Z^a$ is other than a 2-substituted phenyl ring or a 3,5-disubstituted phenyl ring;

provided that V, U, X, Y, Z, $U^a$, $X^a$, $Y^a$, $Z^a$, combine to form other than a N—N, N—O, O—N, O—O, S(O)$_p$—O, O—S(O)$_p$ or S(O)$_p$—S(O)$_p$ group, an unsubstituted naphthyl, a substituted naphthyl wherein the substituent is 1–3 atoms in length, an unsubstituted phenyl, a substituted phenyl wherein the substituent is 1–3 atoms in length, an unsubstituted benzyl, or a substituted benzyl wherein the substituent is 1–3 atoms in length;

$R^1$ is selected from H, $C_{1-6}$ alkyl, OR$^a$, NR$^a$R$^{a1}$, CN, CF$_3$, S(O)$_p$R$^a$, phenyl and benzyl;

$R^2$ is selected from Q, $C_{1-10}$ alkylene-Q substituted with 0–3 $R^{b1}$, $C_{2-10}$ alkenylene-Q substituted with 0–3 $R^{b1}$, $C_{2-10}$ alkynylene-Q substituted with 0–3 $R^{b1}$, (CR$^a$R$^{a1}$)$_{r1}$O(CR$^a$R$^{a1}$)$_r$-Q, (CR$^a$R$^{a1}$)$_{r1}$NR$^a$(CR$^a$R$^{a1}$)$_r$-Q, (CR$^a$R$^{a1}$)$_{r1}$C(O)(CR$^a$R$^{a1}$)$_r$-Q, (CR$^a$R$^{a1}$)$_{r1}$C(O)O (CR$^a$R$^{a1}$)$_r$-Q, (CR$^a$R$^{a1}$)$_{r1}$OC(O)(CR$^a$R$^{a1}$)$_r$-Q, (CR$^a$R$^{a1}$)$_{r1}$C(O)NR$^a$R$^{a1}$, (CR$^a$R$^a$)$_{r1}$C(O)NR$^a$ (CR$^a$R$^{a1}$)$_r$-Q, (CR$^a$R$^{a1}$)$_{r1}$NR$^a$C(O)(CR$^a$R$^{a1}$)$_r$-Q, (CR$^a$R$^{a1}$)$_{r1}$OC(Q)O(CR$^a$R$^{a1}$)$_r$-Q, (CR$^a$R$^{a1}$)$_{r1}$C(O) NR$^a$(CR$^a$R$^{a1}$)$_r$-Q, (CR$^a$R$^{a1}$)$_{r1}$NR$^a$C(O)O(CR$^a$R$^{a1}$)$_r$-Q, (CR$^a$R$^{a1}$)$_{r1}$NR$^a$C(O)NR$^a$(CR$^a$R$^{a1}$)$_r$-Q, (CR$^a$R$^{a1}$)$_{r1}$S (O)$_p$(CR$^a$R$^{a1}$)$_r$-Q, (CR$^a$R$^{a1}$)$_{r1}$SO$_2$NR$^a$(CR$^a$R$^{a1}$)$_r$-Q, (CR$^a$R$^{a1}$)$_{r1}$NR$^a$SO$_2$(CR$^a$R$^{a1}$)$_r$-Q, and (CR$^a$R$^{a1}$)$_{r1}$ NR$^a$SO$_2$NR$^a$(CR$^a$R$^{a1}$)$_r$-Q;

Q is selected from H, a $C_{3-13}$ carbocycle substituted with 0–5 $R^d$ and a 5–14 membered heterocycle consisting of: carbon atoms and 1–4 heteroatoms selected from the group consisting of N, O, and S and substituted with 0–5 $R^d$;

$R^3$ is selected from $Q^1$, $C_{1-6}$ alkylene-$Q^1$, $C_{2-6}$ alkenylene-$Q^1$, $C_{2-6}$ alkynylene-$Q^1$, (CR$^a$R$^{a1}$)$_{r1}$O(CH$_2$)$_r$-$Q^1$, (CR$^a$R$^{a1}$)$_{r1}$NR$^a$(CR$^a$R$^{a1}$)$_r$-$Q^1$, (CR$^a$R$^{a1}$)$_{r1}$NR$^a$C(O) (CR$^a$R$^{a1}$)$_r$-$Q^1$, (CR$^a$R$^{a1}$)$_{r1}$C(O)NR$^a$(CR$^a$R$^{a1}$)$_r$-$Q^1$, (CR$^a$R$^{a1}$)$_{r1}$C(O)(CR$^a$R$^{a1}$)$_r$-$Q^1$, (CR$^a$R$^{a1}$)$_{r1}$C(O)O (CR$^a$R$^{a1}$)$_r$-$Q^1$, (CR$^a$R$^{a1}$)$_{r1}$S(O)$_p$(CR$^a$R$^{a1}$)$_r$-$Q^1$, and (CR$^a$R$^{a1}$)$_{r1}$SO$_2$NR$^a$(CR$^a$R$^{a1}$)$_r$-$Q^1$;

$Q^1$ is selected from H, phenyl substituted with 0–3 $R^d$, naphthyl substituted with 0–3 $R^d$ and a 5–10 membered heteroaryl consisting of: carbon atoms and 1–4 heteroatoms selected from the group consisting of N, O, and S and substituted with 0–3 $R^d$;

$R^4$ is selected from $Q^2$, $C_{1-6}$ alkylene-$Q^2$, $C_{2-6}$ alkenylene-$Q^2$, $C_{2-6}$ alkynylene-$Q^2$, (CR$^a$R$^{a1}$)$_{r1}$O (CH$_2$)$_r$-$Q^2$, (CR$^a$R$^{a1}$)$_{r1}$NR$^a$(CR$^a$R$^{a1}$)$_r$-$Q^2$, (CR$^a$R$^{a1}$)$_{r1}$ NR$^a$C(O)(CR$^a$R$^{a1}$)$_r$-$Q^2$, (CR$^a$R$^{a1}$)$_{r1}$C(O)NR$^a$ (CR$^a$R$^{a1}$)$_r$-$Q^2$, (CR$^a$R$^{a1}$)$_{r1}$C(O)(CR$^a$R$^{a1}$)$_r$-$Q^2$, (CR$^a$R$^{a1}$)$_{r1}$C(O)O(CR$^a$R$^{a1}$)$_r$-$Q^2$, (CR$^a$R$^{a1}$)$_{r1}$S(O)$_p$ (CR$^a$R$^{a1}$)$_r$-$Q^2$, and (CR$^a$R$^{a1}$)$_{r1}$SO$_2$NR$^a$(CR$^a$R$^{a1}$)$_r$-$Q^2$;

$Q^2$ is selected from H, phenyl substituted with 0–3 $R^d$, naphthyl substituted with 0–3 $R^d$, and a 5–10 membered heteroaryl consisting of: carbon atoms and 1–4 heteroatoms selected from the group consisting of N, O, and S and substituted with 0–3 $R^d$;

$R^a$, at each occurrence, is independently selected from H, $C_{1-4}$ alkyl, phenyl, and benzyl;

$R^{a1}$, at each occurrence, is independently selected from H and $C_{1-4}$ alkyl;

alternatively, $R^a$ and $R^{a1}$ when attached to a nitrogen are taken together with the nitrogen to which they are attached to form a 5 or 6 membered ring consisting of carbon atoms and from 0–1 additional heteroatoms selected from the group consisting of N, O, and S;

$R^{a2}$, at each occurrence, is independently selected from $C_{1-4}$ alkyl, phenyl, and benzyl;

$R^b$, at each occurrence, is independently selected from $C_{1-6}$ alkyl, OR$^a$, Cl, F, Br, I, =O, —CN, NO$_2$, NR$^a$R$^{a1}$, C(O)R$^a$, C(O)OR$^a$, C(O)NR$^a$R$^{a1}$, NR$^a$C(O)NR$^a$R$^{a1}$, OC(O)NR$^a$R$^{a1}$, S(O)$_2$NR$^a$R$^{a1}$, NR$^a$S(O)$_2$R$^{a2}$, NR$^a$S (O)$_2$NR$^a$R$^{a1}$, OS(O)$_2$NR$^a$R$^{a1}$, NR$^a$S(O)$_2$R$^{a2}$, S(O)$_p$ R$^{a2}$, CF$_3$, and CF$_2$CF$_3$;

$R^{b1}$, at each occurrence, is independently selected from OR$^a$, Cl, F, Br, I, =O, —CN, NO$_2$, and NR$^a$R$^{a1}$;

$R^c$, at each occurrence, is independently selected from $C_{1-6}$ alkyl, OR$^a$, Cl, F, Br, I, =O, —CN, NO$_2$, NR$^a$R$^{a1}$, C(O)R$^a$, C(O)OR$^a$, C(O)NR$^a$R$^{a1}$, NR$^a$C(O)NR$^a$R$^{a1}$, OC(O)NR$^a$R$^{a1}$, S(O)$_2$NR$^a$R$^{a1}$, NR$^a$S(O)$_2$R$^{a2}$, NR$^a$S (O)$_2$NR$^a$R$^{a1}$, OS(O)$_2$NR$^a$R$^{a1}$, NR$^a$S(O)$_2$R$^{a2}$, S(O)$_p$ R$^{a2}$, CF$_3$, CF$_2$CF$_3$, $C_{3-10}$ carbocycle substituted with 0–1 $R^{b1}$, and a 5–14 membered heterocycle consisting of: carbon atoms and 1–4 heteroatoms selected from the group consisting of N, O, and S and substituted with 0–1 $R^{b1}$;

$R^d$, at each occurrence, is independently selected from $C_{1-6}$ alkyl, OR$^a$, Cl, F, Br, I, =O, —CN, NO$_2$, NR$^a$R$^{a1}$, C(O)R$^a$, C(O)OR$^a$, C(O)NR$^a$R$^{a1}$, NR$^a$C(O)NR$^a$R$^{a1}$, OC(O)NR$^a$R$^{a1}$, S(O)$_2$NR$^a$R$^{a1}$, NR$^a$S(O)$_2$R$^{a2}$, NR$^a$S (O)$_2$NR$^a$R$^{a1}$, OS(O)$_2$NR$^a$R$^{a1}$, NR$^a$S(O)$_2$R$^{a2}$, S(O)$_p$ R$^{a2}$, CF$_3$, CF$_2$CF$_3$, $C_{3-10}$ carbocycle and a 5–14 membered heterocycle consisting of: carbon atoms and 1–4 heteroatoms selected from the group consisting of N, O, and S;

$R^5$, at each occurrence, is selected from $C_{1-10}$ alkyl substituted with 0–2 $R^b$, and $C_{1-8}$ alkyl substituted with 0–2 $R^e$;

$R^e$, at each occurrence, is selected from phenyl substituted with 0–2 $R^b$ and biphenyl substituted with 0–2 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$–$C_5$ alkyl)-1,3-dioxa-cyclopenten-2-one-yl]methyl, [5-($R^a$)-1,3-dioxa-cyclopenten-2-one-yl]methyl, (5-aryl-1,3-dioxa-cyclopenten-2-one-yl)methyl, —$C_{1-10}$ alkyl-$NR^7R^{7a}$, —$CH(R^8)OC(=O)R^9$, and —$CH(R^8)OC(=O)OR^9$;

$R^7$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-8}$ alkyl substituted with 1–2 $R^f$, $C_{3-8}$ cycloalkyl substituted with 1–2 $R^f$, and phenyl substituted with 0–2 $R^b$;

$R^f$, at each occurrence, is selected from $C_{1-4}$ alkyl, $C_{3-8}$ cycloalkyl, $C_{1-5}$ alkoxy, and phenyl substituted with 0–2 $R^b$;

p, at each occurrence, is selected from 0, 1, and 2;

q, at each occurrence, is selected from 0, 1, and 2;

$R^3$ is selected from $Q^1$, $C_{1-6}$ alkylene-$Q^1$, $C_{2-6}$ alkenylene-$Q^1$, $C_{2-6}$ alkynylene-$Q^1$, $(CR^aR^{a1})_{r1}O(CH_2)_r$-$Q^1$, $(CR^aR^{a1})_{r1}NR^a(CR^aR^{a1})_r$-$Q^1$, $(CR^aR^{a1})_{r1}NR^aC(O)(CR^aR^{a1})_r$-$Q^1$, $(CR^aR^{a1})_{r1}C(O)NR^a(CR^aR^{a1})_r$-$Q^1$, $(CR^aR^{a1})_{r1}C(O)(CR^aR^{a1})_r$-$Q^1$, $(CR^aR^{a1})_{r1}C(O)O(CR^aR^{a1})_r$-$Q^1$, $(CR^aR^{a1})_{r1}S(O)_p(CR^aR^{a1})_r$-$Q^1$, and $(CR^aR^{a1})_{r1}SO_2NR^a(CR^aR^{a1})_r$-$Q^1$;

Q is selected from H, a $C_{3-6}$ carbocycle substituted with 0–5 $R^d$, and a 5–10 membered heterocycle consisting of: carbon atoms and 1–4 heteroatoms selected from the group consisting of N, O, and S and substituted with 0–5 $R^d$;

$Q^1$ is selected from H, phenyl substituted with 0–3 $R^d$, and a 5–6 membered heteroaryl consisting of: carbon atoms and 1–4 heteroatoms selected from the group consisting of N, O, and S and substituted with 0–3 $R^d$;

$R^4$ is selected from $Q^2$, $C_{1-6}$ alkylene-$Q^2$, $C_{2-6}$ alkenylene-$Q^2$, $(CR^aR^{a1})_{r1}O(CH_2)_r$-$Q^2$, $(CR^aR^{a1})_{r1}NR^a(CR^aR^{a1})_r$-$Q^2$, $(CR^aR^{a1})_{r1}NR^aC(O)(CR^aR^{a1})_r$-$Q^2$, $(CR^aR^{a1})_{r1}C(O)NR^a(CR^aR^{a1})_r$-$Q^2$, $(CR^aR^{a1})_{r1}C(O)(CR^aR^{a1})_r$-$Q^2$, $(CR^aR^{a1})_{r1}S(O)_p(CR^aR^{a1})_r$-$Q^2$, and $(CR^aR^{a1})_{r1}SO_2NR^a(CR^aR^{a1})_r$-$Q^2$;

$Q^2$ is selected from H, phenyl substituted with 0–3 $R^d$, and a 5–6 membered heteroaryl consisting of: carbon atoms and 1–4 heteroatoms selected from the group consisting of N, O, and S and substituted with 0–3 $R^d$;

$R^a$, at each occurrence, is independently selected from H, $C_{1-4}$ alkyl, phenyl, and benzyl;

$R^{a1}$, at each occurrence, is independently selected from H and $C_{1-4}$ alkyl;

alternatively, $R^a$ and $R^{a1}$ when attached to a nitrogen are taken together with the nitrogen to which they are attached to form a 5 or 6 membered ring consisting of: carbon atoms and from 0–1 additional heteroatoms selected from the group consisting of N, O, and S;

$R^{a2}$, at each occurrence, is independently selected from $C_{1-4}$ alkyl, phenyl, and benzyl;

$R^b$, at each occurrence, is independently selected from $C_{1-6}$ alkyl, $OR^a$, Cl, F, Br, =O, —CN, $NR^aR^{a1}$, $C(O)R^a$, $C(O)OR^a$, $C(O)NR^aR^{a1}$, $S(O)_2NR^aR^{a1}$, $S(O)_pR^{a2}$, and $CF_3$;

$R^c$, at each occurrence, is independently selected from $C_{1-6}$ alkyl, $OR^a$, Cl, F, Br, =O, —CN, $NO_2$, $NR^aR^{a1}$, $C(O)R^a$, $C(O)OR^a$, $C(O)NR^aR^{a1}$, $S(O)_2NR^aR^{a1}$, $S(O)_pR^{a2}$, $CF_3$, $C_{3-6}$ carbocycle, and a 5–6 membered heterocycle consisting of: carbon atoms and 1–4 heteroatoms selected from the group consisting of N, O, and S;

$R^d$, at each occurrence, is independently selected from $C_{1-6}$ alkyl, $OR^a$, Cl, F, Br, =O, —CN, $NR^aR^{a1}$, $C(O)R^a$, $C(O)OR^a$, $C(O)NR^aR^{a1}$, $S(O)_2NR^aR^{a1}$, $S(O)_pR^{a2}$, $CF_3$, $C_{3-6}$ carbocycle, and a 5–6 membered heterocycle consisting of: carbon atoms and 1–4 heteroatoms selected from the group consisting of N, O, and S;

$R^5$, at each occurrence, is selected from $C_{1-6}$ alkyl substituted with 0–2 $R^b$, and $C_{1-4}$ alkyl substituted with 0–2 $R^e$;

$R^e$, at each occurrence, is selected from phenyl substituted with 0–2 $R^b$, and biphenyl substituted with 0–2 $R^b$;

$R^6$, at each occurrence, is selected from phenyl, naphthyl, $C_{1-10}$ alkyl-phenyl-$C_{1-6}$ alkyl-, $C_{1-3}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-C1-3 alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$–$C_5$ alkyl)-1,3-dioxa-cyclopenten-2-one-yl]methyl, [5-($R^a$)-1,3dioxa-cyclopenten-2-one-yl]methyl, (5-aryl-1,3-dioxa-cyclopenten-2-one-yl)methyl, —$C_{1-10}$ alkyl-$NR^7R^{7a}$, —$CH(R^8)OC(=O)R^9$, and —$CH(R^8)OC(=O)OR^9$;

$R^7$ is selected from H and $C_{1-6}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-6}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-6}$ alkyl substituted with 1–2 $R^f$, $C_{3-6}$ cycloalkyl substituted with 1–2 $R^f$, and phenyl substituted with 0–2 $R^b$;

$R^f$, at each occurrence, is selected from $C_{1-4}$ alkyl, $C_{3-6}$ cycloalkyl, $C_{1-5}$ alkoxy, and phenyl substituted with 0–2 $R^b$;

p, at each occurrence, is selected from 0, 1, and 2;

r, at each occurrence, is selected from 0, 1, 2, 3, and 4; and, r, at each occurrence, is selected from 0, 1, 2, 3, and 4; and, r1, at each occurrence, is selected from 0, 1, 2, 3, and 4.

2. A compound according to claim 1, wherein the compound is of formula IIb:

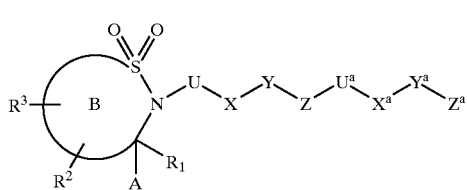

IIb or a stereoisomer or pharmaceutically acceptable salt form thereof, wherein;

ring B, including the $SO_2$ and N, is a 5–6 membered non-aromatic heterocycle consisting of: $SO_2$, N, and carbon atoms;

U is absent or is selected from: O, $NR^{a1}$, C(O), C(O)O, OC(O), C(O)$NR^{a1}$, and $NR^{a1}$C(O);

X is absent or is selected from $C_{1-4}$ alkylene, $C_{2-4}$ alkenylene, and $C_{2-4}$ alkynylene;

Y is absent or is selected from: O, $NR^{a1}$, C(O), C(O)O, OC(O), C(O)$NR^{a1}$, and $NR^{a1}$C(O);

Z is absent or selected from a $C_{3-6}$ carbocycle substituted with 0–4 Rb and a 5–6 membered heterocycle consisting of: carbon atoms and 1–4 heteroatoms selected from the group consisting of N, O, and S and substituted with 0–3 $R^b$;

$U^a$ is absent or is selected from: O, $NR^{a1}$, C(O), C(O)O, C(O)$NR^{a1}$, $NR^{a1}$C(O), S(O)$_p$, and S(O)$_p$$NR^{a1}$;

$X^a$ is absent or is $C_{1-4}$ alkylene;

$Y^a$ is absent or selected from O and $NR^{a1}$;

$Z^a$ is selected from a $C_{3-10}$ carbocycle substituted with 0–5 $R^c$ and a 5–10 membered heterocycle consisting of: carbon atoms and 1–4 heteroatoms selected from the group consisting of N, O, and S and substituted with 0–5 $R^c$;

provided that when U-X—Y are $CH_2$, $U^a$-$X^a$—$Y^a$ are absent, and Z is phenyl, then $Z^a$ is other than a 2-substituted phenyl ring or a 3,5-disubstituted phenyl ring;

provided that U, X, Y, Z, $U^a$, $X^a$, $Y^a$, $Z^a$, combine to form other than a N—N, N—O, O—N, O—O, S(O)$_p$—O, O—S(O)$_p$ or S(O)$_p$—S(O)$_p$ group, an unsubstituted naphthyl, a substituted naphthyl wherein the substituent is 1–3 atoms in length, an unsubstituted phenyl, a substituted phenyl wherein the substituent is 1–3 atoms in length, an unsubstituted benzyl, or a substituted benzyl wherein the substituent is 1–3 atoms in length;

$R^1$ is selected from H, $C_{1-4}$ alkyl, phenyl, and benzyl;

$R^2$ is selected from Q, $C_{1-6}$ alkylene-Q, $C_{2-6}$ alkenylene-Q, $C_{2-6}$ alkynylene-Q, $(CR^aR^{a1})_{r1}O(CR^aR^{a1})_r$-Q, $(CR^aR^{a1})_{r1}NR^a(CR^aR^{a1})_r$-Q, $(CR^aR^{a1})_{r1}C(O)(CR^aR^{a1})_r$-Q, $(CR^aR^{a1})_{r1}C(O)O(CR^aR^{a1})_r$-Q, $(CR^aR^{a1})_{r1}C(O)NR^aR^{a1}$, $(CR^aR^{a1})_{r1}C(O)NR^a(CR^aR^{a1})_r$-Q, $(CR^aR^{a1})_{r1}S(O)_p(CR^aR^{a1})_r$-Q, and $(CR^aR^{a1})_{r1}SO_2NR^a(CR^aR^{a1})_r$-Q;

r1, at each occurrence, is selected from 0, 1, 2, 3, and 4.

3. A compound according to claim 2, wherein the compound is of formula IIIc–d:

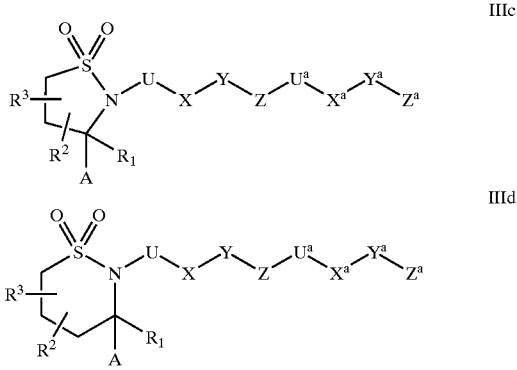

IIIc

IIId or a stereoisomer or pharmaceutically acceptable salt form thereof, wherein;

A is selected from —CONHOR$^5$ and —N(OH)COR$^5$;

U is absent or is selected from: O, $NR^{a1}$, and C(O);

X is absent or is $C_{1-4}$ alkylene;

Y is absent or is selected from: O and $NR^{a1}$;

Z is absent or selected from a $C_{5-6}$ carbocycle substituted with 0–3 Rb and a 5–6 membered heteroaryl consisting of: carbon atoms and from 1–4 heteroatoms selected from the group consisting of N, O, and S and substituted with 0–3 $R^b$;

$U^a$ is absent or is selected from: O, $NR^{a1}$, C(O), C(O)$NR^{a1}$, S(O)$_p$, and S(O)$_p$$NR^{a1}$;

$X^a$ is absent or is $C_{1-2}$ alkylene;

$Y^a$ is absent or selected from O and $NR^{a1}$;

$Z^a$ is selected from a $C_{5-6}$ carbocycle substituted with 0–3 $R^c$ and a 5–10 membered heteroaryl consisting of carbon atoms and from 1–4 heteroatoms selected from the group consisting of N, O, and S and substituted with 0–3 $R^c$;

provided that when U-X—Y are $CH_2$, $U^a$-$X^a$—$Y^a$ are absent, and Z is phenyl, then $Z^a$ is other than a 2-substituted phenyl ring or a 3,5-disubstituted phenyl ring;

provided that U, X, Y, Z, $U^a$, $X^a$, $Y^a$, $Z^a$, combine to form other than a N—N, N—O, O—N, O—O, S(O)$_p$—O, O—S(O)$_p$ or S(O)$_p$—S(O)$_p$ group, an unsubstituted naphthyl, a substituted naphthyl wherein the substituent is 1–3 atoms in length, an unsubstituted phenyl, a substituted phenyl wherein the substituent is 1–3 atoms in length, an unsubstituted benzyl, or a substituted benzyl wherein the substituent is 1–3 atoms in length;

$R^1$ is selected from H, $C_{1-4}$ alkyl, phenyl, and benzyl;

$R^2$ is selected from Q, $C_{1-6}$ alkylene-Q, $C_{2-6}$ alkenylene-Q, $C_{2-6}$ alkynylene-Q, $(CR^aR^{a1})_{r1}O(CR^aR^{a1})_r$-Q, $(CR^aR^{a1})_{r1}NR^aCR^aR^{a1})_r$-Q, $(CR^aR^{a1})_{r1}C(O)(CR^aR^{a1})_r$-Q, $(CR^aR^{a1})_{r1}C(O)O(CR^aR^{a1})_r$-Q, $(CR^aR^{a2})_{r1}C(O)NR^aR^{a1}$, $(CR^aR^{a2})_{r1}C(O)NR^a(CR^aR^{a1})_r$-Q and $(CR^aR^{a1})_{r1}S(O)_p(CR^aR^{a1})_r$-Q;

Q is selected from H, a $C_{3-6}$ carbocycle substituted with 0–3 $R^d$, and a 5–10 membered heterocycle consisting of: carbon atoms and 1–4 heteroatoms selected from the group consisting of N, O, and S and substituted with 0–3 $R^d$;

$R^3$ is selected from $Q^1$, $C_{1-6}$ alkylene-$Q^1$, $(CR^aR^{a1})_{r1}O(CH_2)_r$-$Q^1$, $(CR^aR^{a1})_{r1}NR^a(CR^aR^{a1})_r$-$Q^1$, $(CR^aR^{a1})_{r1}$ C(O)NR$^a$(CR$^a$R$^{a1}$)$_r$-Q$^1$, (CR$^a$R$^{a1}$)$_{r1}$C(O)(CR$^a$R$^{a1}$)$_r$-Q$^1$, and (CR$^a$R$^{a1}$)$_{r1}$SO$_2$NR$^a$(CR$^a$R$^{a1}$)$_r$-Q$^1$;

Q$^1$ is selected from H, phenyl substituted with 0–2 R$^d$, and a 5–6 membered heteroaryl consisting of: carbon atoms and 1–3 heteroatoms selected from the group consisting of N, O, and S and substituted with 0–2 R$^d$;

R$^4$ is selected from Q$^2$, C$_{1-6}$ alkylene-Q$^2$, (CR$^a$R$^{a1}$)$_{r1}$O(CH$_2$)$_r$-Q$^2$, (CR$^a$R$^{a1}$)$_{r1}$NR$^a$(CR$^a$R$^{a1}$)$_r$-Q$^2$, (CR$^a$R$^{a1}$)$_{r1}$C(O)NR$^a$(CR$^a$R$^{a1}$)$_r$-Q$^2$, (CR$^a$R$^{a1}$)$_{r1}$C(O)(CR$^a$R$^{a1}$)$_r$-Q$^2$, and (CR$^a$R$^{a1}$)$_{r1}$SO$_2$NR$^a$(CR$^a$R$^{a1}$)$_r$-Q$^2$;

Q$^2$ is selected from H, phenyl substituted with 0–2 R$^d$, and a 5–6 membered heteroaryl consisting of: carbon atoms and 1–3 heteroatoms selected from the group consisting of N, O, and S and substituted with 0–2 R$^d$;

R$^a$, at each occurrence, is independently selected from H, C$_{1-4}$ alkyl, phenyl, and benzyl;

R$^{a1}$, at each occurrence, is independently selected from H and C$_{1-4}$ alkyl;

R$^{a2}$, at each occurrence, is independently selected from C$_{1-4}$ alkyl, phenyl, and benzyl;

R$^b$, at each occurrence, is independently selected from C$_{1-4}$ alkyl, OR$^a$, Cl, F, =O, NR$^a$R$^{a1}$, C(O)R$^a$, C(O)OR$^a$, C(O)NR$^a$R$^{a1}$, S(O)$_2$NR$^a$R$^{a1}$, S(O)$_p$R$^{a2}$, and CF$_3$;

R$^c$, at each occurrence, is independently selected from C$_{1-6}$ alkyl, OR$^a$, Cl, F, Br, =O, NO$_2$, NR$^a$R$^{a1}$, C(O)R$^a$, C(O)NR$^a$R$^{a1}$, S(O)$_2$NR$^a$R$^{a1}$, S(O)$_p$R$^{a2}$, and CF$_3$;

R$^d$, at each occurrence, is independently selected from C$_{1-6}$ alkyl, OR$^a$, Cl, F, Br, =O, NR$^a$R$^{a1}$, C(O)R$^a$, C(O)NR$^a$R$^{a1}$, S(O)$_2$NR$^a$R$^{a1}$, S(O)$_p$R$^{a2}$, CF$_3$, and phenyl;

R$^5$, at each occurrence, is selected from C$_{1-4}$ alkyl substituted with 0–2 Rb and C$_{1-4}$ alkyl substituted with 0–2 R$^e$;

R$^e$, at each occurrence, is selected from phenyl substituted with 0–2 R$^b$ and biphenyl substituted with 0–2 R$^b$;

p, at each occurrence, is selected from 0, 1, and 2;

r, at each occurrence, is selected from 0, 1, 2, 3, and 4; and, r1, at each occurrence, is selected from 0, 1, 2, 3, and 4.

4. A compound according to claim 3, wherein:

U is absent;

X is absent or is selected from CH$_2$ and CH$_2$CH$_2$;

Y is absent;

Z is absent or selected from phenyl substituted with 0–3 R$^b$ and pyridyl substituted with 0–3 R$^b$;

U$^a$ is absent or is O;

X$^a$ is absent or is CH$_2$ or CH$_2$CH$_2$;

Y$^a$ is absent or is O;

Z$^a$ is selected from phenyl substituted with 0–3 R$^c$, pyridyl substituted with 0–3 R$^c$, thienyl substituted with 0–3 R$^c$, furanyl substituted with 0–3 R$^c$, and quinolinyl substituted with 0–3 R$^c$;

provided that when U-X—Y are CH$_2$, U$^a$-X$^a$—Y$^a$ are absent, and Z is phenyl, then Z$^a$ is other than a 2-substituted phenyl ring or a 3,5-disubstituted phenyl ring;

provided that U, X, Y, Z, U$^a$, X$^a$, Y$^a$, Z$^a$, combine to form other than a N—N, N—O, O—N, O—O, S(O)$_p$—O, O—S(O)$_p$ or S(O)$_p$—S(O)$_p$ group, an unsubstituted naphthyl, a substituted naphthyl wherein the substituent is 1–3 atoms in length, an unsubstituted phenyl, a substituted phenyl wherein the substituent is 1–3 atoms in length, an unsubstituted benzyl, or a substituted benzyl wherein the substituent is 1–3 atoms in length;

R$^1$ is selected from H, CH$_3$, and CH$_2$CH$_3$;

R$^2$ is selected from Q, C$_{1-6}$ alkylene-Q, (CR$^a$R$^{a1}$)$_{r1}$(CR$^a$R$^{a1}$)$_r$-Q, (CR$^a$R$^{a1}$)$_{r1}$NR$^a$(CR$^a$R$^{a1}$)$_p$-Q, C(O)(CR$^a$R$^{a1}$)$_r$-Q, C(O)O(CR$^a$R$^{a1}$)$_r$-Q, C(O)NR$^a$(CR$^a$-R$^{a1}$)$_r$-Q, and S(O)$_p$(CR$^a$R$^{a1}$)$_r$-Q;

Q is selected from H, cyclopropyl substituted with 0–1 R$^d$, cyclobutyl substituted with 0–1 R$^d$, cyclopentyl substituted with 0–1 R$^d$, cyclohexyl substituted with 0–1 R$^d$, phenyl substituted with 0–2 R$^d$, and a heterocycle substituted with 0–3 R$^d$, wherein the heterocycle is selected from pyridyl, quinolinyl, thiazolyl, furanyl, imidazolyl, and isoxazolyl;

R$^3$ is selected from Q$^1$, C$_{1-4}$ alkylene-Q$^1$, (CH$_2$)$_{r1}$O-(CH$_2$)$_r$-Q$^1$, (CH$_2$)$_{r1}$NR$^a$(CH$_2$)$_r$-Q$^1$, (CH$_2$)$_{r1}$C(O)NR$^a$(CH$_2$)$_r$-Q$^1$, (CH$_2$)$_{r1}$C(O)(CH$_2$)$_r$-Q$^1$, and (CH$_2$)$_{r1}$SO$_2$NR$^a$(CH$_2$)$_r$-Q$^1$;

Q$^1$ is selected from H, phenyl substituted with 0–2 R$^d$, and a heteroaryl substituted with 0–2 R$^d$, wherein the heteroaryl is selected from pyridyl, thiazolyl, furanyl, imidazolyl, and isoxazolyl;

R$^4$ is selected from H and C$_{1-4}$ alkyl;

R$^a$, at each occurrence, is independently selected from H, CH$_3$, and CH$_2$CH$_3$;

R$^{a1}$, at each occurrence, is independently selected from H, CH$_3$, and CH$_2$CH$_3$;

R$^{a2}$, at each occurrence, is independently selected from H, CH$_3$, and CH$_2$CH$_3$;

R$^b$, at each occurrence, is independently selected from C$_{1-4}$ alkyl, OR$^a$, Cl, F, =O, NR$^a$R$^{a1}$, C(O)R$^a$, C(O)OR$^a$, C(O)NR$^a$R$^{a1}$, S(O)$_2$NR$^a$R$^{a1}$, S(O)$_p$R$^{a2}$, and CF$_3$;

R$^c$, at each occurrence, is independently selected from C$_{1-6}$ alkyl, OR$^a$, Cl, F, Br, =O, NO$_2$, NR$^a$R$^{a1}$, C(O)R$^a$, C(O)NR$^a$R$^{a1}$, S(O)$_2$NR$^a$R$^{a1}$, S(O)$_p$R$^{a2}$, and CF$_3$;

R$^d$, at each occurrence, is independently selected from C$_{1-6}$ alkyl, OR$^a$, Cl, F, Br, =O, NR$^a$R$^{a1}$, C(O)R$^a$, C(O)NR$^a$R$^{a1}$, S(O)$_2$NR$^a$R$^{a1}$, S(O)$_p$R$^{a2}$, CF$_3$, and phenyl;

p, at each occurrence, is selected from 0, 1, and 2;

r, at each occurrence, is selected from 0, 1, 2, and 3; and, r1, at each occurrence, is selected from 0, 1, 2, and 3.

5. A compound according to claim 4, wherein the compound is of formula IVc–d:

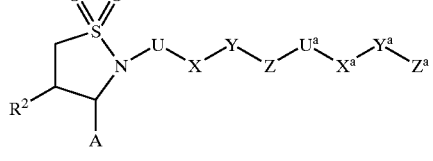

IVc

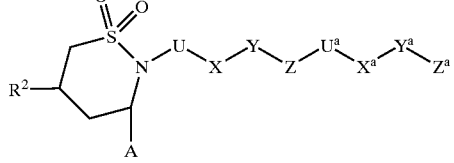

IVd

U is absent;

X is absent or is selected from CH$_2$ and CH$_2$CH$_2$;

Y is absent;

Z is phenyl;

U$^a$ is absent or is O;

X$^a$ is absent or is CH$_2$;

Y$^a$ is absent;

Z$^a$ is selected from phenyl substituted with 0–2 R$^c$, pyridyl substituted with 0–1 R$^c$, and quinolinyl substituted with 0–2 R$^c$;

provided that when U-X—Y are CH$_2$ and U$^a$-X$^a$—Y$^a$ are absent, then Z$^a$ is other than a 2-substituted phenyl ring or a 3,5-disubstituted phenyl ring;

R$^2$ is selected from O-Q, CH$_2$O-Q, O(CR$^a$R$^{a1}$)-Q, CH$_2$O(CR$^a$R$^{a1}$)-Q, O(CR$^a$R$^{a1}$)(CR$^a$R$^{a1}$)-Q, CH$_2$O(CR$^a$R$^{a1}$)(CR$^a$R$^{a1}$)-Q, NR$^a$Q, CH$_2$NR$^a$-Q, NR$^a$(CR$^a$R$^{a1}$)-Q, CH$_2$NR$^a$(CR$^a$R$^{a1}$)-Q, NR$^a$(CR$^a$R$^{a1}$)(CR$^a$R$^{a1}$)-Q, and CH$_2$NR$^a$(CR$^a$R$^{a1}$)(CR$^a$R$^{a1}$)-Q;

Q is selected from H, cyclopropyl substituted with 0–1 R$^d$, cyclobutyl substituted with 0–1 R$^d$, cyclopentyl substituted with 0–1 R$^d$, cyclohexyl substituted with 0–1 R$^d$, phenyl substituted with 0–2 R$^d$, and a heterocycle substituted with 0–3 R$^d$, wherein the heterocycle is selected from pyridyl, quinolinyl, thiazolyl, furanyl, imidazolyl, and isoxazolyl;

R$^a$ is independently selected from H, CH$_3$, and CH$_2$CH$_3$;

R$^c$, at each occurrence, is independently selected from CH$_3$, C(CH$_3$)$_3$, OCH$_3$, Cl, F, NO$_2$, NH$_2$, C(O)H, SCH$_3$, S(O)$_2$CH$_3$, and CF$_3$;

R$^d$, at each occurrence, is independently selected from C$_{1-6}$ alkyl, OR$^a$, Cl, F, Br, =O, NR$^a$R$^{a1}$, C(O)R$^a$, C(O)NR$^a$R$^{a1}$, S(O)$_2$NR$^a$R$^{a1}$, S(O)$_p$R$^{a2}$, CF$_3$, and phenyl; and, p, at each occurrence, is selected from 0, 1, and 2;

r, at each occurrence, is selected from 0, 1, and 2; and, r1, at each occurrence, is selected from 0, 1, and 2.

6. A compound according to claim 1, wherein the compound is selected from the group:

(R/S) 2-([1,1'-biphenyl]-4-ylmethyl)-N-hydroxy-3-isothiazolidinecarbooxamide 1,1-dioxide;

(R/S) 2-(2-[1,1'-biphenyl]-4-ylmethyl)-N-hydroxy-3-isothiazolidinecarboxamide 1,1-dioxide;

(R/S) N-Hydroxy-2-(2-phenylethyl)-3-isothiazolidinecarboxamide 1,1-dioxide;

(R/S) 2-[1,1'-biphenyl]-4-yl-N-hydroxy-3-isothiazolidinecarboxamide 1,1-dioxide;

(R/S) N-Hydroxy-2-((4'-methoxy-1,1'-biphenyl]-4-yl)methyl)3-isothiazolidinecarboxamide 1,1-dioxide;

(R/S) N-Hydroxy-2-[4-(3-thienyl)benzyl]-3-isothiazolidinecarboxamide 1,1-dioxide;

(R/S) 2-[4-(2-furyl)benlzyl]-N-Hydroxy-3-isothiazolidinecarboxamide 1,1-dioxide;

(R/S) N-Hydroxy-2-(4-phenoxybenzyl)-3-isothiazolidinecarboxamide 1,1-dioxide;

(R/S) N-Hydroxy-2-[4-(4-methoxyphenoxy)benzyl]-3isothiazolidinecarboxamide 1,1-dioxide;

(R/S) N-Hydroxy-2-{4-[4-(trifluoromethyl)phenoxy]benzyl}-3-isothiazolidinecarboxamide 1,1-dioxide;

(R/S) N-Hydroxy-2-[4-(4-pyridinylmethoxy)benzyl]-3-isothiazolidinecarboxamide 1,1-dioxide;

(3R) 2-([1,1'-biphenyl]-ylmethyl)-N-hydroxy-3-isothiazolidinecarboxamide 1,1-dioxide;

(3R) 2-([1,1'-biphenyl]-4-ylmethyl)tetrahydro-N-hydroxy-2H-1,2-thiazine-3-carboxamide 1,1-dioxide;

(3R)-N-hydroxy-2-((3',4'-dimethoxy[1,1'-biphenyl]-4-yl)methyl)tetrahydro-2H-1,2-thiazine-3-carboxamide 1,1-dioxide;

(3R)-N-hydroxy-2-((4'-methoxy[1,1'-biphenyl]-4-yl)methyl)tetrahydro-2H-1,2-thiazine-3-carboxamide 1,1-dioxide;

(3R)-N-hydroxy-2-((4'-trifluoromethyl[1,1'-biphenyl]-4-yl)methyl)tetrahydro-2H-1,2-thiazine-3-carboxamide 1,1-dioxide;

(3R)-N-hydroxy-2-((4'-tert-butyl[1,1'-biphenyl]-4-yl)methyl)tetrahydro-2H-1,2-thiazine-3-carboxamide 1,1-dioxide;

(3R)-N-hydroxy-2-((4'-chloro[1,1'-biphenyl]-4-yl)methyl)tetrahydro-2H-1,2-thiazine-3-carboxamide 1,1-dioxide;

(3R)-N-hydroxy-2-((4'-methylthio[1,1'-biphenyl]-4-yl)methyl)tetrahydro-2H-1,2-thiazine-3-carboxamide 1,1-dioxide;

(3R)-N-hydroxy-2-((4'-methylsulfonyl[1,1'-biphenyl]-4-yl)methyl)tetrahydro-2H-1,2-thiazine-3-carboxamide 1,1-dioxide;

(3R)-N-hydroxy-2-((3',4'-dichloro[1,1'-biphenyl]-4-yl)methyl)tetrahydro-2H-1,2-thiazine-3-carboxamide 1,1-dioxide;

(3R)-N-hydroxy-2-((4'-methoxycarbonyl[1,1'-biphenyl]-4-yl)methyl)tetrahydro-2H-1,2-thiazine-3-carboxamide 1,1-dioxide;

(3R)-N-hydroxy-2-((3',4'-methylenedioxy[1,1'-biphenyl]-4-yl)methyl)tetrahydro-2H-1,2-thiazine-3-Carboxamide 1,1-dioxide;

(3R)-N-hydroxy-2-((4'-nitro[1,1'-biphenyl]-4-yl)methyl)tetrahydro-2H-1,2-thiazine-3-carboxamide 1,1-dioxide;

(3R)-N-hydroxy-2-((4'-amino[1,1'-biphenyl]-4-yl)methyl)tetrahydro-2H-1,2-thiazine-3-carboxamide 1,1-dioxide;

(3R)-N-hydroxy-2-((4-(5-chloro-2-thienyl)benzyl)tetrahydro-2H-1,2-thiazine-3-carboxamide 1,1-dioxide;

(3R)-N-hydroxy-2-(4-(3'-fluorobiphenyl)benzyl)tetrahydro-2H-1,2-thiazine-3-carboxamide 1,1-dioxide;

(3R)-N-hydroxy-2-(4-(2-benzo[b]thiophene)benzyl)tetrahydro-2H-1,2-thiazine-3-carboxamide 1,1-dioxide;

(3R)-N-hydroxy-2-(4-(3-formyl-2-thiophene)benzyl)tetrahydro-2H-1,2-thiazine-3-carboxamide 1,1-dioxide;

(3R)-N-hydroxy-2-(4-(3-pyridinyl)benzyl)tetrahydro-2H-1,2-thiazine-3-carboxamide 1,1-dioxide;

(3R)-N-hydroxy-2-(4-(4-pyridinyl)benzyl)tetrahydro-2H-1,2-thiazine-3-carboxamide 1,1-dioxide;

(3R)-N-hydroxy-2-(4-(2-pyridinyl)benzyl)tetrahydro-2H-1,2-thiazine-3-carboxamide 1,1-dioxide;

(3R)-N-hydroxy-2-(4-(4-methoxy-3-pyridinyl)benzyl)tetrahydro-2H-1,2-thiazine-3-carboxamide 1,1-dioxide;

(3R)-N-hydroxy-2-{4-[(6-methoxy-3-pyridinyl)oxy]benzyl}tetrahydro-2H-1,2-thiazine-3-carboxamide 1,1-dioxide;

N-hydroxy-2-{4-[(2-methyl-4-quilonilyl)methoxy]benzyl}-3-isothiazolidinecarboxamide 1,1-dioxide;

N-hydroxy-2-{4-[(2-methyl4-quinolinyl)methoxy]phenyl}-3-isothiazolidinecarboxamide 1,1 dioxide;

N-hydroxy-2-(2-{4-[(2-methy-4quinolinyl)methoxy]phenyl}ethyl)-3-isothiazolidinecarboxamide 1,1-dioxide;

N-hydroxy-2-{4-[(2-methyl-4-quinolinyl)methoxy]benzyl}tetrahydro-2H-1,2-thiazine-3-carboxamide 1,1-dioxide; and N-hydroxy-2-{4[(2-methyl-4-quinolinyl)methoxy]phenyl}tetrahydro-2H-1,2thiazine-3-carboxamide 1,1-dioxide;

or a pharmaceutically acceptable salt form thereof.

7. A pharmaceutical composition, comprising: a pharmaceutically acceptable carrier and a therapeutically effective amount of a compound according to claim 1 or a pharmaceutically acceptable salt form thereof.

8. A method for treating an inflammatory disorder, comprising: administering to a patient in need thereof a therapeutically effective amount of a compound according to claim 1 or a pharmaceutically acceptable salt form thereof.

9. A method of treating a disorder, comprising: administering to a patient in need thereof a therapeutically effective amount of a compound according to claim 1 or a pharmaceutically acceptable salt form thereof, wherein the disorder is referred to as acute infection, acute phase response, age related macular degeneration, alcoholism, allergy, allergic asthma, aneurism, anorexia, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderrna, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

10. A pharmaceutical composition, comprising: a pharmaceutically acceptable carrier and a therapeutically effective amount of a compound according to claim 2 or a pharmaceutically acceptable salt form thereof.

11. A method for treating an inflammatory disorder, comprising: administering to a patient in need thereof a therapeutically effective amount of a compound according to claim 2 or a pharmaceutically acceptable salt form thereof.

12. A method of treating a disorder, comprising: administering to a patient in need thereof a therapeutically effective amount of a compound according to claim 2 or a pharmaceutically accentable salt form thereof, wherein the disorder is referred to as acute infection, acute phase response, age related macular degeneration, alcoholism, allergy, allergic asthma, aneurism, anorexia, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent bydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

13. A pharmaceutical composition, comprising: a pharmaceutically acceptable carrier and a therapeutically effective amount of a compound according to claim 3 or a pharmaceutically acceptable salt form thereof.

14. A method for treating an inflammatory disorder, comprising: administering to a patient in need thereof a therapeutically effective amount of a compound according to claim 3 or a pharmaceutically acceptable salt form thereof.

15. A method of treating a disorder, comprising: administering to a patient in need thereof a therapeutically effective amount of a compound according to claim 3 or a pharmaceutically acceptable salt form thereof, wherein the disorder is referred to as acute infection, acute phase response, age related macular degeneration, alcoholism, allergy, allergic asthma, aneurism, anorexia, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

16. A pharmaceutical composition, comprising: a pharmaceutically acceptable carrier and a therapeutically effective amount of a compound according to claim 4 or a pharmaceutically acceptable salt form thereof.

17. A method for treating an inflammatory disorder, comprising: administering to a patient in need thereof a therapeutically effective amount of a compound according to claim 4 or a pharmaceutically acceptable salt form thereof.

18. A method of treating a disorder, comprising: administering to a patient in need thereof a therapeutically effective amount of a compound according to claim 4 or a pharmaceutically acceptable salt form thereof, wherein the disorder is referred to as acute infection, acute phase response, age related macular degeneration, alcoholism, allergy, allergic asthma, aneurism, anorexia, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

19. A pharmaceutical composition, comprising: a pharmaceutically acceptable carrier and a therapeutically effective amount of a compound according to claim 5 or a pharmaceutically acceptable salt form thereof.

20. A method for treating an inflammatory disorder, comprising: administering to a patient in need thereof a therapeutically effective amount of a compound according to claim 5 or a pharmaceutically acceptable salt form thereof.

21. A method of treating a disorder, comprising: administering to a patient in need thereof a therapeutically effective amount of a compound according to claim 5 or a pharmaceutically acceptable salt form thereof, wherein the disorder is referred to as acute infection, acute phase response, age related macular degeneration, alcoholism, allergy, allergic asthma, aneurism, anorexia, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

22. A pharmaceutical composition, comprising: a pharmaceutically acceptable carrier and a therapeutically effective amount of a compound according to claim 6 or a pharmaceutically acceptable salt form thereof.

23. A method for treating an inflammatory disorder, comprising: administering to a patient in need thereof a therapeutically effective amount of a compound according to claim 6 or a pharmaceutically acceptable salt form thereof.

24. A method of treating a disorder, comprising: administering to a patient in need thereof a therapeutically effective amount of a compound according to claim 6 or a pharmaceutically acceptable salt form thereof, wherein the disorder is referred to as acute infection, acute phase response, age related macular degeneration, alcoholism, allergy, allergic asthma, aneurism, anorexia, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, sepsis, syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

\* \* \* \* \*

UNITED STATES PATENT AND TRADEMARK OFFICE
CERTIFICATE OF CORRECTION

PATENT NO. : 6,927,216 B2
DATED : August 9, 2005
INVENTOR(S) : Robert J. Cherney and Bryan W. King It is certified that error appears in the above-identified patent and that said Letters Patent is hereby corrected as shown below:

Column 80,
Line 1, delete "R3" and insert -- $R^3$ --;

Column 81,
Line 12, delete "-$C_{1\ -3}$ alkyl-," and insert -- -$C_{1-3}$ alkyl-, --;
Line 14, delete "-$C_{1-3}$  alkyl-," and insert -- -$C_{1-3}$ alkyl-, --;
Line 16, delete "[5-($C_{1-C5}$ alkyl)-1,3-" and insert -- [5-($C_1$-$C_5$ alkyl)-1,3- --;
Lines 36-67, delete "$R^3$ is …" thru "…r, at each occurrence, is selected from 0, 1, 2, 3, and 4; and," and move to column 83, after line 65;

Column 82,
Lines 1-64, delete "$R^3$ is …" thru "…r, at each occurrence, is selected from 0, 1, 2, 3, and 4; and," and move to column 83, after line 65;

Column 83,
Line 29, delete "0-4 Rb" and insert -- 0-4 $R^b$ --;

Column 85,
Line 34, delete "0-2 Rb" and insert -- 0-2 $R^b$ --;
Line 49, delete "$U^a$ is absent or is 0" and insert -- $U^a$ is absent or is O --;

Column 87,
Line 37, delete "isothiazolidinecarbooxamide" and insert
-- isothiazolidinecarboxamide --;
Line 50, delete "2-[4-(2-furyl)benlzyl]" and insert -- 2-[4-(2-furyl)benzyl] --;
Line 55, delete "3isothiazolidinecarboxamide" and insert
-- 3-isothiazolidinecarboxamide --;

UNITED STATES PATENT AND TRADEMARK OFFICE
CERTIFICATE OF CORRECTION

PATENT NO. : 6,927,216 B2
DATED : August 9, 2005
INVENTOR(S) : Robert J. Cherney and Bryan W. King It is certified that error appears in the above-identified patent and that said Letters Patent is hereby corrected as shown below:

Column 88,
Line 61, delete "(2-methyl-4-quilonilyl)" and insert -- (2-methyl-4-quinolinyl) --;
Line 63, delete "(2-methyl4-quinolinyl)" and insert -- (2-methyl-4-quinolinyl) --;
Line 65, delete "(2-methy-4quinolinyl)" and insert -- (2-methyl-4-quinolinyl) --;

Column 89,
Line 5, delete "-2H-1,2thiazine-3-carboxamide" and insert
-- -2H-1,2-thiazine-3-carboxamide --.

Signed and Sealed this

Eleventh Day of April, 2006

JON W. DUDAS
*Director of the United States Patent and Trademark Office*